(12) United States Patent
Lu et al.

(10) Patent No.: US 11,649,220 B2
(45) Date of Patent: May 16, 2023

(54) PROBUCOL DERIVATIVE, PREPARATION METHOD THEREFOR AND USE THEREOF

(71) Applicant: DEMOTECH.INC., Beijing (CN)

(72) Inventors: Song Lu, Beijing (CN); Wenwei Xie, Beijing (CN); Shuangjiang He, Beijing (CN)

(73) Assignee: DEMOTECH.INC., Beijing (CN)

( * ) Notice: Subject to any disclaimer, the term of this patent is extended or adjusted under 35 U.S.C. 154(b) by 0 days.

(21) Appl. No.: 16/965,720

(22) PCT Filed: Jan. 18, 2019

(86) PCT No.: PCT/CN2019/072315
§ 371 (c)(1),
(2) Date: Jul. 29, 2020

(87) PCT Pub. No.: WO2019/149091
PCT Pub. Date: Aug. 8, 2019

(65) Prior Publication Data
US 2021/0040052 A1 Feb. 11, 2021

(30) Foreign Application Priority Data
Jan. 30, 2018 (CN) .......................... 201810090320.9

(51) Int. Cl.
| | | |
|---|---|---|
| C07D 265/30 | (2006.01) | |
| C07D 249/08 | (2006.01) | |
| C07D 311/58 | (2006.01) | |
| C07D 339/04 | (2006.01) | |
| C07D 495/04 | (2006.01) | |
| C07C 323/22 | (2006.01) | |

(52) U.S. Cl.
CPC .......... *C07D 265/30* (2013.01); *C07C 323/22* (2013.01); *C07D 249/08* (2013.01); *C07D 311/58* (2013.01); *C07D 339/04* (2013.01); *C07D 495/04* (2013.01)

(58) Field of Classification Search
CPC .. C07D 265/30; C07D 249/08; C07D 311/58; C07D 339/04; C07D 495/04; C07C 323/22
See application file for complete search history.

(56) References Cited

U.S. PATENT DOCUMENTS

| | | | |
|---|---|---|---|
| 3,862,332 A | | 1/1975 | Barnhart et al. |
| 4,985,465 A | | 1/1991 | Hendler |
| 5,002,967 A | * | 3/1991 | Mueller ............... A61K 31/365 |
| | | | 562/431 |
| 5,262,439 A | | 11/1993 | Parthasarathy |
| 5,321,046 A | * | 6/1994 | Sit .......................... C07C 319/14 |
| | | | 514/522 |
| 6,121,319 A | | 9/2000 | Somers |
| 9,650,332 B1 | | 5/2017 | Xu et al. |
| 2003/0064967 A1 | | 4/2003 | Luchoomun et al. |
| 2003/0176511 A1 | | 9/2003 | Stocker |
| 2005/0090487 A1 | * | 4/2005 | Somers .................... A61P 11/00 |
| | | | 514/408 |
| 2008/0280979 A1 | * | 11/2008 | Scott ......................... A61P 3/10 |
| | | | 514/548 |

FOREIGN PATENT DOCUMENTS

| | | |
|---|---|---|
| CN | 1263522 A | 8/2000 |
| CN | 101284808 A | 10/2008 |
| CN | 101428012 A | 5/2009 |
| CN | 101631538 A | 1/2010 |
| CN | 101686676 A | 3/2010 |
| CN | 101766594 A | 7/2010 |
| CN | 1263462 A | 8/2010 |
| CN | 106176717 A | 12/2016 |
| CN | 106905208 A | 6/2017 |
| CN | 108299263 A | 7/2018 |
| WO | 199851662 A2 | 11/1998 |
| WO | 200177072 A2 | 10/2001 |
| WO | 2005102323 A2 | 11/2005 |

(Continued)

OTHER PUBLICATIONS

Wu et al. JEM 2006, 203, 1117-1127 (Year: 2006).*
Ma et al. Journal of Geriatric Cardiology 2012, 9, 228-236 (Year: 2012).*
Xiao et al. Angew. Chem. Int. Ed. 2016, 55, 14121-14125 (Year: 2016).*
Demkowicz et al. Synthesis 2008, 13, 2033-2038 (Year: 2008).*
Antoniow et al. Synthesis 2007, 3, 0363-0366 (Year: 2007).*
International Search Report regarding PCT/CN2019/072315; dated Apr. 25, 2019.

* cited by examiner

*Primary Examiner* — Matthew P Coughlin
(74) *Attorney, Agent, or Firm* — Dickinson Wright PLLC

(57) ABSTRACT

The present invention relates to the field of compounds, and in particular to a probucol derivative, a preparation method therefor and use thereof, the probucol derivative having a structure represented by general formula I. The probucol derivative provided in the present invention can be used for the prevention and treatment of vascular diseases including diabetes, cardio-cerebrovascular diseases or complications thereof, and can be effectively used for reducing blood glucose, reducing blood lipid, reducing cholesterol, reducing body weight, reducing triglyceride, anti-inflammatory, and anti-oxidation, etc., having broad prospective applications.

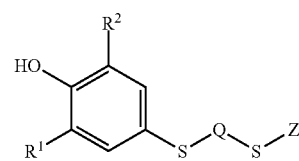

5 Claims, No Drawings

(56) References Cited

FOREIGN PATENT DOCUMENTS

| WO | 2007044726 | A2 | 4/2007 |
|----|------------|----|--------|
| WO | 2007142581 | A1 | 12/2007 |
| WO | 2011019747 | A1 | 2/2011 |

PROBUCOL DERIVATIVE, PREPARATION METHOD THEREFOR AND USE THEREOF

CROSS-REFERENCE TO RELATED APPLICATION

The present application is the National Stage of International Application No. PCT/CN2019/072315, filed Jan. 18, 2019, which claims priority to Chinese Patent Application No. 201810090320.9, entitled "Probucol derivative, preparation method therefor and use thereof" filed on Jan. 30, 2018, which are incorporated herein by reference in its entirety.

TECHNICAL FIELD

The present invention relates to the technical field of medicine, specifically, to a probucol derivative, preparation method therefor and use thereof in fields of different diseases.

BACKGROUND ART

Obesity easily leads to disorders of glucose and lipid metabolisms, which are the main causes of diabetes, atherosclerosis and aging. Glucose and lipid metabolisms may occur not only independently but also often simultaneously in the above diseases. As a result of glycosylation of biological macromolecules, diabetic patients are more prone to lipid metabolism disorders and consequent various complications, such as nephropathy, retinopathy, neuropathy, atherosclerotic cardio-cerebrovascular diseases, tumors and neurodegenerative diseases. Diabetes complications, especially vascular complications, are the main cause of death.

Probucol is a lipid-lowering drug marketed in the United States in the 1970s. The drug has strong antioxidant activity, could lower blood lipid, inhibit peroxidation of LDL, delay atherosclerosis and reduce cardiovascular and cerebrovascular events. At present, as an important lipid-lowering drug, especially for patients with familial hyperlipidemia, probucol is still widely used and valued. Published patents disclose different uses of probucol. For example, U.S. Pat. No. 3,862,332 discloses the use of probucol to lower serum cholesterol; U.S. Pat. No. 4,985,465 discloses the use of probucol in the inhibition of virus and transcriptional virus infections; CN200810246677.8 and CN201610591938.4 disclose the use of probucol combined with statins; and CN200880007795.1 discloses the use of probucol in chronic pulmonary obstruction. Probucol has the following chemical structure:

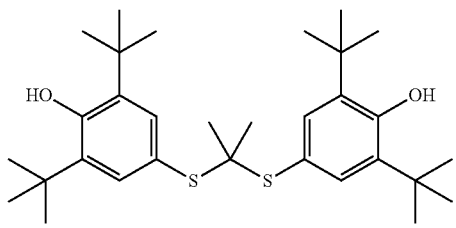 [SMILES: CC(C)(Sc1cc(C(C)(C)C)c(O)c(C(C)(C)C)c1)Sc1cc(C(C)(C)C)c(O)c(C(C)(C)C)c1]

Probucol is limited in the range of application for the reason that the drug itself has relatively weak efficacy in lowering blood glucose and blood lipid and the QT interval in some patients is prolonged. At the same time, due to the physical and chemical properties, there is a need of further improvement of probucol for clinical use, for example, probucol has an excessively high fat solubility and therefore is essentially insoluble in water, and probucol has low bioavailability, and thus it has high variability in drug absorption.

In order to overcome the shortcomings of probucol, several solutions are disclosed in the patents. For example, U.S. Pat. No. 5,262,439 discloses the use of prodrug technology to introduce one or two ester groups on the phenolic hydroxyl group of probucol so as to increase water solubility; U.S. Pat. No. 9,650,332 and CN201710107801.1 disclose the use of prodrug technology to introduce water-soluble groups and to treat related diseases; US20030064967 discloses probucol monoesters, pharmaceutically acceptable salts and prodrugs thereof, and the use thereof in raising HDL; CN98807171 discloses the use of probucol monoesters in the treatment of cardiovascular diseases and inflammatory diseases; U.S. Pat. No. 6,121,319 discloses the use of probucol monoesters in the treatment of cardiovascular diseases and inflammatory diseases; CN200880016419.9 discloses the use of probucol derivatives in the treatment of diabetes; and CN200810167035.9 discloses the combined use of AGI-1067 and pantethine.

AGI-1067 is one of the derivatives of probucol, which is obtained by the formation of monosuccinate on one phenolic hydroxyl group of probucol, as disclosed in patents WO98/09781 and WO2007/044726. The introduction of a carboxyl group increases the water solubility, partially solving some of the shortcomings in the physical and chemical properties of probucol. At the same time, AGI-1067 maintains the core structure of probucol, and thus has antioxidant and anti-inflammatory properties. AGI-1067 has the following chemical structure:

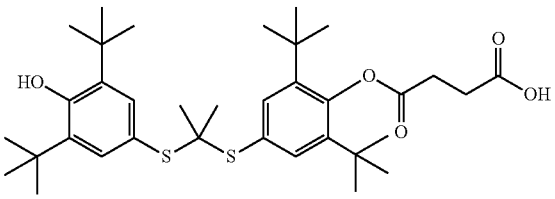 [SMILES: CC(C)(Sc1cc(C(C)(C)C)c(O)c(C(C)(C)C)c1)Sc1cc(C(C)(C)C)c(OC(=O)CCC(=O)O)c(C(C)(C)C)c1]

Probucol and its monosuccinate derivative AGI-1067 have been indicated in clinical studies to show commonalities and differences in the reduction of cholesterol and LDL-C, improvement of insulin resistance, reduction of blood glucose HbAlc, various vascular endothelial factors and inflammatory factors, facilitation of the expression of oxidative stress-related enzymes, anti-atherosclerosis, significantly less new-onset diabetes and significantly less stable cardio-cerebrovascular events and the like, which shows that the series of compounds based on probucol have great prospects in the treatment of cardiovascular diseases complicated with diabetes. Theories and clinical practice have confirmed that the current single-targeted drugs lack ideal efficacy in the intervention of cardiovascular diseases complicated with diabetes, and thus it is predicted that the corresponding therapeutic drug needs a multifunctional compound with good effects on glucose metabolism, lipid metabolism and inflammatory response.

SUMMARY OF THE INVENTION

The first object of the present invention is to provide a probucol derivative, the probucol derivative provided by the present invention having the structure represented by general formula I:

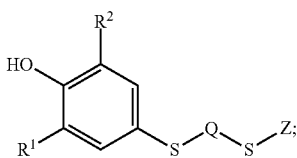

wherein $R^1$ and $R^2$ are the same or different, and each independently selected from hydrogen, an alkyl or alkoxy group;

The alkyl group or the alkoxy group (that is, the hydrogen of the alkyl group or of the alkyl group in the alkoxy group, the same below) is optionally substituted with one or more selected from a hydroxyl group, a cycloalkyl group, an alkenyl group, an ester group, a carboxylic group, a cyano group, an amino group, a nitro group, an amide group, a sulfonyl group, $-ONO_2$, an ether group, an aryl group, a heteroaryl group or halogen; $R^1$ or $R^2$ may be independently linked to the adjacent phenolic hydroxyl group to form a ring; the amino group can be optionally substituted with alkyl group or cycloalkyl group;

Q is absent or is $-CR^5R^6$, where $R^5$ and $R^6$ are the same or different, and each independently selected from an alkyl group, an alkenyl group, or an aryl group. The alkyl group, alkenyl group, or aryl group is optionally substituted with one or more selected from a hydroxyl group, an alkyl group, an alkenyl group, an amide group, an ester group, a carboxylic group, a cyano group, an amino group, a nitro group or halogen; $R^5$ and $R^6$ may be linked together to form a ring; the amino group is optionally substituted with a branched or linear alkyl group containing $C_1$-$C_6$ or a 3- to 5-membered cycloalkyl group;

Z is selected from an aryl or alkyl group; the alkyl group is optionally substituted with halogen, a hydroxyl group, a cycloalkyl group, an alkenyl group, a cyano group, an amino group, an aryl group, a heteroaryl group, $-NR^{12}R^{13}$, $-OR^{12}$, $-COOR^{12}$, $-CONR^{12}R^{13}$, $-NR^{12}COR^{13}$, $-SO_2R^{12}$, $-ONO_2$, $-SO_3H$, $-CO_2H$ or $-NR^{12}SO_2R^{13}$;

The aryl group is optionally substituted with halogen, a hydroxyl group, an alkyl group, an alkoxy group, a cycloalkyl group, an alkenyl group, a cyano group, an amino group, a heteroaryl group, $-NR^{12}R^{13}$, $-OR^{12}$, $-COOR^{12}$, $-CONR^{12}R^{13}$, $-NR^{12}COR^{13}$, $-SO_2R^{12}$, $-ONO_2$, $-SO_3H$, $-CO_2H$ or $-NR^{12}SO_2R^{13}$;

$R^{12}$ and $R^{13}$ are the same or different, and each independently selected from a hydroxyl group, an alkyl group, a cycloalkyl group, an alkenyl group, an amide group, an ester group, a carbonyl group, a cyano group, an amino group, a nitro group, halogen, a saturated heterocyclic group, an aryl group or a heteroaryl group; $R^{12}$ and $R^{13}$ may independently form a ring;

Preferably, $R^1$ and $R^2$ are the same or different, and each independently selected from hydrogen, an alkyl group or alkoxy group containing 1 to 6 carbon atoms;

The hydrogen of the alkyl group or of the alkyl group in the alkoxy group is optionally substituted with one or more (preferably one) selected from a hydroxyl group, a cycloalkyl group, an alkenyl group, an ester group, a carboxylic group, a cyano group, an amino group, a nitro group, an amide group, a sulfonyl group, $-ONO_2$, an ether group, an aryl group, a heteroaryl group or halogen; more preferably, $R^1$ and $R^2$ are the same or different, and each independently selected from hydrogen, an alkyl or alkoxy group containing 1 to 6 carbon atoms, the hydrogen atom in the alkyl group or the alkoxy group containing 1 to 6 carbon atoms is optionally substituted with one hydroxyl group, carboxylic group, cyano group, or amino group;

Q is absent or is $-CR^5R^6$, wherein $R^5$ and $R^6$ are the same or different, and each independently selected from an alkyl or aryl group. The alkyl group is selected from a branched or linear alkyl group containing 1 to 6 carbon atoms, and more preferably all of $R^5$ and $R^6$ are methyl groups. The aryl group is optionally substituted with a hydroxyl group, an alkyl group, an alkenyl group, an ester group, a carboxylic group, a cyano group, an amide group, a sulfonyl group, an ether group or halogen, preferably the aryl group is a monocyclic aromatic hydrocarbyl group, more preferably is a phenyl group;

Z is selected from a substituted monocyclic aryl group or a $C_1$-$C_6$ linear or branched alkyl group. The alkyl group is optionally substituted with halogen, a hydroxyl group, a cycloalkyl group, an alkenyl group, a cyano group, an amino group, an aryl group, a heteroaryl group, $-NR^{12}R^{13}$, $-OR^{12}$, $-COOR^{12}$, $-CONR^{12}R^{13}$, $-NR^{12}COR^{13}$, $-SO_2R^{12}$, $-ONO_2$, $-SO_3H$, $-CO_2H$ or $-NR^{12}SO_2R^{13}$. The substituted monocyclic aryl group is optionally substituted with halogen, a hydroxyl group, an alkyl group, an alkoxy group, an alkenyl group, a cyano group, $-NR^{12}R^{13}$, $-OR^{12}$, $-COOR^{12}$, $-CONR^{12}R^{13}$, $-NR^{12}COR^{13}$, $-SO_2R^{12}$, $-ONO_2$, $-SO_3H$, $-CO_2H$ or $-NR^{12}SO_2R^{13}$;

$R^{12}$ and $R^{13}$ are the same or different, and each independently selected from a hydroxyl group, an alkyl group, a cycloalkyl group, an alkenyl group, an amide group, an ester group, a carbonyl group, a cyano group, an amino group, halogen, a saturated heterocyclic group, an aryl group or a heteroaryl group; $R^{12}$ and $R^{13}$ may independently form a ring;

In the above $R^1$, $R^2$, Q, Z, $R^{12}$ and $R^{13}$, the following definitions are provided:

The cycloalkyl group is selected from a saturated or partially unsaturated cyclic hydrocarbyl group, preferably a 3- to 12-membered monocyclic or bicyclic group, more preferably a 3- to 8-membered monocyclic group, and still more preferably a 3- to 5-membered monocyclic group.

The alkenyl group is selected from a linear or branched alkenyl group containing at least one double bond of C=C and 2 to 12 carbon atoms, preferably a $C_3$-$C_8$ alkenyl group.

The amino group is a $-N$-alkyl group or a $-N$-cycloalkyl group. The alkyl group in the $-N$-alkyl group is selected from a branched or linear alkyl group containing 1 to 6 carbon atoms. The cycloalkyl group in the $-N$-cycloalkyl group is selected from a saturated or partially unsaturated cyclic hydrocarbyl group, preferably a 3- to 12-membered monocyclic or bicyclic group, more preferably a 3- to 8-membered monocyclic group, further preferably a 3- to 5-membered monocyclic group.

The ether group is an $-O$-alkyl group, and the alkyl group in the $-O$-alkyl group is selected from a branched or linear alkyl group containing 1 to 6 carbon atoms.

The aryl group is selected from an optionally substituted aromatic hydrocarbyl group containing 6 to 20 carbon atoms, preferably a monocyclic aromatic hydrocarbyl group, a bicyclic aromatic hydrocarbyl group or a polycyclic aromatic hydrocarbyl group, more preferably the aryl group is a phenyl group.

The heteroaryl group is selected from a 5- to 7-membered aromatic monocyclic group or an 8- to 12-membered aromatic bicyclic group containing at least one heteroatom which is selected from N, O or S, and the other atoms are carbon. Preferably the number of the heteroatom is 1 to 4, more preferably 1 to 3.

The ester group is a —(O)C-substituent group, and the substituent group is an alkyl or aryl group. The alkyl group is selected from a branched or linear alkyl group containing 1 to 6 carbon atoms. Further, the alkyl group may be substituted with an amino group, a substituted amino group, a saturated heterocyclic group, an aromatic cyclic group, an aromatic heterocyclic group, a carboxylic group or a sulfonic acid group. The aryl group is a monocyclic or bicyclic aromatic hydrocarbyl group, preferably a phenyl group.

The amide group is a —NHC(O)-substituent group, and the substituent group is selected from an alkyl or aryl group. The alkyl group is selected from a branched or linear alkyl group containing 1 to 6 carbon atoms. Further, the alkyl group may be substituted with an amino group, a substituted amino group, a saturated heterocyclic group, an aromatic cyclic group, an aromatic heterocyclic group, a carboxylic group or a sulfonic acid group. The aryl group is a monocyclic or bicyclic aromatic hydrocarbyl group, preferably a phenyl group.

The sulfonyl group is a —NHS(O)$_2$-substituent group, and the substituent group is selected from an alkyl group, a cycloalkyl group or an aryl group, preferably a linear or branched alkyl group containing 1 to 6 carbon atoms, or a 3- to 5-membered monocyclic cycloalkyl group, or monocyclic aryl group.

The saturated heterocyclic group is selected from a 4- to 12-membered saturated monocyclic, bicyclic or tricyclic group, including at least one carbon atom in addition to at least one heteroatom which is selected from N, O or S. The number of the heteroatom is 1 to 4, preferably 1 to 3, more preferably 1 or 2. The saturated heterocyclic group is preferably a monocyclic group.

Unless otherwise specified, "optionally substituted" in the present invention means that the corresponding group/atom may or may not be substituted. In general, "substitution" refers to the substitution of the hydrogen atom on the corresponding group. For example, the expression that "an alkyl or alkoxy group is optionally substituted" means that the hydrogen on the alkyl group or on the alkyl group in the alkoxy group is substituted.

As a preferred embodiment of the present invention, the probucol derivative of the present invention has the structure represented by general formula II.

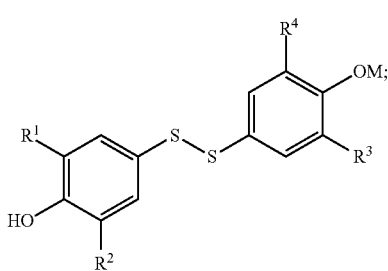

II where, $R^1$, $R^2$, $R^3$ and $R^4$ are the same or different, and each independently selected from hydrogen, an alkyl or alkoxy group;

The hydrogen of the alkyl group or of the alkyl group in the alkoxy group is optionally substituted with one or more selected from a hydroxyl group, a cycloalkyl group, an alkenyl group, an ester group, a carboxylic group, a cyano group, an amino group, a nitro group, an amide group, a sulfonyl group, —ONO$_2$, an ether group, an aryl group, a heteroaryl group or halogen. $R^1$ or $R^2$ may be independently linked to the adjacent phenolic hydroxyl group to form a ring. The amino group is optionally substituted with an alkyl or cycloalkyl group;

M is selected from hydrogen or —CO(CH$_2$)$_m$CONHR$^{14}$, m is an integer of 2 to 4. $R^{14}$ is selected from an alkyl group, an aryl group or a heteroaryl group, and the alkyl group is optionally substituted with a carboxylic group, a sulfonic acid group, —ONO$_2$, an amide group or a cyano group;

In the above structure of the present invention,

Preferably, $R^1$, $R^2$, $R^3$ and $R^4$ are the same or different, and each independently selected from hydrogen, an alkyl or alkoxy group containing 1 to 6 carbon atoms;

The hydrogen of the alkyl group or of the alkyl group in the alkoxy group is optionally substituted with one or more selected from a hydroxyl group, a cycloalkyl group, an alkenyl group, an ester group, a carboxylic group, a cyano group, an amino group, a nitro group, an amide group, a sulfonyl group, —ONO$_2$, an ether group, an aryl group, a heteroaryl group or halogen. $R^1$ or $R^2$ may be independently linked to the adjacent phenolic hydroxyl group to form a ring;

More preferably, $R^1$, $R^2$, $R^3$ and $R^4$ are each independently selected from a $C_1$-$C_6$ linear or branched alkyl group which is optionally substituted with one or more selected from a hydroxyl group, an ester group, a carboxylic group, an amino group, an amide group, a sulfonyl group, an aryl group or a heteroaryl group.

In some examples, when M is hydrogen, $R^1$, $R^2$, $R^3$ and $R^4$ are each independently selected from hydrogen or a $C_1$-$C_6$ linear or branched alkyl group which is optionally substituted with one or more selected from a hydroxyl group, an ester group, a carboxylic group, an amino group, an amide group, a sulfonyl group, an aryl group or a heteroaryl group. $R^3$ or $R^4$ may be independently linked to the adjacent phenolic hydroxyl group to form a ring.

Preferably, when M is hydrogen, $R^1$, $R^2$, $R^3$ and $R^4$ are each independently selected from hydrogen or a $C_1$-$C_6$ linear or branched alkyl group which is optionally substituted with one or more hydroxyl groups.

In some examples, when M is —CO(CH$_2$)$_m$CONHR$^{14}$, m is 2 to 3 (preferably 2), and $R^{14}$ is a C2-C6 linear or branched alkyl group, the terminal of which is optionally substituted with a carboxylic group or a sulfonic acid group.

In the above $R^1$, $R^2$, $R^3$, $R^4$, M and $R^{14}$, the following definitions are provided: The cycloalkyl group is selected from a saturated or partially unsaturated cyclic hydrocarbyl group, preferably a 3- to 12-membered monocyclic or bicyclic group, more preferably a 3- to 8-membered monocyclic group, and still more preferably a 3- to 5-membered monocyclic group.

The alkenyl group is selected from a linear or branched alkenyl group containing at least one double bond of C=C and 2 to 12 carbon atoms, preferably a C3-C8 alkenyl group.

The amino group is a —N-alkyl group or a —N-cycloalkyl group. The alkyl group in the —N-alkyl group is selected from a branched or linear alkyl group containing 1 to 6 carbon atoms. The cycloalkyl group in the —N-cycloalkyl group is selected from a saturated or partially unsaturated cyclic hydrocarbyl group, preferably a 3- to 12-membered monocyclic or bicyclic group, more preferably a 3- to 8-membered monocyclic group, further preferably a 3- to 5-membered monocyclic group.

The ether group is an —O-alkyl group, and the alkyl group in the —O-alkyl group is selected from a branched or linear alkyl group containing 1 to 6 carbon atoms.

The aryl group is selected from an optionally substituted aromatic hydrocarbyl group containing 6 to 20 carbon atoms, preferably a monocyclic aromatic hydrocarbyl group, a bicyclic aromatic hydrocarbyl group or a polycyclic aromatic hydrocarbyl group. More preferably the aryl group is a phenyl group.

The heteroaryl group is selected from a 5- to 7-membered aromatic monocyclic group or an 8- to 12-membered aromatic bicyclic group containing at least one heteroatom which is selected from N, O or S, and the other atoms are carbon. Preferably the number of the heteroatom is 1 to 4, more preferably 1 to 3.

The ester group is a —(O)C-substituent group, and the substituent group is an alkyl or aryl group. The alkyl group is selected from a branched or linear alkyl group containing 1 to 6 carbon atoms. Further, the alkyl group may be substituted with an amino group, a substituted amino group, a saturated heterocyclic group, an aromatic cyclic group, an aromatic heterocyclic group, a carboxylic group or a sulfonic acid group. The aryl group is a monocyclic or bicyclic aromatic hydrocarbyl group, preferably a phenyl group.

The amide group is a —NHC(O)-substituent group, and the substituent group is selected from an alkyl or aryl group. The alkyl group is selected from a branched or linear alkyl group containing 1 to 6 carbon atoms. Further, the alkyl group may be substituted with an amino group, a substituted amino group, a saturated heterocyclic group, an aromatic cyclic group, an aromatic heterocyclic group, a carboxylic group or a sulfonic acid group. The aryl group is a monocyclic or bicyclic aromatic hydrocarbyl group, preferably a phenyl group.

The sulfonyl group is a —NHS(O)$_2$-substituent group, and the substituent group is selected from an alkyl group, a cycloalkyl group or an aryl group, preferably a linear or branched alkyl group containing 1 to 6 carbon atoms, or a 3- to 5-membered monocyclic cycloalkyl, or monocyclic aryl group.

As another preferred embodiment of the present invention, the probucol derivative of the present invention has the structure represented by general formula III:

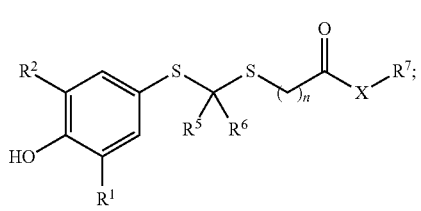

where, $R^1$ and $R^2$ are the same or different, and each independently selected from hydrogen, an alkyl or alkoxy group.

The hydrogen of the alkyl group or of the alkyl group in the alkoxy group is optionally substituted with one or more selected from a hydroxyl group, a cycloalkyl group, an alkenyl group, an ester group, a carboxylic group, a cyano group, an amino group, a nitro group, an amide group, a sulfonyl group, —ONO$_2$, an ether group, an aryl group, a heteroaryl group or halogen. $R^1$ or $R^2$ may be independently linked to the adjacent phenolic hydroxyl group to form a ring. The amino group is optionally substituted with an alkyl or cycloalkyl group.

$R^5$ and $R^6$ are the same or different, and each independently selected from an alkyl group, an alkenyl group or an aryl group. The alkyl group, alkenyl group or aryl group is optionally substituted with one or more selected from a hydroxyl group, an alkyl group, an alkenyl group, an acyl group, an ester group, a carboxylic group, a cyano group, an amino group, a nitro group or halogen. $R^5$ and $R^6$ may be linked together to form a ring.

n is an integer of 1 to 4, X is N or O, $R^7$ is selected from hydrogen or an alkyl group, and the alkyl group is optionally substituted with one or more selected from a hydroxyl group, a cycloalkyl group, an alkenyl group, an acyl group, an ester group, a carboxylic group, a cyano group, an amino group, a nitro group, an aromatic cyclic group, an aromatic heterocyclic group or halogen.

In the above structure of the present invention,

Preferably, $R^1$ and $R^2$ are each independently selected from a $C_1$-$C_6$ alkyl group which is optionally substituted with one or more selected from an ester group, a carboxylic group, a sulfonic acid group, an amino group or a hydroxyl group. The ester group is a —(O)C-substituent group, and the substituent group is an alkyl or aryl group. The alkyl group is selected from a branched or linear alkyl group containing 1 to 6 carbon atoms. Further, the alkyl group may be substituted with an amino group, a saturated heterocyclic group, an aromatic cyclic group, an aromatic heterocyclic group, a carboxylic group or a sulfonic acid group. The aryl group is a monocyclic or bicyclic aromatic hydrocarbyl group, preferably a phenyl group.

More preferably, $R^1$ and $R^2$ are each independently selected from a $C_2$-$C_5$ branched or linear alkyl group which is optionally substituted with one or more selected from a hydroxyl group, a carboxylic group, a sulfonyl group or an amino group.

In some examples, $R^1$ and $R^2$ are the same and both selected from an alkyl group containing 2 to 5 carbon atoms (preferably tertiary butyl).

Preferably, $R^5$ and $R^6$ are each independently selected from an alkyl or aryl group. The alkyl group is selected from a branched or linear alkyl group containing 1 to 6 carbon atoms, and the aryl group is selected from a substituted aromatic hydrocarbyl group, preferably monocyclic aromatic hydrocarbyl group, more preferably a phenyl group.

In some examples, $R^5$ and $R^6$ are each independently selected from methyl or ethyl.

In some examples, $R^5$ and $R^6$ are each independently selected from a phenyl group.

Preferably, n is an integer of 2 to 3.

Preferably, $R^7$ is hydrogen or a $C_1$-$C_6$ branched or linear alkyl group which is optionally substituted with one or more selected from an acyl group, an ester group, or a sulfonic acid group.

In some examples, $R^1$ and $R^2$ are independently selected from a $C_2$-$C_5$ branched or linear alkyl group which is optionally substituted with one or more selected from a hydroxyl group, an ester group or a sulfonic acid group. n is an integer of 2 to 3, X is N or O, $R^7$ is hydrogen, methyl or ethyl, and $R^5$ and $R^6$ are methyl.

In the above $R^1$, $R^2$, $R^5$, $R^6$ and $R^7$, the cycloalkyl group, alkenyl group, amino group, ether group, aryl group, heteroaryl group, ester group, amide group, sulfonyl group and the like have the same definitions as in the compounds represented by general formula I or II.

As another preferred embodiment of the present invention, the probucol derivative of the present invention has the structure represented by general formula IV:

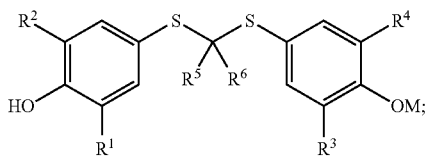

where, $R^1$, $R^2$, $R^3$ and $R^4$ are the same or different, and each independently selected from hydrogen, an alkyl or alkoxy group.

The hydrogen of the alkyl group or of the alkyl group in the alkoxy group is optionally substituted with one or more selected from a hydroxyl group, a cycloalkyl group, an alkenyl group, an ester group, a carboxylic group, a cyano group, an amino group, a nitro group, an amide group, a sulfonyl group, —$ONO_2$, an ether group, an aryl group, a heteroaryl group or halogen. $R^1$, $R^2$, $R^3$ or $R^4$ may be independently linked to the adjacent phenolic hydroxyl group to form a ring. The amino group is optionally substituted with an alkyl or cycloalkyl group.

M is selected from hydrogen or —$CO(CH_2)_mCONHR^{14}$, m is an integer of 2 to 4. $R^{14}$ is selected from an alkyl group, an aryl group or a heteroaryl group, and the alkyl group is optionally substituted with a carboxylic group, a sulfonic acid group, —$ONO_2$, an amide group or a cyano group.

$R^5$ and $R^6$ are the same or different, and each independently selected from an alkyl group, an alkenyl group or an aryl group. The alkyl group, alkenyl group or aryl group is optionally substituted with one or more selected from a hydroxyl group, an alkyl group, an alkenyl group, an amide group, an ester group, a carboxylic group, a cyano group, an amino group, a nitro group or halogen. $R^5$ and $R^6$ may be linked together to form a ring. The amino group is optionally substituted with branched or linear alkyl group containing $C_1$-$C_6$ or a 3- to 5-membered cycloalkyl group.

In the above structures of the present invention,

Preferably, $R^1$, $R^2$, $R^3$ and $R^4$ are the same or different, and each independently selected from hydrogen, an alkyl or alkoxy group containing 1 to 6 carbon atoms.

The hydrogen of the alkyl group or of the alkyl group in the alkoxy group is optionally substituted with one or more selected from a hydroxyl group, a cycloalkyl group, an alkenyl group, an ester group, a carboxylic group, a cyano group, an amino group, a nitro group, an amide group, a sulfonyl group, —$ONO_2$, an ether group, an aryl group, a heteroaryl group or halogen. $R^1$ or $R^2$ may be independently linked to the adjacent phenolic hydroxyl group to form a ring.

More preferably, $R^1$, $R^2$, $R^3$ and $R^4$ are each independently selected from a $C_1$-$C_6$ linear or branched alkyl group which is optionally substituted with one or more selected from a hydroxyl group, an ester group, a carboxylic group, an amino group, an amide group, a sulfonyl group, an aryl group or a heteroaryl group.

Preferably, $R^5$ and $R^6$ are the same or different, and each independently selected from an alkyl or aryl group. The alkyl group is selected from a branched or linear alkyl group containing 1 to 6 carbon atoms, and more preferably both of $R^5$ and $R^6$ are methyl groups. The aryl group is optionally substituted with a hydroxyl group, an alkyl group, an alkenyl group, an ester group, a carboxylic group, a cyano group, an amide group, a sulfonyl group, an ether group or halogen, preferably the aryl group is a monocyclic aromatic hydrocarbyl group, and more preferably the aryl group is a phenyl group.

In some examples, when M is hydrogen, $R^1$, $R^2$, $R^3$ and $R^4$ are each independently selected from hydrogen or a $C_1$-$C_6$ linear or branched alkyl group which is optionally substituted with one or more selected from a hydroxyl group, an ester group, a carboxylic group, an amino group, an amide group, a sulfonyl group, an aryl group or a heteroaryl group. $R^3$ or $R^4$ may be independently linked to the adjacent phenolic hydroxyl group to form a ring.

Preferably, when M is hydrogen, $R^1$, $R^2$, $R^3$ and $R^4$ are each independently selected from hydrogen or a $C_1$-$C_6$ linear or branched alkyl group which is optionally substituted with one or more hydroxyl groups.

In some examples, when M is —$CO(CH_2)_mCONHR^{14}$, m is 2 to 3 (preferably 2), and $R^{14}$ is a $C_2$-$C_6$ linear or branched alkyl group, the terminal of which is optionally substituted with a carboxylic group or a sulfonic acid group.

In the above $R^1$, $R^2$, $R^3$, $R^4$, M and $R^{14}$, the cycloalkyl group, alkenyl group, amino group, ether group, aryl group, heteroaryl group, ester group, amide group, sulfonyl group and the like have the same definitions as in the compounds represented by general formula I or II.

Further, the probucol derivative of the present invention has the structure represented by general formula V:

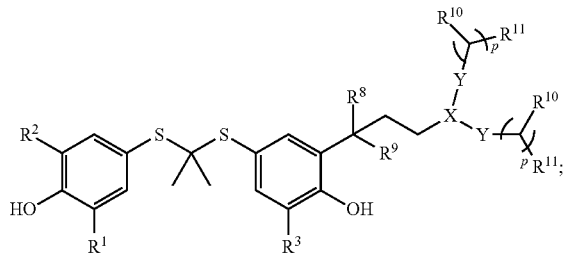

where, $R^1$, $R^2$ and $R^3$ are the same or different, and each independently selected from hydrogen, an alkyl or alkoxy group.

The hydrogen of the alkyl group or of the alkyl group in the alkoxy group is optionally substituted with one or more selected from a hydroxyl group, a cycloalkyl group, an alkenyl group, an ester group, a carboxylic group, a cyano group, an amino group, a nitro group, an amide group, a sulfonyl group, —$ONO_2$, an ether group, an aryl group, a heteroaryl group or halogen. $R^1$ or $R^2$ may be independently linked to the adjacent phenolic hydroxyl group to form a ring. The amino group is optionally substituted with an alkyl or cycloalkyl group.

$R^8$ and $R^9$ are the same or different, and each independently selected from a $C_1$-$C_6$ linear or branched alkyl group, a cycloalkyl group, an aryl group or a heteroaryl group.

X is N, O or S; Y is a heteroaryl group, —$CH_2$— or —$C(O)$.

When X is O or S, only one Y can be present.
When X is N, one or two Y are present.
p is an integer from 0 to 6.
$R^{10}$ and $R^{11}$ are the same or different, and each independently selected from hydrogen, an amino group, an aryl group, a heteroaryl group or an alkyl group. The amino group, aryl group, heteroaryl group or alkyl group is each independently and optionally substituted with halogen, a hydroxyl group, a saturated heterocyclic hydrocarbyl group, an alkenyl group, a cyano group, an aryl group, a heteroaryl group, —$NR^{15}R^{16}$, —$OR^{15}$, —$COOR^{15}$, —$CONR^{15}R^{16}$, —$NR^{15}COR^{16}$, —$SO_2R^{15}$, —$ONO_2$, —$SO_3H$, —$CO_2H$ or —$NR^{15}SO_2R^{16}$. The saturated heterocyclic hydrocarbyl group is selected from a 4- to 12-membered saturated monocyclic, bicyclic or tricyclic group, including at least one carbon atom in addition to at least one heteroatom which is selected from N, O or S. The number of the heteroatom is 1 to 4, preferably 1 to 3, more preferably 1 or 2. Preferably the saturated heterocyclic hydrocarbyl group is monocyclic group. $R^{15}$ and $R^{16}$ are the same or different, and each independently selected from a hydroxyl group, an alkyl group, a cycloalkyl group, an alkenyl group, an amide group, an ester group, a carbonyl group, a sulfonic acid group, a cyano group, an amino group, a nitro group, halogen, an aryl group or an heteroaryl group. $R^{15}$ and $R^{16}$ may independently form a ring.

In the above structure of the present invention,

Preferably, $R^1$, $R^2$ and $R^3$ are the same or different, and each independently selected from hydrogen, an alkyl or alkoxy group. The alkyl group or the alkyl group in the alkoxy group is optionally substituted with one or more selected from a hydroxyl group, a cycloalkyl group, an ester group, a carboxylic group, a cyano group, an amino group, an amide group, a sulfonyl group, —$ONO_2$, an ether group, an aryl group, a heteroaryl group or halogen. More preferably $R^1$, $R^2$ and $R^3$ are the same or different, and each independently selected from hydrogen, an alkyl or alkoxy group. The alkyl group or the alkyl group in the alkoxy group is optionally substituted with one or more selected from a hydroxyl group, a cycloalkyl group, an ester group, a carboxylic group, a cyano group, an amino group, an amide group, a sulfonyl group, —$ONO_2$ or an ether group.

Preferably, $R^8$ and $R^9$ are the same or different, and each independently selected from a $C_1$-$C_6$ linear or branched alkyl group, a cycloalkyl group, an aryl group or a heteroaryl group. Further preferably, $R^8$ and $R^9$ are the same or different, and each independently selected from a $C_1$-$C_6$ linear or branched alkyl group or a cycloalkyl group. More preferably $R^8$ and $R^9$ are all methyl.

Preferably, $R^{10}$ and $R^{11}$ are the same or different, and each independently selected from hydrogen, an amino group, an aryl group or an alkyl group. The amino group, aryl group or alkyl group each is optionally substituted with halogen, a hydroxyl group, a saturated heterocyclic hydrocarbyl group, an aryl group, a heteroaryl group, —$NR^{15}R^{16}$, —$OR^{15}$, —$COOR^{15}$, —$CONR^{15}R^{16}$, —$NR^{15}COR^{16}$, —$SO_2R^{15}$, —$ONO_2$, —$SO_3H$, —$CO_2H$ or —$NR^{15}SO_2R^{16}$. $R^{15}$ and $R^{16}$ may independently form a ring. More preferably, $R^{10}$ and $R^{11}$ are the same or different, and each independently selected from an amino group, an aryl group or an alkyl group. The amino group, aryl group or alkyl group each is optionally substituted with halogen, a hydroxyl group, a saturated heterocyclic hydrocarbyl group, an aryl group, a heteroaryl group, —$NR^{15}R^{16}$, —$OR^{15}$, —$COOR^{15}$, —$CONR^{15}R^{16}$, —$NR^{15}COR^{16}$, —$ONO_2$, —$SO_3H$, —$CO_2H$ or —$NR^{15}SO_2R^{16}$. $R^{15}$ and $R^{16}$ may independently form a ring.

Further preferably, $R^{10}$ and $R^{11}$ are the same or different, and each independently selected from a $C_1$-$C_6$ alkyl group. The alkyl group is optionally substituted with a saturated heterocyclic hydrocarbyl group, an aryl group, a heteroaryl group, —$NR^{15}R^{16}$, —$OR^{15}$, —$COOR^{15}$, —$CONR^{15}R^{16}$, —$NR^{15}COR^{16}$, —$ONO_2$, —$SO_3H$, —$CO_2H$ or —$NR^{15}SO_2R^{16}$. $R^{15}$ and $R^{16}$ may independently form a ring.

In some examples, when X is preferably N, p is 0, Y is heteroaryl, more preferably triazolyl and tetrazolyl.

As a preferred structure, in the structure represented by general formula V of the present invention:

$R^1$, $R^2$ and $R^3$ are the same or different, and each independently selected from a $C_1$-$C_6$ linear or branched alkyl group. The alkyl group is optionally substituted with one or more selected from a hydroxyl group, an alkyl group, an acyl group, an ester group, and a carbonyl group, further preferably tertiary butyl.

X is O or N.

Y is —C(O)—.

p is an integer of 1 to 4.

$R^8$ and $R^9$ are the same or different, and each independently selected from a $C_1$-$C_6$ linear or branched alkyl group, a cycloalkyl group, an aryl group or a heteroaryl group. Further preferably, $R^8$ and $R^9$ are the same or different, and each independently selected from a $C_1$-$C_6$ linear or branched alkyl group or a cycloalkyl group. More preferably $R^8$ and $R^9$ are both methyl.

$R^{10}$ and $R^{11}$ are the same or different, and each independently selected from an amino group, an aryl group or an alkyl group. The amino group, aryl group or alkyl group each is optionally substituted with halogen, a hydroxyl group, a saturated heterocyclic hydrocarbyl group, an aryl group, a heteroaryl group, —$NR^{15}R^{16}$, —$OR^{15}$, —$COOR^{15}$, —$CONR^{15}R^{16}$, —$NR^{15}COR^{16}$, —$ONO_2$, —$SO_3H$, —$CO_2H$ or —$NR^{15}SO_2R^{16}$. $R^{15}$ and $R^{16}$ may independently form a ring. More preferably, $R^{10}$ and $R^{11}$ are the same or different, and each independently selected from an alkyl group which is optionally substituted with a saturated heterocyclic hydrocarbyl group, an aryl group, a heteroaryl group, —$NR^{15}R^{16}$, —$OR^{15}$, —$COOR^{15}$, —$CONR^{15}R^{16}$, —$NR^{15}COR^{16}$, —$ONO_2$, —$SO_3H$, —$CO_2H$ or —$NR^{15}SO_2R^{16}$. $R^{15}$ and $R^{16}$ may independently form a ring.

In the above $R^1$, $R^2$, $R^3$, $R^8$, $R^9$, $R^{10}$, $R^{11}$, $R^{15}$ and $R^{16}$, the cycloalkyl group, alkenyl group, amino group, ether group, aryl group, heteroaryl group, ester group, amide group, sulfonyl group and the like have the same definitions as in the compounds represented by general formula II.

More preferably, the probucol derivative provided by the present invention are preferably the following compounds:

1: methyl 2-((2-((3,5-di-tert-butyl-4-hydroxyphenyl)thio)propan-2-yl)thio)acetate
2: 2-((2-((3,5-di-tert-butyl-4-hydroxyphenyl)thio)propan-2-yl)thio)acetic acid
3: ethyl 3-((2-((3,5-di-tert-butyl-4-hydroxyphenyl)thio)propan-2-yl)thio)propionate
4: 3-((2-((3,5-di-tert-butyl-4-hydroxyphenyl)thio)propan-2-yl)thio)propanoic acid
5: 4,4'-disulfanediyl-bis(2-(tert-butyl)-6-(1-hydroxyethyl)phenol)
6: 2,6-di-tert-butyl-4-((3-(tert-butyl)-4-hydroxy-5-(4-hydroxy-2-methylbutan-2-yl)phenyl)disulfanediyl)phenol
7: 4,4'-(propane-2,2-diylbis(thio))bis(2-methoxyphenol)
8: 2,6-di-tert-butyl-4-((2-((3-(tert-butyl)-4-hydroxy-5-(4-hydroxy-2-methylbutan-2-yl)phenyl)thio)propan-2-yl)thio)phenol
9: 4,4'-(propane-2,2-diylbis(thio))bis(2-(tert-butyl)-6-(4-hydroxy-2-methylbutan-2-yl)phenol)
10: 2,6-di-tert-butyl-4-((2-((8-(tert-butyl)-4,4-dimethylchroman-6-yl)thio)propan-2-yl)thio)phenol 11: 4-(3-(3-(tert-butyl)-5-((2-((3,5-di-tert-butyl-4-hydroxyphenyl)thio)propan-2-yl)thio)-2-hydroxyphenyl)-3-methylbutoxy)-4-oxobutanoic acid
12: 3-(3-(tert-butyl)-5-((2-((3,5-di-tert-butyl-4-hydroxyphenyl)thio)propan-2-yl)thio)-2-hydroxyphenyl)-3-methylbutyl 5-(1,2-dithiolan-3-yl)pentanoate
13: 3-(3-(tert-butyl)-5-((2-((3,5-di-tert-butyl-4-hydroxyphenyl)thio)propan-2-yl)thio)-2-hydroxyphenyl)-3-methylbutyl 2-acetoxybenzoate
14: 3-(3-(tert-butyl)-5-((2-((3,5-di-tert-butyl-4-hydroxyphenyl)thio)propan-2-yl)thio)-2-hydroxyphenyl)-3-methylbutyl acetate
15: (S)-3-(3-(tert-butyl)-5-((2-((3,5-di-tert-butyl-4-hydroxyphenyl)thio)propan-2-yl)thio)-2-hydroxyphenyl)-3-methylbutyl 2-(2-chlorophenyl)-2-(6,7-dihydrothieno[3,2-c]pyridin-5(4H)-yl)acetate
16: 2-(4-amino-2-methylbutan-2-yl)-6-(tert-butyl)-4-((2-((3,5-di-tert-butyl-4-hydroxyphenyl)thio)propan-2-yl)thio)phenol
17: 2,6-di-tert-butyl-4-((2-((3-(tert-butyl)-5-(4-(2-(diethylamino)ethoxy)-2-methylbutan-2-yl)-4-hydroxyphenyl)thio)propan-2-yl)thio)phenol
18: 2,6-di-tert-butyl-4-((2-((3-(tert-butyl)-4-hydroxy-5-(2-methyl-4-(2-morpholinoethoxy)butan-2-yl)phenyl)thio)propan-2-yl)thio)phenol
19: 3-(3-(tert-butyl)-5-((2-((3,5-di-tert-butyl-4-hydroxyphenyl)thio)propan-2-yl)thio)-2-hydroxyphenyl)-3-methylbutyl glycinate
20: 3-(3-(tert-butyl)-5-((2-((3,5-di-tert-butyl-4-hydroxyphenyl)thio)propan-2-yl)thio)-2-hydroxyphenyl)-3-methylbutyl alaninate
21: methyl 2-((3-(3-(tert-butyl)-5-((2-((3,5-di-tert-butyl-4-hydroxyphenyl)thio)propan-2-yl)thio)-2-hydroxyphenyl)-3-methylbutyl)aminoacetate
22: dimethyl 2,2'-((3-(3-(tert-butyl)-5-((2-((3,5-di-tert-butyl-4-hydroxyphenyl)thio)propan-2-yl)thio)-2-hydroxyphenyl)-3-methylbutyl)azanediyl)diacetate
23: N-(3-(3-(tert-butyl)-5-((2-((3,5-di-tert-butyl-4-hydroxyphenyl)thio)propan-2-yl)thio)-2-hydroxyphenyl)-3-methylbutyl)-5-(1,2-dithiolan-3-yl)pentanamide
24: 2,6-di-tert-butyl-4-((2-((3-(tert-butyl)-4-hydroxy-5-(2-methyl-4-(1H-1,2,4-triazol-1-yl)butan-2-yl)phenyl)thio)propan-2-yl)thio)phenol
25: N-(3-(3-(tert-butyl)-5-((2-((3,5-di-tert-butyl-4-hydroxyphenyl)thio)propan-2-yl)thio)-2-hydroxyphenyl)-3-methylbutyl)cyclopropanesulfonamide
26: 2-(4-(2,6-di-tert-butyl-4-((2-((3,5-di-tert-butyl-4-hydroxyphenyl)thio)propan-2-yl)thio)phenoxy)-4-oxobutanamido)ethane-1-sulfonic acid
27: 2-(4-(3-(3-(tert-butyl)-5-((2-((3,5-di-tert-butyl-4-hydroxyphenyl)thio)propan-2-yl)thio)-2-hydroxyphenyl)-3-methylbutoxy)-4-oxobutanamido)ethane-1-sulfonic acid.

The present invention also provides isomers (stereoisomers, enantiomers, racemates, cis-trans isomers, tautomers), and isotopic compounds of the above probucol derivative, and any combination of them; or a pharmaceutically acceptable salt thereof.

Depending on the type or combination of substituent groups, the probucol derivatives of the present invention may have various isomers. Preferably the isomers are stereoisomers (for example, "cis" and "trans" forms, enantiomers), tautomers and optical isomers (for example, dextrorotatory and levorotatory forms). The compounds of the present invention also include all these isomers, stereoisomers and mixtures of these isomers and stereoisomers in any ratio, unless otherwise specified.

The probucol derivative of the present invention may contain unnatural proportions of isotopes as one or more constituent atoms. Examples of isotopes include deuterium (2H), tritium (3H), iodine-125 (125I) and carbon-14 (14C). All isotope variants of probucol derivatives represented by general formulas I to V are also included within the scope of the present invention.

The probucol derivative described in the present invention may be prepared by conventional technical means in the art. In order to obtain the probucol derivative better, as the second object of the present invention, the preferred preparation method of the probucol derivative is also provided.

The preparation process and specific steps of the probucol derivative are as follows:

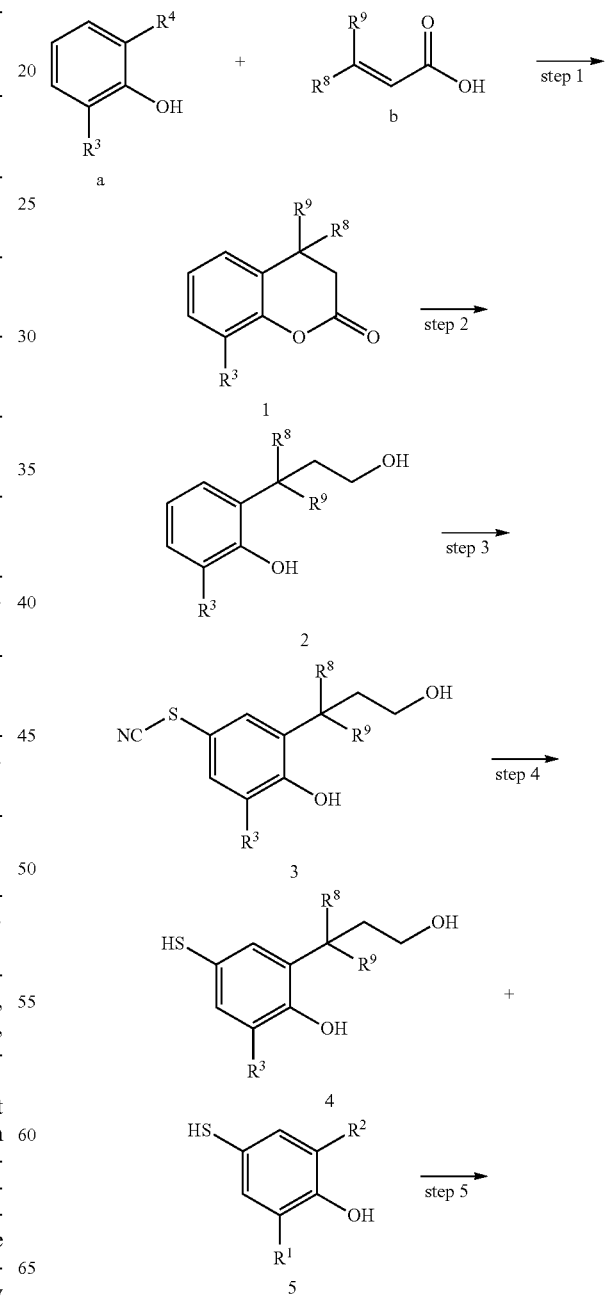

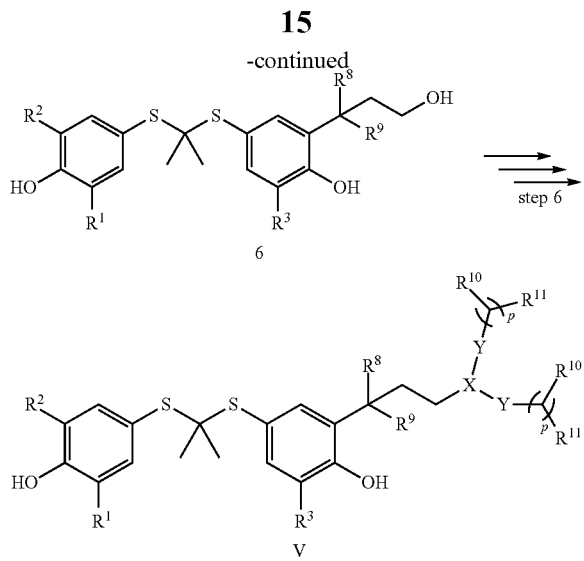

Step 1: raw material compound (a) and raw material compound (b) are subjected to reactions of addition of alkenes and esterifying condensation-cyclization to obtain intermediate 1;

Step 2: the intermediate 1 is subjected to a reduction ring-opening reaction to obtain intermediate 2;

Step 3: a thiocyano group is introduced into the intermediate 2 through a thiocyanation reaction to obtain intermediate 3;

Step 4: the intermediate 3 is subjected to a reduction reaction to obtain intermediate 4;

Step 5: the intermediate 4 and an intermediate 5 are docked through a condensation reaction to obtain an intermediate 6;

Step 6: the intermediate 6 is subjected to reactions of condensation, alkylation or sulfonylation to obtain different compounds of general formula V.

The $R^1$, $R^2$, $R^3$, $R^4$, $R^8$, $R^9$, $R^{10}$, $R^{11}$, X, Y, p and the like have the same definitions as in the probucol derivative of the present invention.

In the above preparation method of the present invention, the reactions in Steps 1 to 6 could be achieved using conventional reaction conditions known in the art, which is not particularly limited in the present invention.

The present invention also provides a pharmaceutical composition, wherein the pharmaceutical composition comprises, as an active ingredient, at least one probucol derivative according to the present invention or its stereoisomers, enantiomers, racemates, cis-trans isomers, tautomers, isotopic compounds and any combinations of them, or pharmaceutically acceptable salts thereof, or further comprises pharmaceutically acceptable excipients.

In the pharmaceutical composition of the present invention, the probucol derivative may be used as the only active ingredient, or may be used in combination with other known active ingredients.

Preferably, the pharmaceutical composition is in a dosage form including, but not limited to, a solid dosage form such as a capsule, a troche, a tablet, a sugar-coated tablet, granules and powder, a liquid dosage form such as an elixir, a syrup, an emulsion, a dispersion, and a suspension.

The above pharmaceutical composition (each dosage form) may be prepared by the conventional technical means in the art, and the invention is not particularly limited thereto. A person skilled in the art may select appropriate excipients and preparation methods according to the actual conditions to realize the present invention.

The present invention also provides a method for treating cardiovascular diseases complicated with diabetes, and the method comprises administering to a patient in need thereof a therapeutically effective amount of the probucol derivative of the present invention, or its stereoisomer, or a pharmaceutically acceptable salt thereof, or the pharmaceutical composition of the present invention.

Another object of the present invention is to provide use of the probucol derivative of the present invention, or its stereoisomers, enantiomers, racemates, cis-trans isomers, tautomers thereof, isotope compounds, and any combination of them, or a pharmaceutically acceptable salt thereof, or a pharmaceutical composition of the present invention, in the manufacture of a medicament for the treatment of aging and diabetes, cardio-cerebrovascular diseases or complications thereof.

Preferably, the diabetes and cardio-cerebrovascular diseases include but are not limited to, hyperglycemia, hyperlipidemia, hypercholesterolemia, hypertriglyceridemia, fatty liver, obesity, cardio-cerebrovascular diseases complicated with diabetes, nephropathy complicated with diabetes and retinopathy complicated with diabetes.

The probucol derivative provided by the invention exhibits outstanding therapeutic and relieving effects on the above-mentioned diseases, and could be effectively used for lowering blood glucose, lowering blood lipid, lowering cholesterol, lowering body weight, lowering triglyceride, anti-inflammatory and anti-oxidation and the like, and has broad application prospects.

SPECIFIC MODES FOR CARRYING OUT THE EMBODIMENTS

The probucol derivative and/or pharmaceutically acceptable salt thereof disclosed in the present invention could be synthesized from commercially available starting materials according to the contents disclosed in the present invention. The following schemes describe the preparation methods of some of the compounds disclosed in the present invention. The Examples and Preparation Examples below are provided for enabling a person skilled in the art to more clearly understand and implement the present invention. They are not intended to limit the scope of the present invention, but are merely for illustration and representation. Generally, the compounds of the present invention are automatically named by means of the professional software chemoffice 14.0 based on the IUPAC system. If there is an inconsistency between the structure drawn and the name given by the corresponding structure, the structure drawn shall prevail. In addition, if the stereochemistry of the structure or part of the structure is not indicated by, for example, bold or dashed lines, the structure or part of the structure is explained to include all stereoisomers thereof.

Unless otherwise indicated, the words, phrases and symbols used in this description generally have the following meanings. The abbreviations and terms used herein are given below.

The term "alkyl group" refers to a hydrocarbyl group selected from linear and branched saturated hydrocarbyl groups, and the saturated hydrocarbyl group comprises 1 to 18 carbon atoms, for example 1 to 12 carbon atoms, further for example 1 to 6 carbon atom. Examples of alkyl groups may be selected from methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or sec-butyl ("s-Bu"), 1,1-dimethylethyl or tertiary butyl ("t-Bu"). Other examples of alkyl groups may be selected from groups of 1-pentyl (n-pentyl, —$CH_2CH_2CH_2CH_2CH_3$), 2-pentyl (—$CH(CH_3)$ $CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)$ $CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)$ $CH_2CH_2CH_2CH_3$), 3-hexyl (—$CH(CH_2CH_3)$ $(CH_2CH_2CH_3)$), 2-methyl-2-pentyl (—$C$ $(CH_3)_2CH_2CH_2CH_3$), 3-methyl-2-pentyl (—$CH(CH_3)CH$ $(CH_3)CH_2CH_3$), 4-methyl-2-pentyl (—$CH(CH_3)CH_2CH$ $(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$) and 3,3-dimethyl-2-butyl (—$CH(CH_3)C(CH_3)_3$).

The term "alkenyl group" refers to a hydrocarbyl group selected from linear and branched hydrocarbyl groups comprising at least one double bond of C=C and 2 to 18, such as 2 to 6 carbon atoms. Examples of alkenyl groups may be selected from groups of vinyl (—$CH=CH_2$), 1-propenyl (—$CH=CHCH_3$), 2-propenyl (—$CH_2CH=CH_2$), 2-methyl-1-propenyl, 1-butenyl, 2-butenyl, 3-butenyl, 1,3-butadienyl, 2-methyl-1,3-butadienyl, 1-hexenyl, 2-hexenyl, 3-hexenyl, 4-hexenyl, and 1,3-hexadienyl.

The term "cycloalkyl" refers to a group selected from saturated and partially unsaturated cyclic hydrocarbyl groups, including monocyclic and polycyclic (e.g., bicyclic and tricyclic) groups. For example, the cycloalkyl group may include 3 to 12 carbon atoms, such as 3 to 8 carbon atoms, and further such as 3 to 6, 3 to 5, or 3 to 4 carbon atoms. Furthermore, the cycloalkyl group may be selected from monocyclic groups having 3 to 12, such as 3 to 8, 3 to 6, carbon atoms. Examples of the monocyclic cycloalkyl groups include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl. Examples of the bicyclic cycloalkyl groups include bicyclic groups or bridged bicyclic groups consisting of 7 to 12 ring atoms, the bicyclic group is selected from [4,4], [4,5], [5,5], [5,6] and [6,6] ring systems, and the bridged bicyclic group is selected from bicyclo[2.2.1]heptyl, bicyclo[2.2.2]octyl, and bicyclo[3.2.2]nonyl. The ring may be saturated or have at least one double bond (e.g., partially unsaturated), but is not completely conjugated, and is not aromatic as defined herein.

The term "saturated heterocyclic group" is a group selected from 4- to 12-membered saturated monocyclic, bicyclic or tricyclic groups, including at least one carbon atom in addition to at least one heteroatom selected from N, O or S. The number of the heteroatoms is from 1 to 4, preferably 1 to 3, more preferably 1 or 2. The saturated heterocyclic group is preferably monocyclic, such as piperidinyl, morpholinyl, 2-hydroxyethyl pyrrolyl, homopiperazinyl, piperazinyl and tetrahydropyranyl.

The term "aryl group" is a group selected from:
5- and 6-membered carbocyclic aromatic rings, for example, a phenyl group;
bicyclic systems such as 7- to 12-membered bicyclic systems in which at least one ring is a carbocyclic aromatic ring, such as the bicyclic system selected from, for example, naphthyl, indanyl and 1,2,3,4-tetrahydroquinolinyl; and tricyclic systems such as 10- to 15-membered tricyclic systems in which at least one ring is a carbocyclic aromatic ring, such as fluorenyl.

For example, the aryl group may be selected from aryl groups formed by fusing a 5- and 6-membered carbocyclic aromatic ring to a 5- to 7-membered cycloalkyl or heterocyclic group, and the 5- to 7-membered cycloalkyl or heterocyclic group optionally contain at least one heteroatom selected from N, O, and S, provided that the point of attachment is on the carbocyclic aromatic ring if the carbocyclic aromatic ring is fused with a heterocyclic group, or the point of attachment may be on the carbocyclic aromatic ring or on the cycloalkyl group if the carbocyclic aromatic ring is fused with a cycloalkyl group. A divalent group formed from a substituted benzene derivative and having free valences in the ring atoms is referred to as a substituted phenylene radical. The divalent radical of the polycyclic hydrocarbon is named by adding a "-ene" to the name of the corresponding monovalent radical thereof. For example, a group having two points of attachment and derived from naphthalene is referred to as a naphthylene group. The monovalent polycyclic hydrocarbyl group is obtained by removing a hydrogen atom from the free-valence carbon atom and named with a "-yl" at the end. However, in any case, the aryl group does not include the heteroaryl group or overlap with the heteroaryl group which will be defined below separately. Therefore, if one or more carbocyclic aromatic rings are fused with a heterocyclic aromatic ring, the resulting ring system is a heteroaryl group as defined in this description rather than an aryl group.

The term "halogen" or "halo" refers to F, Cl, Br or I.
The term "heteroaryl" is selected from:
a 5- to 7-membered aromatic monocyclic group, which includes at least one heteroatom, for example, from 1 to 4, or, in some embodiments, from 1 to 3, the heteroatoms are selected from N, O, and S, and the remaining ring atoms are carbon;
a 8- to 12-membered bicyclic group, which includes at least one heteroatom, for example, from 1 to 4, or, in some embodiments, from 1 to 3, or in other embodiments, 1 to 2, the heteroatoms are selected from N, O, and S, the remaining ring atoms are carbon and at least one ring is aromatic, and there is at least one heteroatom on the aromatic ring; and
a 11- to 14-membered tricyclic ring, which includes at least one heteroatom, for example, from 1 to 4, or, in some embodiments, from 1 to 3, or in other embodiments, 1 to 2, the heteroatoms are selected from N, O, and S, the remaining ring atoms are carbon and at least one ring is aromatic, and there is at least one heteroatom on the aromatic ring.

For example, the heteroaryl group includes a 5- to 7-membered heteroaromatic ring, which is fused with a 5- to 7-membered cycloalkane ring. For such a fused bicyclic heteroaromatic ring system in which only one ring contains at least one heteroatom, the point of attachment may be on the heteroaromatic ring or the cycloalkane ring.

When the total number of S and O atoms on the heteroaryl group is more than one, these heteroatoms will not be adjacent. In some embodiments, the total number of S and O on the heteroaryl group does not exceed two. In some embodiments, the total number of S and O on the heteroaromatic ring does not exceed one.

Examples of heteroaryl groups include, but are not limited to, (numbered from the attached position preferentially designated as 1) pyridyl (such as 2-pyridyl, 3-pyridyl, 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazole, tetrazolyl, thienyl, triazinyl, benzothienyl, furanyl, benzofuranyl, benzimidazolyl, indolyl, isoindolyl, indolinyl, phthalazinyl, pyrazinyl, pyridazinyl, pyrrolyl, triazolyl, quinolyl, isoquinolyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl, benzofuranyl, benzothienyl, benzothiazolyl, benzoxazolyl, quinazolinyl, quinoxalinyl, diazanaphthyl, furopyridinyl, benzothiazolyl (such as benzo[d]thiazol-6-yl), indazolyl (such as 1H-indazol-5-yl) and 5,6,7,8-tetrahydroisoquinolyl.

A single stereoisomer (e.g., a substantially pure enantiomer) may be obtained by resolving a racemic mixture, e.g. by a method of forming diastereomers using an optically active resolving agent. The racemic mixture of the chiral compound of the present invention may be separated by any suitable method, including: (1) forming an ionic, diastereomeric salt with the chiral compound, then separating the ionic, diastereomeric salt of the chiral compound by stepwise crystallization or other methods, (2) forming diastereoisomeric compounds with chiral derivatization reagents, then separating the formed diastereomers and converting them into pure stereoisomers, and (3) directly separating substantially pure or enriched stereoisomers under chiral conditions.

"Pharmaceutically acceptable salts" include, but are not limited to, inorganic acid salts, selected from, for example, hydrochloride, phosphate, hydrobromide, sulfate; also include organic salts, selected from, for example, malate, maleate, fumarate, tartrate, succinate, citrate, lactate, methanesulfonate, p-toluenesulfonate, benzoate, salicylate, stearate, alkanoates such as acetate and the salts of HOOC—(CH$_2$)$_n$—COOH in which n is selected from 0 to 4.

Similarly, examples of pharmaceutically acceptable cations include, but are not limited to, sodium, potassium, calcium, aluminum, lithium and ammonium.

In addition, if the compound described herein is obtained in the form of an acid addition salt, its free base may be obtained by alkalizing its salt solution. Conversely, if the compound described herein is obtained in the form of a free base, addition salts (e.g., pharmaceutically acceptable addition salts) may be prepared by dissolving the free base in a suitable organic solvent and treating the solution with an acid, which is in accordance with the usual procedure for the preparation of an acid addition salt from an alkaline compound. A person skilled in the art could identify various synthetic methods that can be used to prepare non-toxic pharmaceutically acceptable addition salts without undue experimentation.

"Pharmaceutically acceptable salts" as defined herein include salts of compounds, as well as salts of stereoisomers of compounds, such as salts of enantiomers, and/or salts of diastereomers.

"Treating" or "relieving" refers to administration of at least one compound and/or at least one stereoisomer thereof, and/or at least one pharmaceutically acceptable salt disclosed herein to a subject identified as in need thereof. For example, the subject has diabetes.

The term "effective amount" refers to an effective amount of at least one compound and/or at least one stereoisomer thereof, and/or at least one pharmaceutically acceptable salt disclosed herein, which may effectively "treat" (as defined above) the disease or dysfunction in the subject.

The term "at least one substituent group" described herein includes, for example, from 1 to 4, such as from 1 to 3, and further such as from 1 to 2 substituent groups.

Table 1 describes some examples of probucol derivatives according to general formula I.

Table 1

TABLE 1

| No. | Name | Structure of Compound |
|---|---|---|
| 1 | methyl 2-((2-((3,5-di-tert-butyl-4-hydroxyphenyl)thio)propan-2-yl)thio)acetate | |
| 2 | 2-((2-((3,5-di-tert-butyl-4-hydroxyphenyl)thio)propan-2-yl)thio)acetic acid | |

TABLE 1-continued

| No. | Name | Structure of Compound |
|---|---|---|
| 3 | ethyl 3-((2-((3,5-di-tert-butyl-4-hydroxyphenyl)thio)propan-2-yl)thio)propionate | |
| 4 | 3-((2-((3,5-di-tert-butyl-4-hydroxyphenyl)thio)propan-2-yl)thio)propanoic acid | |
| 5 | 4,4'-disulfanediyl-bis(2-(tert-butyl)-6-(1-hydroxyethyl)phenol) | |
| 6 | 2,6-di-tert-butyl-4-((3-(tert-butyl)-4-hydroxy-5-(4-hydroxy-2-methylbutan-2-yl)phenyl)disulfanediyl)phenol | |
| 7 | 4,4'-(propane-2,2-diylbis(thio))bis(2-methoxyphenol) | |
| 8 | 2,6-di-tert-butyl-4-((2-((3-(tert-butyl)-4-hydroxy-5-(4-hydroxy-2-methylbutan-2-yl)phenyl)thio)propan-2-yl)thio)phenol | |

TABLE 1-continued

| No. | Name | Structure of Compound |
|---|---|---|
| 9 | 4,4'-(propane-2,2-diylbis(thio))bis(2-(tert-butyl)-6-(4-hydroxy-2-methylbutan-2-yl)phenol) | |
| 10 | 2,6-di-tert-butyl-4-((2-((8-(tert-butyl)-4,4-dimethylchroman-6-yl)thio)propan-2-yl)thio)phenol | |
| 11 | 4-(3-(3-(tert-butyl)-5-((2-((3,5-di-tert-butyl-4-hydroxyphenyl)thio)propan-2-yl)thio)-2-hydroxyphenyl)-3-methylbutoxy)-4-oxobutanoic acid | |
| 12 | 3-(3-(tert-butyl)-5-((2-((3,5-di-tert-butyl-4-hydroxyphenyl)thio)propan-2-yl)thio)-2-hydroxyphenyl)-3-methylbutyl)-5-(1,2-dithiolan-3-yl)pentanoate | |
| 13 | 3-(3-(tert-butyl)-5-((2-((3,5-di-tert-butyl-4-hydroxyphenyl)thio)propan-2-yl)thio)-2-hydroxyphenyl)-3-methylbutyl)-2-acetoxybenzoate | |
| 14 | 3-(3-(tert-butyl)-5-((2-((3,5-di-tert-butyl-4-hydroxyphenyl)thio)propan-2-yl)thio)-2-hydroxyphenyl)-3-methylbutyl acetate | |

TABLE 1-continued

| No. | Name | Structure of Compound |
|---|---|---|
| 15 | (S)-3-(3-(tert-butyl)-5-((2-((3,5-di-tert-butyl-4-hydroxyphenyl)thio)propan-2-yl)thio)-2-hydroxyphenyl)-3-methylbutyl 2-(2-chlorophenyl)-2-(6,7-dihydrothieno[3,2-c]pyridin-5(4H-yl)acetate | |
| 16 | 2-(4-amino-2-methylbutan-2-yl)-6-(tert-butyl)-4-((2-((3,5-di-tert-butyl-4-hydroxyphenyl)thio)propan-2-yl)thio)phenol | |
| 17 | 2,6-di-tert-butyl-4-((2-((3-(tert-butyl)-5-(4,(2-diethylamino)ethoxy)-2-methylbutan-2-yl)-4-hydroxyphenyl)thio)propan-2-yl)thio)phenol | |
| 18 | 2,6-di-tert-butyl-4-((2-((3-(tert-butyl)-4-hydroxy-5-(2-methyl-4-(2-morpholinoethoxy)butan-2-yl)phenyl)thio)propan-2-yl)thio)phenol | |
| 19 | 3-(3-(tert-butyl)-5-((2-((3,5-di-tert-butyl-4-hydroxyphenyl)thio)propan-2-yl)thio)-2-hydroxyphenyl)-3-methylbutyl glycinate | |

TABLE 1-continued

| No. | Name |
|---|---|
| 20 | 3-(3-(tert-butyl)-5-((2-((3,5-di-tert-butyl-4-hydroxyphenyl)thio)propan-2-yl)thio)-2-hydroxyphenyl)-3-methylbutyl alaninate |
| 21 | methyl 2-((3-(3-(tert-butyl)-5-((2-((3,5-di-tert-butyl-4-hydroxyphenyl)thio)propan-2-yl)thio)-2-hydroxyphenyl)-3-methylbutyl)aminoacetate |
| 22 | dimethyl 2,2'-((3-(3-(tert-butyl)-5-((2-((3,5-di-tert-butyl-4-hydroxyphenyl)thio)propan-2-yl)thio)-2-hydroxyphenyl)-3-methylbutyl)azanediyl)diacetate |
| 23 | N-(3-(3-(tert-butyl)-5-((2-((3,5-di-tert-butyl-4-hydroxyphenyl)thio)propan-2-yl)thio)-2-hydroxyphenyl)-3-methylbutyl)-5-(1,2-dithiolan-3-yl)pentanamide |
| 24 | 2,6-di-tert-butyl-4-((2-((3-tert-butyl)-4-hydroxy-5-(2-methyl-4-(1H-1,2,4-triazol-1-yl)butan-2-yl)phenyl)thio)propan-2-yl)thio)phenol |

TABLE 1-continued

| No. | Name |
|---|---|
| 25 | N-(3-(3-(tert-butyl)-5-((2-((3,5-di-tert-butyl-4-hydroxyphenyl)thio)propan-2-yl)thio)-2-hydroxyphenyl)-3-methylbutyl)-cyclopropanesulfonamide |
| 26 | 2-(4-(2,6-di-tert-butyl-4-((2-((3,5-di-tert-butyl-4-hydroxyphenyl)thio)propan-2-yl)thio)-phenoxy)-4-oxobutanamido)ethane-1-sulfonic acid |
| 27 | 2-(4-(3-(3-di-tert-butyl)-5-((2-((3,5-di-tert-butyl-4-hydroxyphenyl)thio)propan-2-yl)thio)-2-hydroxyphenyl)-3-methylbutoxy)-4-oxobutanamido)ethane-1-sulfonic acid |
| 28 | 2,4,9,11-tetra-tert-butyl-14,14-dimethyl-13,15-dithiodispiro[5.0.5$^7$.3$^6$]pentadeca-1,4,8,11-tetraene-3,10-dione |
| 29 | 3,3',5,5'-tetra-tert-butyl-[1,1'-bi(cyclohexylidene)]-2,2',5,5'-tetraene-4,4'-dione |
| 30 | probucol |

TABLE 1-continued

| No. | Name | Structure of Compound |
|-----|------|----------------------|
| 31 | 4-(2,6-di-tert-butyl-4-((2-((3,5-di-tert-butyl-4-hydroxyphenyl)thio)propan-2-yl)thio)-phenoxy)-4-oxobutanoic acid (AG11067) | |

Note: Compounds 28-31 are known compounds and are included in the present application for reference.

Note: Compounds 28-31 are known compounds and are included in the present application for reference.

Synthesis Scheme:

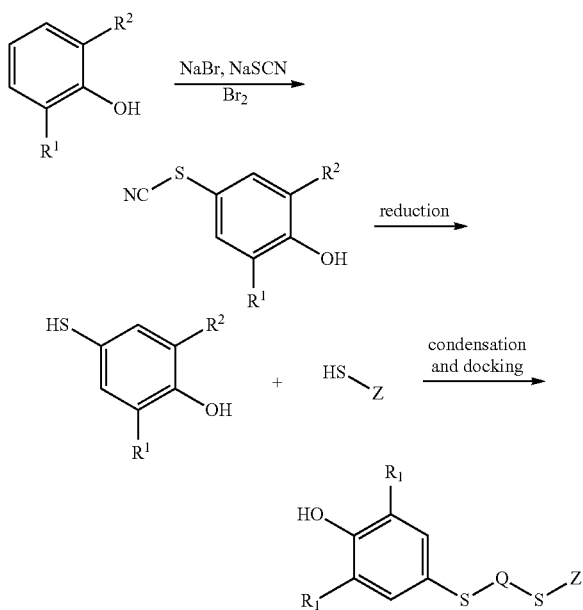

In this scheme, a thiocyano group is introduced into a commercial phenol or a phenol obtained by further derivation synthesis, according to the standard method described in the literatures, and then the product is subjected to reduction to obtain the phenylmercapto derivative. The mercapto-containing compound is further subjected to condensation and docking to obtain the compound represented by general formula I. It should be noted that only a part of the representative compounds is listed in the following Examples. It can be understood by a person skilled in the art that according to the synthesis methods disclosed in the present invention, other probucol derivatives described in the present invention could be obtained by appropriately replacing the raw materials only, which also falls within the scope of the present invention.

The following abbreviations are used in the following examples:
DCM dichloromethane
DMAP 4-N,N-dimethylaminopyridine
EDCI 1-(3-dimethylaminopropyl)-3-ethylcarbodiimide hydrochloride
HOBt 1-hydroxybenzotriazole
EtOAc ethyl acetate
PE petroleum ether
MeOH methanol
DMSO dimethyl sulfoxide
EtOH absolute ethanol
$K_2CO_3$ potassium carbonate
HOAc acetic acid
DIAD diisopropyl azodicarboxylate
LAH lithium aluminum hydride
NaBr sodium bromide
NaSCN sodium thiocyanate
$Br_2$ bromine
Acetone acetone
HCl hydrochloric acid
rt or r.t. room temperature
TBDPSCl tert-butyl diphenylchlorosilane
Im imidazole
BOMCl benzyl chloromethyl ether
TBAF tetrabutylammonium fluoride
THF tetrahydrofuran
$PPh_3$ triphenylphosphine
Hydrazine hydrazine
G or g gram
mg milligram
mL milliliter
L liter
mmol millimole
mol mole
$H_2O$ water
$Na_2SO_4$ sodium sulfate
NaCl sodium chloride
Eq equivalent
mi minute
$NaHCO_3$ sodium bicarbonate
HCl hydrochloric acid
MeLi methyl lithium
$N_2$ nitrogen
$MeSO_3H$ methanesulfonic acid
NaH sodium hydride
MsCl methanesulfonyl chloride
$Et_3N$ triethylamine
KI potassium iodide
DCC N,N'-dicyclohexylcarbodiimide
$MnO_2$ manganese dioxide
$O_2$ oxygen
KOH potassium hydroxide
Piperidine piperidine
DPPH 1,1-diphenyl-2-trinitrophenylhydrazine
OD value absorbance
General Conditions:
Unless otherwise described, all temperatures including melting points are in degrees Celsius. Unless otherwise stated, the following reactions are generally carried out in an anhydrous solution under a positive pressure of nitrogen. The reaction flask is equipped with a rubber stopper to facilitate the addition of substrates and reagents through a syringe, and the glassware is dried by oven drying and/or heating.

$^1$HNMR spectra were acquired using 300 MHz Varian equipment using common deuterated solvents such as CDCl$_3$, DMSO-d$_6$, CD$_3$OD, D$_2$O as the solvent, with tetramethylsilane as the standard or residual solvent (CDCl$_3$: 7.25 ppm; CD$_3$OD:3.31 ppm; D$_2$O 4.79 ppm; and DMSO-d$_6$ 2.50 ppm) as internal standards. The multiplicity of peaks is abbreviated as follows: s (singlet), d (doublets), t (triplets), q (quartets), qn (quintets), sx (sextets), m (multiplets), br (broad), dd (double doublets), dt (double triplets). The given coupling constant is expressed in Hertz (Hz).

Example 1: methyl 2-((2-((3,5-di-tert-butyl-4-hydroxyphenyl)thio)propan-2-yl)thio)acetate

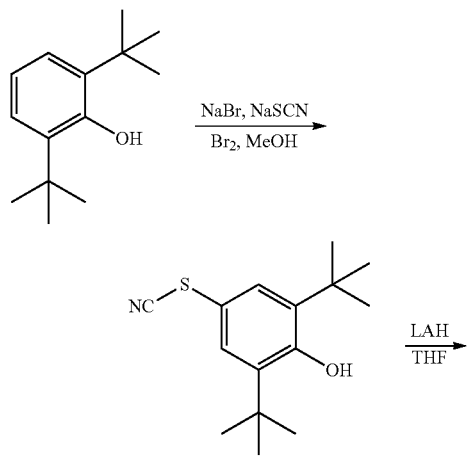

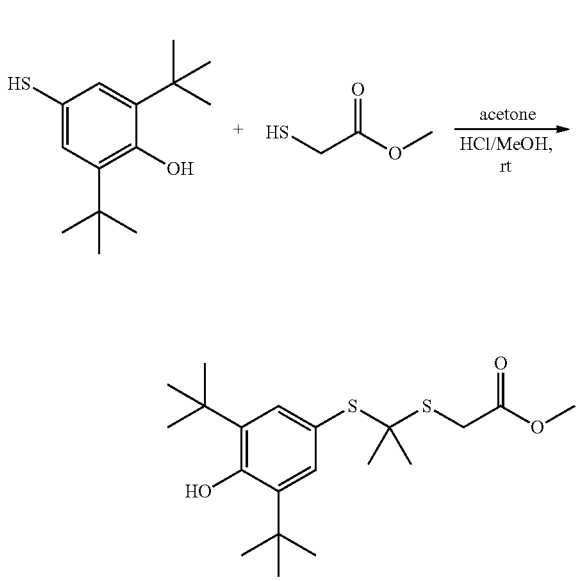

Step 1: 2,6-di-tert-butyl-4-thiocyanophenol

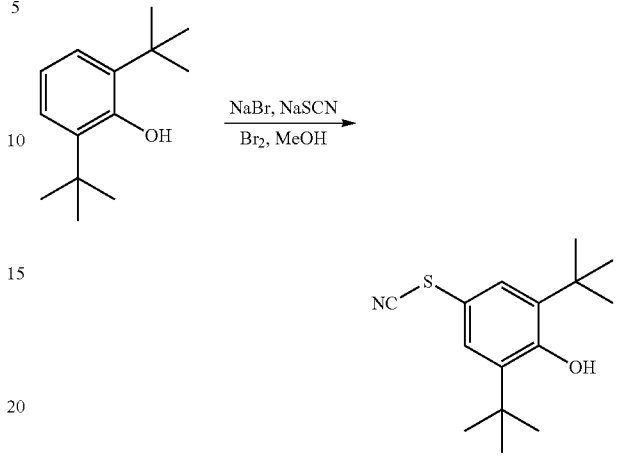

2,6-di-tert-butylphenol (2.06 g, 10 mmol), NaBr (1.02 g, 10 mmol) and NaSCN (1.62 g, mmol) were added to a three-necked flask containing MeOH (30 mL). The above mixture was cooled with an ice water bath, and the temperature was kept at 0 to 5° C. Then the solution of Br$_2$ (0.56 mL, 11 mmol) in MeOH (5 mL) was slowly added dropwise, the temperature was controlled to be 5° C. or less. After the dropwise addition was finished, the resulting mixture was naturally raised to room temperature under stirring, and the reaction was monitored by TLC. The methanol was removed by concentration under reduced pressure. To the residue was added H$_2$O (100 mL), the resultant was extracted with EtOAc (100 mL×3), and dried with Na$_2$SO$_4$. The EtOAc was removed by concentration under reduced pressure, and the crude 2,6-di-tert-butyl-4-thiocyanophenol was directly used in the next step.

Step 2: 2,6-di-tert-butyl-4-mercaptophenol

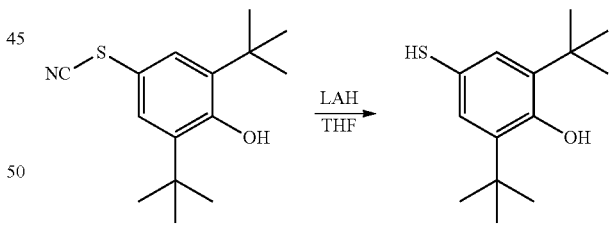

At 0° C., a solution of 2,6-di-tert-butyl-4-thiocyanophenol (10.0 g, crude) in dry THF (30 mL) was slowly added dropwise to a suspension of lithium aluminum hydride (2.0 g, 52.6 mmol) in THF (50 mL). The reaction was carried out at 0° C. for 5 hours. The reaction was quenched by slowly adding EtOAc (20 mL), and then 3N HCl (50 mL) and EtOAc (200 mL) were added. The organic phase was separated out, washed with saturated NaHCO$_3$ and saturated salt water, respectively, and dried with anhydrous sodium sulfate. The crude product was passed through a chromatography column (silica gel, EtOAc:PE=1:10 to 1:5) to obtain the product 2,6-di-tert-butyl-4-mercaptophenol (5.4 g) as a yellow waxy solid.

Step 3: methyl 2-((2-((3,5-di-tert-butyl-4-hydroxyphenyl)thio)propan-2-yl)thio)acetate

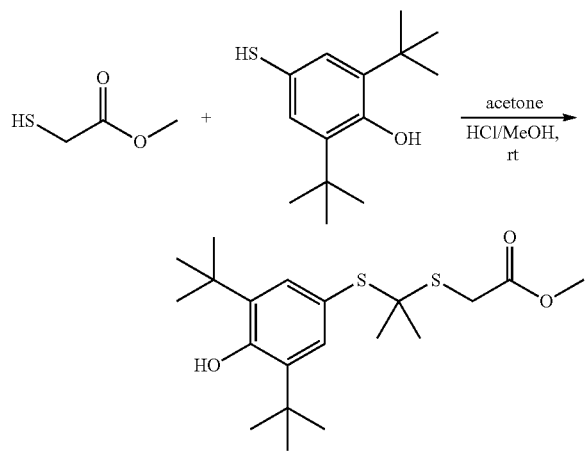

At 0° C., methyl 2-mercaptoacetate (1 mL) and 2,6-di-tert-butyl-4-mercaptophenol (0.88 g, 3.7 mmol) were added to dry acetone (20 mL), then MeOH (20 mL) was slowly added, and then HCl gas was slowly introduced to adjust pH to 2 to 3. The reaction solution was reacted at room temperature overnight. The organic solvent was removed under reduced pressure. To the residue was added EtOAc (100 mL), and the resultant was washed with saturated NaHCO$_3$ and saturated salt water, respectively, and dried with anhydrous sodium sulfate. The crude product was passed through a chromatography column (silica gel, EtOAc:PE=1:20 to 1:5) to obtain the product methyl 2-((2-((3,5-di-tert-butyl-4-hydroxyphenyl)thio)propan-2-yl)thio)acetate (444 mg, yield 22%), as a colorless liquid which was slowly solidified at room temperature.

$^1$H NMR (300 MHz, CDCl$_3$): δ 7.30 (s, 2H), 5.37 (s, 1H), 3.74 (s, 3H), 3.58 (s, 3H), 3.88 (s, 2H), 1.54 (s, 6H), 1.44 (s, 18H). LC-MS: 385.2 [M+H]$^+$. HPLC: 93.0% at 242 nm, $t_R$=4.18 min.

Example 2: 2-((2-((3,5-di-tert-butyl-4-hydroxyphenyl)thio)propan-2-yl)thio)acetic acid

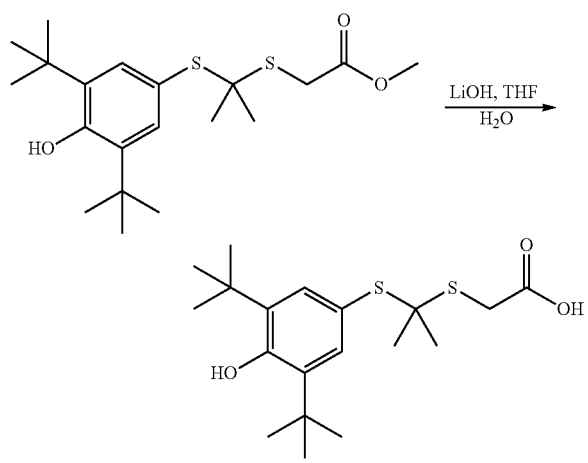

At 0° C., water and lithium hydroxide (218 mg, 5.2 mmol) were added to methyl 2-((2-((3,5-di-tert-butyl-4-hydroxyphenyl)thio)propan-2-yl)thio)acetate (200 mg, 0.52 mmol) in THF (5 mL). The reaction solution was stirred at room temperature overnight, then EtOAc (50 mL) was added, and then 1N HCl (5 mL) was added. The organic phase was separated out, washed with saturated salt water and dried with anhydrous sodium sulfate. The crude product was passed through a chromatography column (silica gel, EtOAc:PE=1:1 to 3:1) to obtain the product 2-((2-((3,5-di-tert-butyl-4-hydroxyphenyl)thio)propan-2-yl)thio)acetic acid (120 mg, yield 62%) as a yellow solid. $^1$H NMR (300 MHz, CDCl$_3$): δ 7.31 (s, 2H), 5.38 (s, 1H), 3.63 (s, 2H), 1.55 (s, 6H), 1.43 (s, 18H). LC-MS: 371 [M+H]$^+$. HPLC: 98.1% at 242 nm, $t_R$=2.11 min.

Example 3: ethyl 3-((2-((3,5-di-tert-butyl-4-hydroxyphenyl)thio)propan-2-yl)thio)propionate

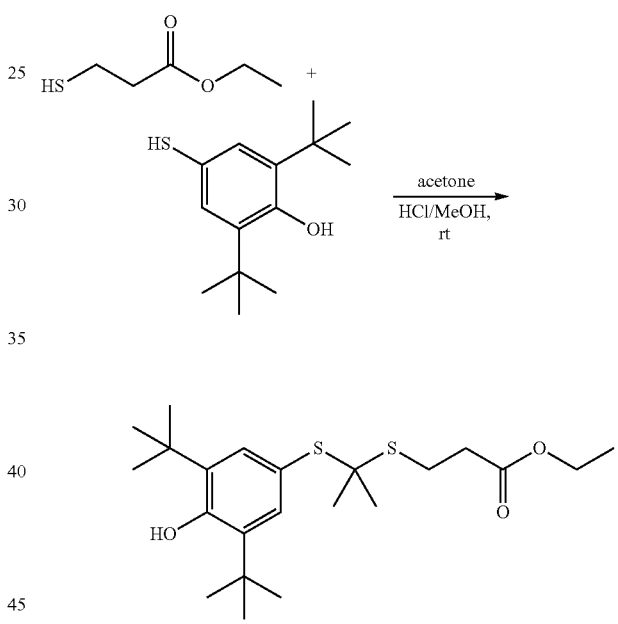

At 0° C., ethyl 3-mercaptopropionate (1.7 g, 12.8 mmol) and 2,6-di-tert-butyl-4-mercaptophenol (1.5 g, 6.3 mmol) were added to dry acetone (20 mL), then MeOH (20 mL) was slowly add dropwise at 0° C., and then HCl gas was slowly introduced to adjust pH to 2 to 3. The reaction solution was reacted at room temperature overnight. The organic solvent was removed under reduced pressure. To the residue was added EtOAc (100 mL), and the resultant was washed with saturated NaHCO$_3$ and saturated salt water, respectively, and dried with anhydrous sodium sulfate. The crude product was passed through a chromatography column (silica gel, EtOAc:PE=1:50 to 1:20) to obtain the product ethyl 3-((2-((3,5-di-tert-butyl-4-hydroxyphenyl)thio)propan-2-yl)thio)propionate (649 mg, yield 25%) as a colorless oil. $^1$H NMR (300 MHz, CDCl$_3$): δ 7.32 (s, 2H), 5.36 (s, 1H), 4.15 (q, 2H, J=3 Hz), 3.03 (t, 2H, J=6 Hz), 2.76 (d, 2H, J=6 Hz), 1.52 (s, 6H), 1.42 (s, 18H), 1.27 (t, 3H, J=6 Hz). LC-MS: 413 [M+H]$^+$. HPLC: 98.8% at 242 nm, $t_R$=4.33 min.

Example 4: 3-((2-((3,5-di-tert-butyl-4-hydroxyphenyl)thio)propan-2-yl)thio)propanoic acid

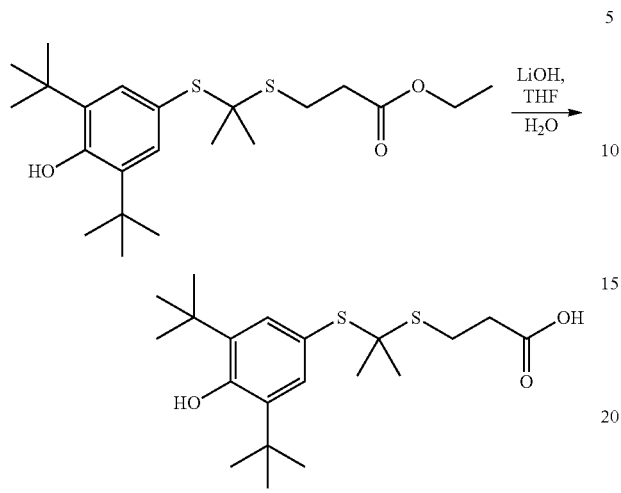

At 0° C., water and lithium hydroxide (218 mg, 5.2 mmol) were added to ethyl 2-((2-((3,5-di-tert-butyl-4-hydroxyphenyl)thio)propan-2-yl)thio)acetate (200 mg, 0.52 mmol) in THF (5 mL). The reaction solution was stirred at room temperature overnight, and then EtOAc (50 mL) and 1N HCl (5 mL) were added successively. The organic phase was separated out, washed with saturated salt water and dried with anhydrous sodium sulfate. The crude product was passed through a chromatography column (silica gel, 200 to 300 mesh, EtOAc:PE=1:1 to 3:1) to obtain the product 3-((2-((3,5-di-tert-butyl-4-hydroxyphenyl)thio)propan-2-yl)thio)propanoic acid (120 mg, yield 62%) as a yellow solid. $^1$H NMR (300 MHz, CDCl$_3$): δ 7.32 (s, 2H), 5.36 (s, 1H), 3.06 (t, 2H, J=6 Hz), 2.73 (d, 2H, J=6 Hz), 1.54 (s, 6H), 1.44 (s, 18H). LC-MS: 385 [M+H]$^+$. HPLC: 99.5% at 242 nm, $t_R$=3.61 min.

Example 5: 4,4'-disulfanediyl-bis(2-(tert-butyl)-6-(1-hydroxyethyl)phenol)

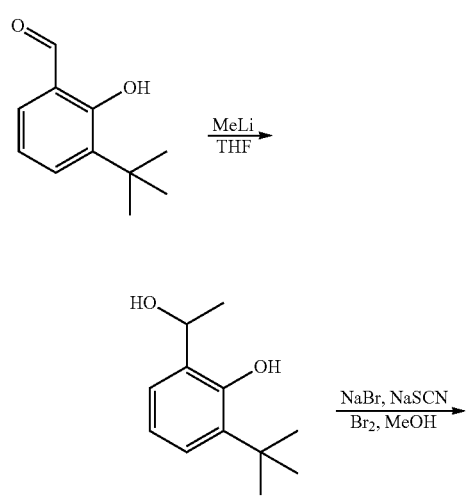

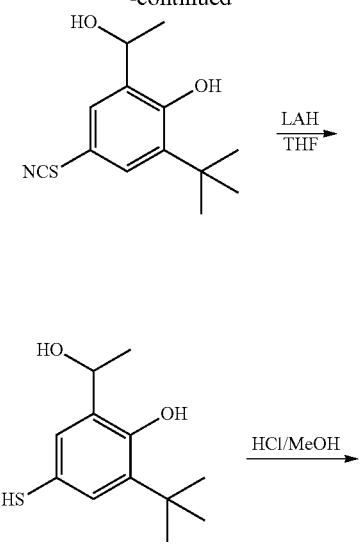

Step 1: 2-(tert-butyl)-6-(1-hydroxyethyl)phenol

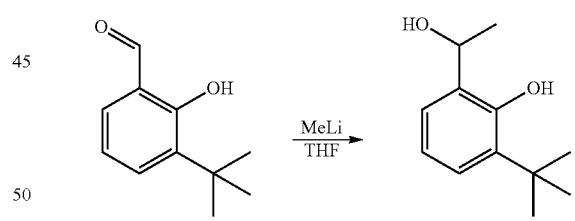

3-(tert-butyl)-2-hydroxybenzaldehyde (1.0 g, 11.2 mmol) was added to a three-necked flask containing dry THF (10 mL) under the protection of N$_2$. The above mixture was cooled below −10° C. with a dry ice-acetone bath, then MeLi (10.5 mL, 33.7 mmol, 1.6 M solution in THF) was slowly added dropwise to the above solution, and the reaction was monitored by TLC. After the reaction was completed, the temperature was gradually raised to room temperature. The reaction solution was poured into H$_2$O (50 mL), and the pH was adjusted to about 6 with 2N HCl, and then EtOAc (100 mL) was added. The organic phase was separated out, and dried with anhydrous sodium sulfate. After concentration, a crude product was obtained as a yellow oil, which was used directly in the next step.

Step 2: 2-(tert-butyl)-6-(1-hydroxyethyl)-4-thiocyanatophenol

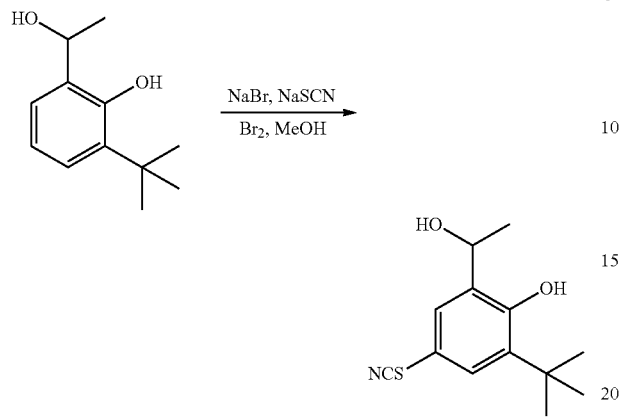

2-(tert-butyl)-6-(1-hydroxyethyl)phenol (1.0 g, 5.1 mmol), NaBr (0.52 g, 5.1 mmol) and NaSCN (1.6 g, 20 mmol) were added to a three-necked flask containing MeOH (10 mL). The above mixture was cooled with an ice water bath, and the temperature was kept at 0 to 5° C. Then the solution of $Br_2$ (0.30 mL, 5.7 mmol) in MeOH (5 mL) was slowly added dropwise to the above mixture, the temperature was controlled not to exceed 5° C. After the dropwise addition was finished, the resulting mixture was naturally raised to room temperature under stirring, and the reaction was monitored by TLC. The methanol was removed by concentration under reduced pressure. To the residue was added $H_2O$ (40 mL), and the resultant was extracted with EtOAc (100 mL×2), and dried with $Na_2SO_4$. The EtOAc was removed by concentration under reduced pressure. The crude product was passed through a chromatography column (silica gel, 200 to 300 mesh, PE:EA=10:1) to obtain the product as a light yellow oil (0.54 g, yield 42%). $^1$H NMR (300 MHz, $CDCl_3$): δ 8.90 (s, 2H), 7.34 (d, 1H, J=3 Hz), 7.07 (d, 1H, J=3 Hz), 5.06 (q, 1H, J=6 Hz), 1.61 (d, 3H, J=6 Hz), 1.61 (d, 3H, J=6 Hz), 1.40 (s, 9H). LC-MS: 252 $[M+H]^+$.

Step 3: 2-(tert-butyl)-6-(1-hydroxyethyl)-4-mercaptophenol

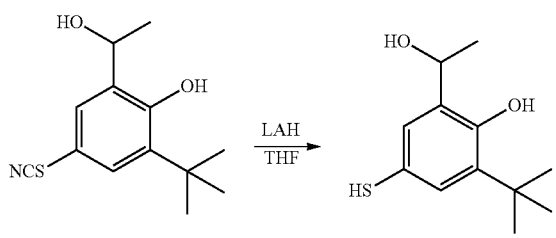

At 0° C., a solution of 2-(tert-butyl)-6-(1-hydroxyethyl)-4-thiocyanatophenol (300 mg, 1.2 mmol) in dry THF (6 mL) was slowly added dropwise to a suspension of lithium aluminum hydride (114 mg, 3.0 mmol) in THF (3 mL). The reaction was carried out at 0° C. for 5 hours. The reaction was quenched by slowly adding EtOAc (20 mL), and then 3N HCl (3 mL) and EtOAc (100 mL) were added. The organic phase was separated out, washed with saturated $NaHCO_3$ and saturated salt water, respectively, and dried with anhydrous sodium sulfate. After concentration, a crude product was obtained (187 mg, yield 69%).

Step 4: 4,4'-disulfanediyl-bis(2-(tert-butyl)-6-(1-hydroxyethyl)phenol)

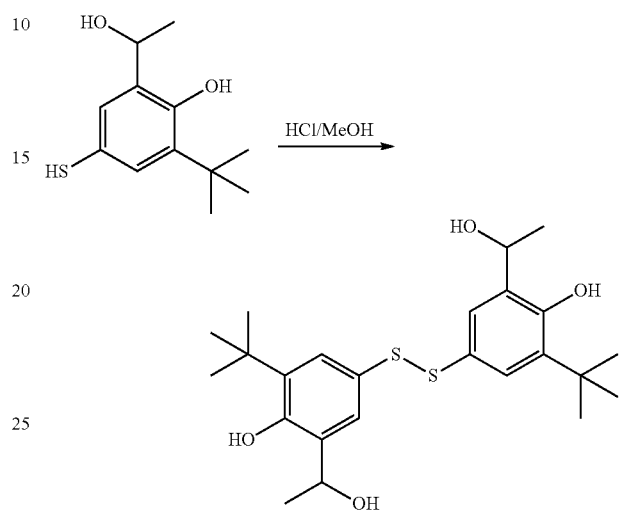

Under the protection of $N_2$, 2-(tert-butyl)-6-(1-hydroxyethyl)-4-mercaptophenol (187 mg, 0.75 mmol) was dissolved in MeOH (10 mL), and then concentrated hydrochloric acid (0.5 mL) was added dropwise at room temperature. The reaction was carried out at 70° C. for 3 hours under stirring, and the reaction was monitored by TLC. After cooling to room temperature, a yellow solid slowly precipitated and was filtered. The filter cake was washed with a small amount of cold MeOH to obtain a light yellow solid 4,4'-disulfanediyl-bis(2-(tert-butyl)-6-(1-hydroxyethyl)phenol) (111 mg, yield 58%). $^1$H NMR (300 MHz, $CDCl_3$): δ 8.41 (s, 2H), 7.30 (s, 2H), 7.00 (s, 2H), 4.42 (q, 2H, J=6 Hz), 1.51 (d, 6H, J=6 Hz), 1.35 (s, 18H). HPLC: 97.2% at 242 nm, $t_R$=9.03 min.

Example 6: 2,6-di-tert-butyl-4-((3-(tert-butyl)-4-hydroxy-5-(4-hydroxy-2-methylbutan-2-yl)phenyl)disulfanediyl)phenol

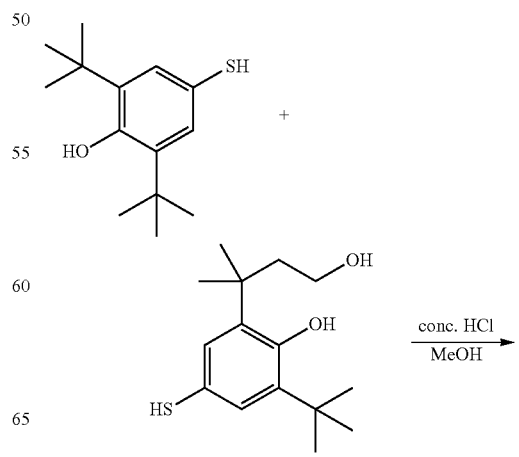

-continued

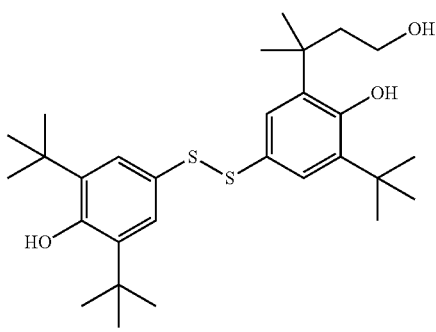 [SMILES: CC(C)(C)c1cc(SSc2cc(C(C)(C)C)c(O)c(C(C)(C)CCO)c2)cc(C(C)(C)C)c1O]

2,6-di-tert-butyl-4-mercaptophenol (400 mg, 1.68 mmol) and 2-(tert-butyl)-6-(4-hydroxy-2-methylbutan-2-yl)-4-mercaptophenol (300 mg, 1.20 mmol) were added to MeOH (20 mL), and then concentrated hydrochloric acid (0.5 mL) was added dropwise at room temperature. The resulting reaction solution was stirred at 70° C. for 3 h, and the reaction was monitored by TLC. After cooling to room temperature, MeOH was removed by concentration under reduced pressure. To the residue was added $H_2O$ (10 mL) and EtOAc (50 mL), and the resultant was dried with $Na_2SO_4$. The crude product was purified by chromatography column (silica gel, 200 to 300 mesh, EtOAc:PE=1:50 to 1:10) to obtain 2,6-di-tert-butyl-4-((3-(tert-butyl)-4-hydroxy-5-(4-hydroxy-2-methylbutan-2-yl)phenyl)disulfanediyl)phenol (31 mg, yield 4%). 1H NMR (300 MHz, $CDCl_3$): δ 8.23 (s, 2H), 7.90 (s, 2H), 3.48 (t, 2H, J=6 Hz), 2.26 (t, 2H, J=6 Hz), 1.45 (s, 9H) 1.41 (s, 6H), 1.35 (s, 18H). HPLC: 93.5% at 242 nm, $t_R$=6.04 min.

Example 7: 4,4'-(propane-2,2-diylbis(thio))bis(2-methoxyphenol)

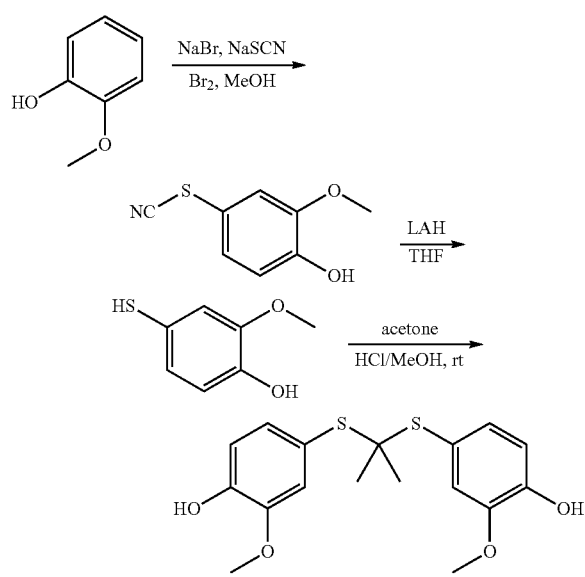

Step 1: 2-methoxy-4-thiocyanatophenol

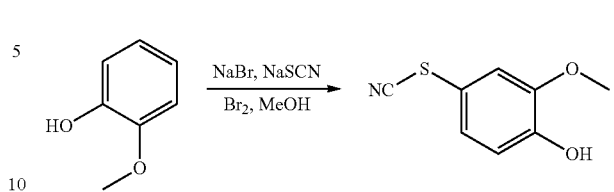

2-methoxyphenol (3.7 g, 30.0 mmol), NaBr (3.1 g, 30.0 mmol) and NaSCN (4.9 g, 60.0 mmol) were added to a three-necked flask containing MeOH (37 mL). The above mixture was cooled with an ice water bath, and the temperature was kept at 0 to 5° C. Then the solution of $Br_2$ (1.7 mL, 33.0 mmol) in MeOH (19 mL) was slowly added dropwise to the above mixture, and the temperature was controlled not to exceed 5° C. After the dropwise addition, the resulting mixture was naturally raised to room temperature under stirring, and the reaction was monitored by TLC. The methanol was removed by concentration under reduced pressure. To the residue was added $H_2O$ (40 mL), and the resultant was extracted with EtOAc (100 mL×2), and dried with $Na_2SO_4$. The EtOAc was removed by concentration under reduced pressure to obtain a light yellow solid. A small amount of PE was added to the obtained solid, stirred and washed, and filtered to obtain a light yellow solid.

Step 2: 2-methoxy-4-mercaptophenol

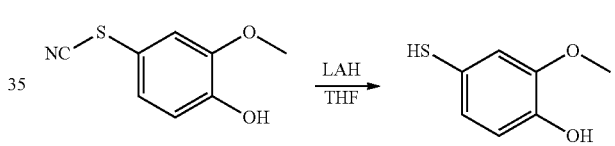

At 0° C., a solution of 2-methoxy-4-thiocyanatophenol (1.0 g, 5.5 mmol) in dry THF (15 mL) was slowly added dropwise to a suspension of lithium aluminum hydride (0.34 g, 8.3 mmol) in THF (10 mL). The reaction was carried out at 0° C. for 5 hours. The reaction was quenched by slowly adding $H_2O$ (20 mL), and then 3N HCl (3 mL) and EtOAc (100 mL) were added. The organic phase was separated out, washed with saturated $NaHCO_3$ and saturated salt water, respectively, and dried with anhydrous sodium sulfate. After concentration, the crude product was used directly in the next step.

Step 3: 4,4'-(propane-2,2-diylbis(thio))bis(2-methoxyphenol)

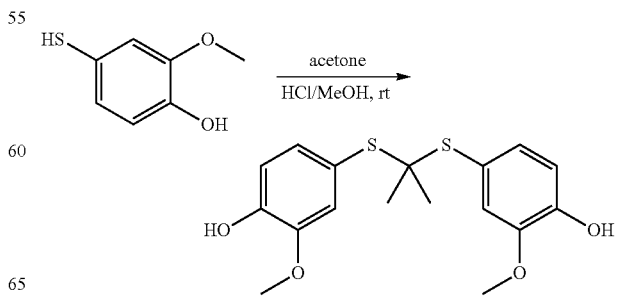

Under the protection of N$_2$, 2-methoxy-4-mercaptophenol (400 mg, 2.6 mmol) and acetone (2 mL) were added to MeOH (8 mL), and then HCl gas was slowly introduced to adjust pH to 2 to 3. The resulting solution was reacted overnight at room temperature, and the reaction was monitored by TLC. The methanol was removed by concentration under reduced pressure. To the residue was added H$_2$O (40 mL), and the resultant was extracted with EtOAc (100 mL×2), and dried with Na$_2$SO$_4$. The EtOAc was removed by concentration under reduced pressure. The crude product was passed through a chromatography column (silica gel, 200 to 300 mesh, PE:EA=10:1) to obtain a light yellow solid (85 mg, yield 37%). $^1$H NMR (300 MHz, CDCl$_3$): δ 7.03~6.96 (m, 4H), 6.79 (d, 2H, J=3 Hz), 3.75 (s, 6H), 1.38 (s, 6H).

Example 8: 2,6-di-tert-butyl-4-((2-((3-(tert-butyl)-4-hydroxy-5-(4-hydroxy-2-methylbutan-2-yl)phenyl)thio)propan-2-yl)thio)phenol

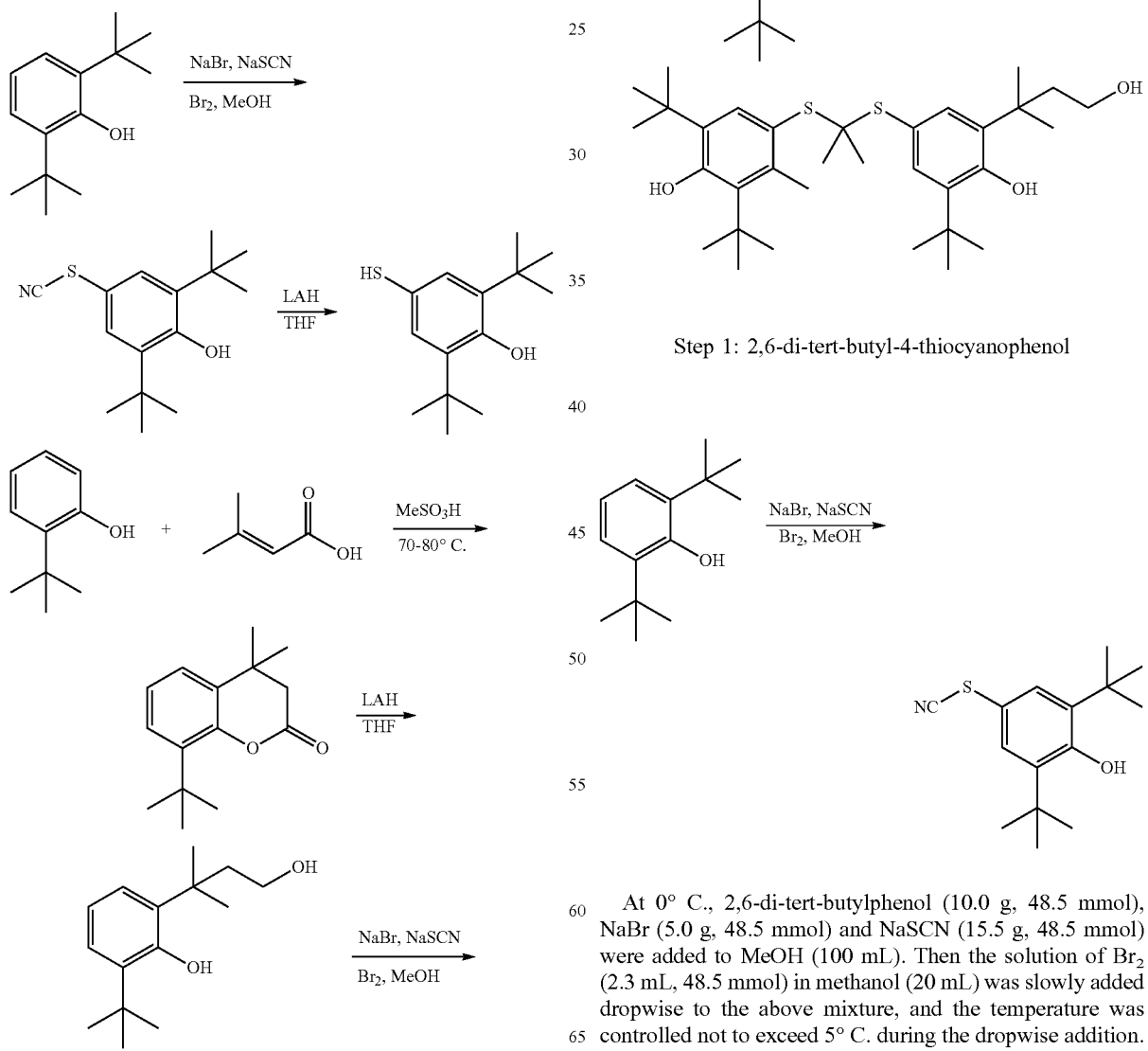

Step 1: 2,6-di-tert-butyl-4-thiocyanophenol

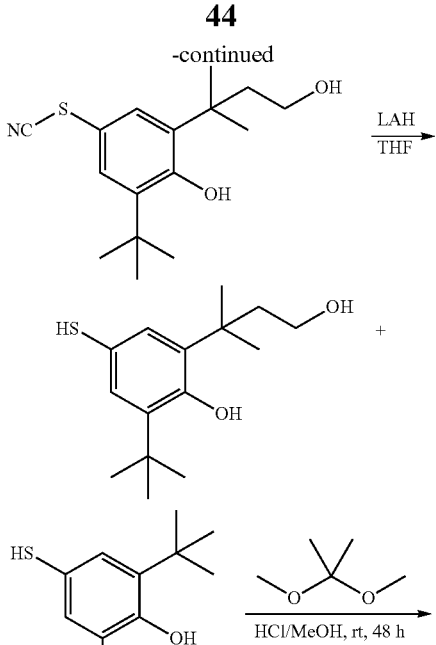

At 0° C., 2,6-di-tert-butylphenol (10.0 g, 48.5 mmol), NaBr (5.0 g, 48.5 mmol) and NaSCN (15.5 g, 48.5 mmol) were added to MeOH (100 mL). Then the solution of Br$_2$ (2.3 mL, 48.5 mmol) in methanol (20 mL) was slowly added dropwise to the above mixture, and the temperature was controlled not to exceed 5° C. during the dropwise addition. After the dropwise addition was finished, the resulting mixture was naturally raised to room temperature and reacted for 3 hours. The MeOH was removed by concentration under reduced pressure. To the residue was added EtOAc (40 mL), and the resultant was washed with saturated salt water, and dried with Na₂SO₄. The resulting crude product 2,6-di-tert-butyl-4-thiocyanophenol was directly used in the next step.

Step 2: 2,6-di(tert-butyl)-4-mercaptophenol

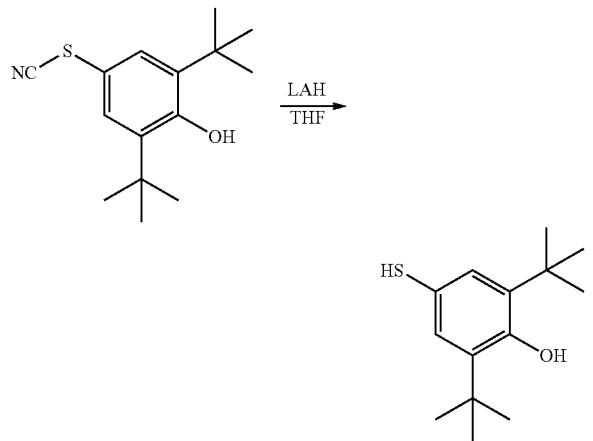

At 0° C., a solution of 8-(tert-butyl)-4,4-dimethylchroman-2-one (7.0 g, 0.03 mol) in dry THF (10 mL) was slowly added dropwise to a suspension of lithium aluminum hydride (2.3 g, 0.06 mmol) in THF (50 mL). The reaction was carried out at 0° C. for 3 hours. The reaction was quenched by adding EtOAc (20 mL), and then 3N HCl (50 mL) and EtOAc (200 mL) were added. The organic phase was washed with saturated NaHCO₃ and saturated salt water respectively, and dried with anhydrous sodium sulfate. After removing the organic solvent under reduced pressure, 2-(tert-butyl)-6-(4-hydroxy-2-methylbutan-2-yl)phenol (7.1 g, crude yield 99.7%) was obtained as a yellow oil.

Step 3: 8-(tert-butyl)-4,4-dimethylchroman-2-one

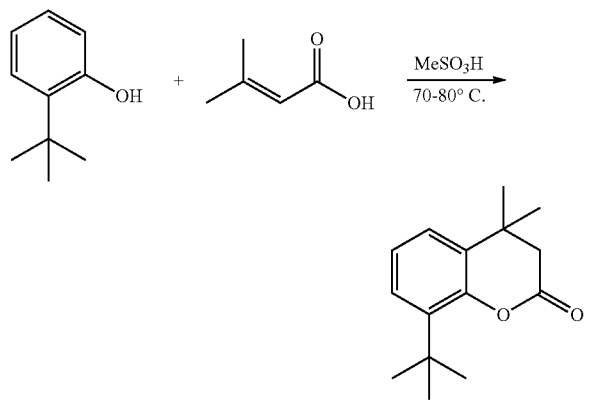

To MeSO₃H (150 mL) were added o-tert-butylphenol (15.0 g, 0.10 mol) and 3-methylbutenoic acid (11 g, 0.11 mol), and then the mixture was heated to 70 to 80° C. and reacted for 3 hours. After the temperature was cooled to room temperature, the reaction solution was poured into ice water and extracted with EtOAc (200 mL). The organic phase was washed with saturated NaHCO₃ aqueous solution and saturated salt water, respectively, and dried with anhydrous sodium sulfate. After removing the organic solvent under reduced pressure, 8-(tert-butyl)-4,4-dimethylchroman-2-one (24.6 g, crude yield 106%), a yellow oil, was obtained and slowly solidified at room temperature. ¹H NMR (300 MHz, CDCl₃): δ 7.33~7.29 (br, 2H), 7.01 (d, 1H, J=8 Hz), 2.65 (s, 2H), 1.39 (s, 6H), 1.35 (s, 9H).

Step 4: 2-(tert-butyl)-6-(4-hydroxy-2-methylbutan-2-yl) phenol

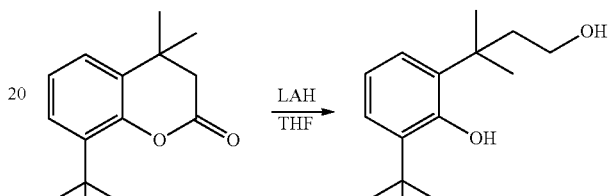

Under nitrogen protection, a solution of 8-(tert-butyl)-4,4-dimethylchroman-2-one (7.0 g, 0.03 mol) in dry THF (10 mL) was slowly added dropwise to a suspension of lithium aluminum hydride (2.3 g, 0.06 mmol) in THF (50 mL) at 0° C. The reaction was carried out at 0° C. for 3 hours. The reaction was quenched by adding EtOAc (20 mL), and then 3N HCl (50 mL) and EtOAc (200 mL) were added. The organic phase was washed with saturated NaHCO₃ and saturated salt water respectively, and dried with anhydrous sodium sulfate. After removing the organic solvent under reduced pressure, 2-(tert-butyl)-6-(4-hydroxy-2-methylbutan-2-yl)phenol (7.1 g, crude yield 99.7%) was obtained as a yellow oil. ¹H NMR (300 MHz, CDCl₃): δ 7.23 (d, 1H), 7.10 (dd, 1H, J=8 Hz), 6.60 (d, 1H, J=8 Hz), 3.55 (t, 2H, J=8 Hz), 2.21 (t, 2H, J=8 Hz), 1.45 (s, 6H), 1.31 (s, 9H).

Step 5: 2-(tert-butyl)-6-(4-hydroxy-2-methylbutan-2-yl)-4-thiocyanophenol

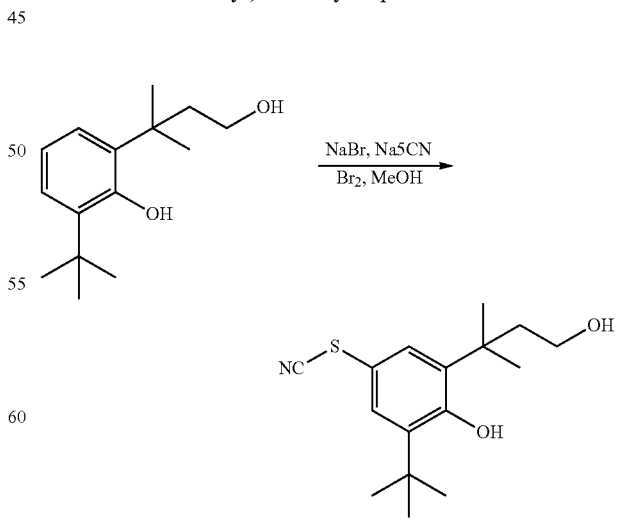

At 0° C., 2-(tert-butyl)-6-(4-hydroxy-2-methylbutan-2-yl) phenol (5.0 g, 21.2 mmol), NaBr (2.2 g, 21.2 mmol) and NaSCN (6.87 g, 84.8 mmol) were added to MeOH (50 mL), and a solution of Br$_2$ (1.0 mL, 21.2 mmol) in methanol (10 mL) was slowly added thereto under stirring. After the dropwise addition was finished, the reaction was carried out at room temperature for 3 hours. The MeOH was removed by concentration under reduced pressure. To the residue was added EtOAc (200 mL), and the resultant was washed with saturated salt water, and dried with Na$_2$SO$_4$. The resulting crude product was directly used in the next step.

Step 6: 3-(3-(tert-butyl)-5-mercapto-2-hydroxyphenyl)-3-methylbutan-1-ol

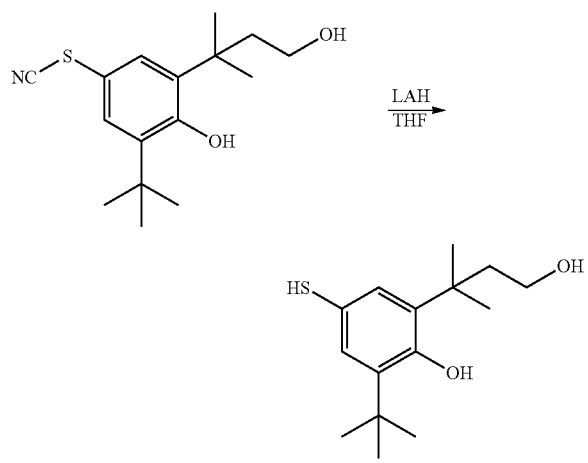

At 0° C., a solution of 2-(tert-butyl)-6-(4-hydroxy-2-methylbutan-2-yl)-4-thiocyanophenol (1.38 g, 4.7 mmol) in dry THF (10 mL) was slowly added dropwise to a suspension of lithium aluminum hydride (0.36 g, 9.47 mmol) in THF (50 mL). The reaction was carried out at 0° C. for 5 hours. The reaction was quenched by adding EtOAc (10 mL), and then 3N HCl (20 mL) and EtOAc (100 mL) were added. The organic phase was washed with saturated NaHCO$_3$ and saturated salt water, respectively, and dried with anhydrous sodium sulfate. The crude product was passed through a chromatography column (silica gel, EtOAc:PE=1:5 to 1:2) to obtain the product 3-(3-(tert-butyl)-5-mercapto-2-hydroxyphenyl)-3-methylbutan-1-ol (350 mg, yield 28%) as a yellow adhesion.

Step 7: 2,6-di-tert-butyl-4-((2-((3-(tert-butyl)-4-hydroxy-5-(4-hydroxy-2-methylbutan-2-yl)phenyl)thio)propan-2-yl)thio)phenol

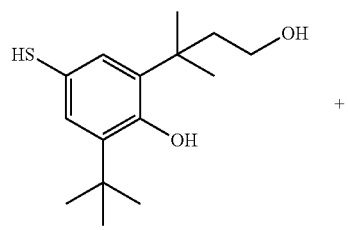

+

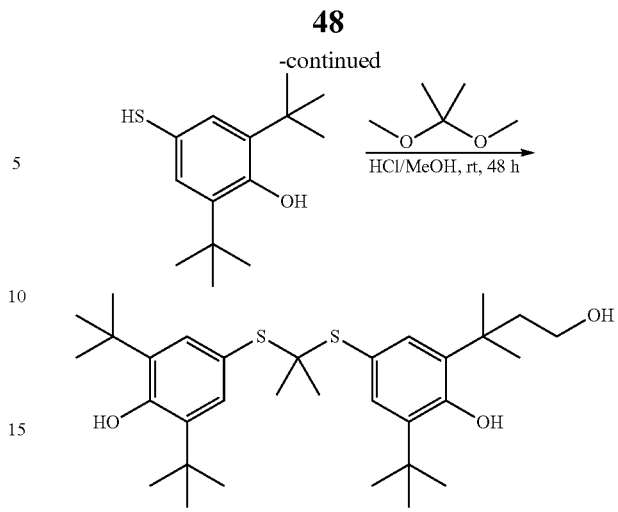

Under the protection of N$_2$, 3-(3-(tert-butyl)-5-mercapto-2-hydroxyphenyl)-3-methylbutan-1-ol (400 mg, 1.5 mmol), 2,2-dimethoxypropane (2 mL) were added to MeOH (8 mL), and then HCl gas was slowly introduced to adjust pH to 2 to 3. The resulting solution was reacted overnight at room temperature, and the reaction was monitored by TLC. The methanol was removed by concentration under reduced pressure. To the residue was added H$_2$O (40 mL), the resultant was extracted with EtOAc (100 mL×2), and dried with Na$_2$SO$_4$. The crude product was passed through a chromatography column (silica gel, EtOAc:PE=1:20 to 1:5) to obtain the product 2,6-di-tert-butyl-4-((2-((3-(tert-butyl)-4-hydroxy-5-(4-hydroxy-2-methylbutan-2-yl)phenyl)thio)propan-2-yl)thio)phenol (154 mg, yield 19%) as a colorless oil, which slowly turns into a white solid at room temperature. $^1$H NMR (300 MHz, CDCl$_3$): δ 7.49 (m, 2H), 7.42 (s, 1H), 7.28 (m, 2H), 7.18 (s, 2H), 5.46 (s, 1H), 3.45 (t, 2H, J=6 Hz), 2.16 (t, 2H, J=6 Hz), 1.48 (s, 18H), 1.46 (s, 6H), 1.41 (s, 6H), 1.27 (s, 9H). HPLC: 94.0% at 242 nm, t$_R$=8 min.

Example 9: 4,4'-(propane-2,2-diylbis(thio))bis(2-(tert-butyl)-6-(4-hydroxy-2-methylbutan-2-yl)phenol)

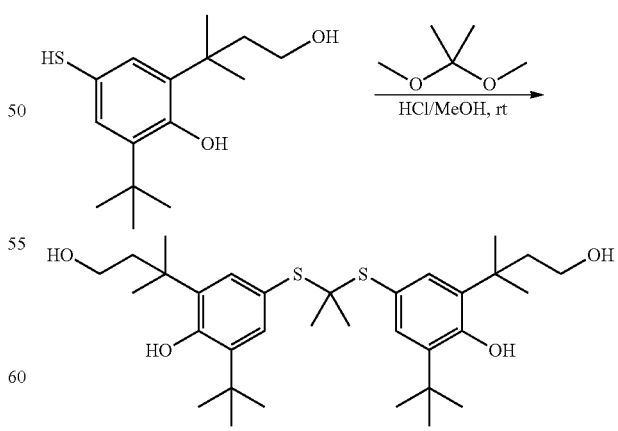

Under the protection of N$_2$, at 0° C., 3-(3-(tert-butyl)-5-mercapto-2-hydroxyphenyl)-3-methylbutan-1-ol (100 mg, 0.183 mmol) and 2,2-dimethoxypropane (1 mL) were added to MeOH (5 mL), and then HCl gas was slowly introduced to adjust pH to 2 to 3. The resulting solution was reacted overnight at room temperature, and the reaction was monitored by TLC. The methanol was removed by concentration under reduced pressure. To the residue was added $H_2O$ (40 mL), the resultant was extracted with EtOAc (100 mL×2), and dried with $Na_2SO_4$. The crude product was passed through a chromatography column (silica gel, EtOAc:PE=1:20 to 1:5) to obtain the product 4,4'-(propane-2,2-diylbis(thio))bis(2-(tert-butyl)-6-(4-hydroxy-2-methylbutan-2-yl)phenol) (54 mg, yield 50%) as a colorless oil, which slowly turns into a white solid at room temperature. $^1$H NMR (300 MHz, $CDCl_3$): δ 7.32 (s, 4H), 5.36 (s, 1H), 3.04 (t, 2H, J=6 Hz), 2.73 (t, 2H, J=6 Hz), 1.54 (s, 6H), 1.44 (s, 30H). HPLC: 95.3% at 242 nm, $t_R$=7.53 min.

Example 10: 2,6-di-tert-butyl-4-((2-((8-(tert-butyl)-4,4-dimethylchroman-6-yl)thio)propan-2-yl)thio)phenol

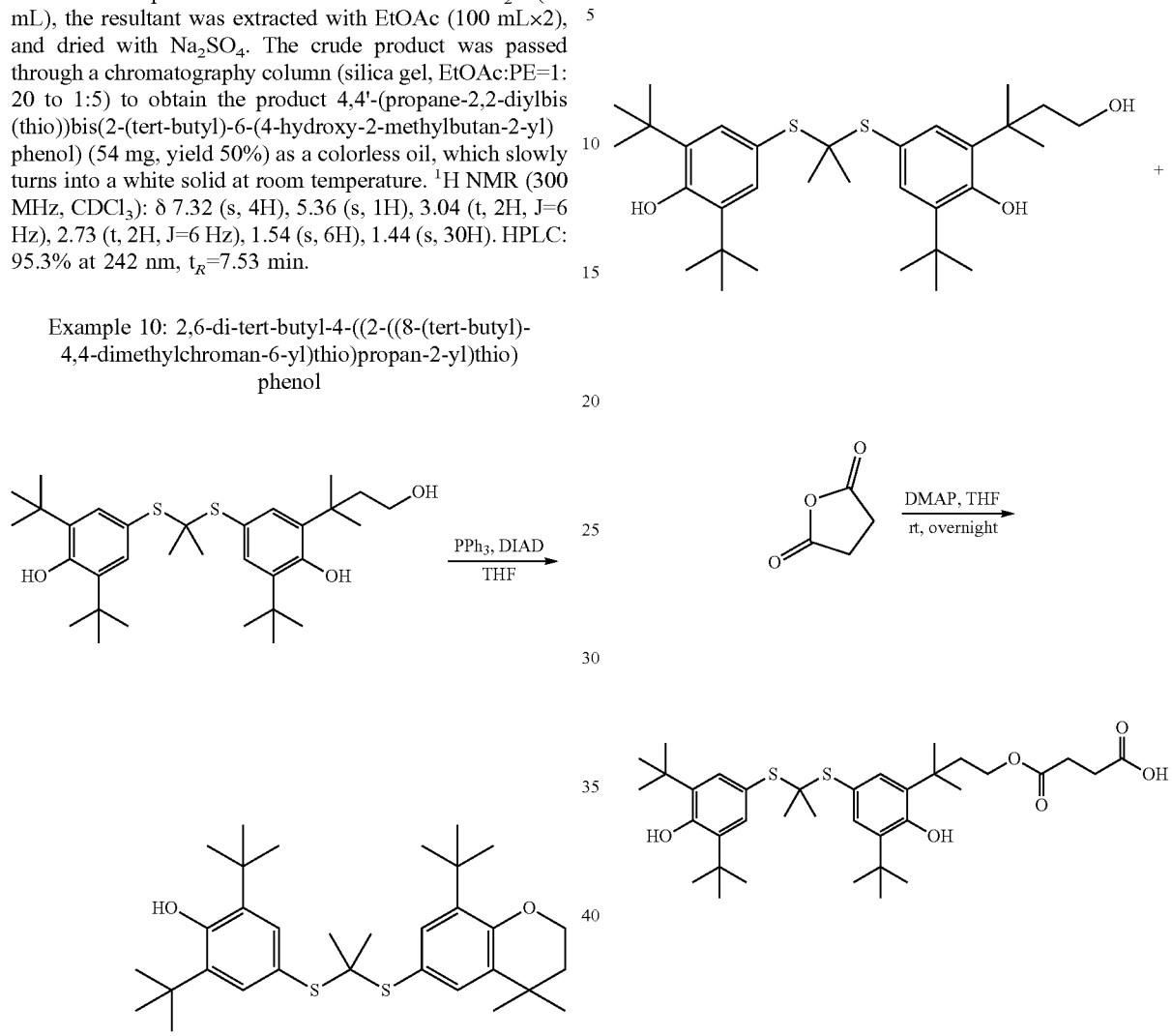

At 0° C., 2,6-di-tert-butyl-4-((2-((3-(tert-butyl)-4-hydroxy-5-(4-hydroxy-2-methylbutan-2-yl)phenyl)thio)propan-2-yl)thio)phenol (100 mg, 0.183 mmol), $PPh_3$ (76 mg, 0.274 mmol) and phthalamide (40 mg, 0.274 mmol) were added to dry THF (10 mL). Then the solution of DIAD (74 mg, 0.366 mmol) in THF (2 mL) was slowly added dropwise to the above mixture. The reaction was carried out at 0° C. for 2 hours. The organic solvent was removed by concentration under reduced pressure. To the residue was added EtOAc (20 mL), and the resultant was washed with saturated salt water, and dried with $Na_2SO_4$. The crude product was passed through a chromatography column (silica gel, EtOAc:PE=1:50 to 1:20) to obtain the product 2,6-di-tert-butyl-4-((2-((8-(tert-butyl)-4,4-dimethylchroman-6-yl)thio)propan-2-yl)thio)phenol (54 mg, yield 56%) as a white foam. $^1$H NMR (300 MHz, $CDCl_3$): δ 7.32 (s, 4H), 5.36 (s, 1H), 3.04 (t, 2H, J=6 Hz), 2.73 (t, 2H, J=6 Hz), 1.54 (s, 6H), 1.44 (s, 30H). HPLC: 95.3% at 242 nm, $t_R$=7.53 min.

Example 11: 4-(3-(3-(tert-butyl)-5-((2-((3,5-di-tert-butyl-4-hydroxyphenyl)thio)propan-2-yl)thio)-2-hydroxyphenyl)-3-methylbutoxy)-4-oxobutanoic acid At 0° C., 2,6-di-tert-butyl-4-((2-((3-(tert-butyl)-4-hydroxy-5-(4-hydroxy-2-methylbutan-2-yl)phenyl)thio)propan-2-yl)thio)phenol (2.3 g, 4.21 mmol), succinic anhydride (2.1 g, 21.06 mmol) and DMAP (0.51 g, 4.21 mmol) were added to THF (50 mL). The resulting mixture was stirred at room temperature, and the reaction was monitored by TLC. The organic solvent was removed by concentration under reduced pressure. To the residue was added EtOAc (20 mL), and the resultant was washed with 1N HCl, saturated salt water and saturated $NaHCO_3$ aqueous solution, respectively, and dried with anhydrous sodium sulfate. The crude product was passed through a chromatography column (silica gel, EtOAc:PE=1:100 to 1:50) to obtain the product 4-(3-(3-(tert-butyl)-5-((2-((3,5-di-tert-butyl-4-hydroxyphenyl)thio)propan-2-yl)thio)-2-hydroxyphenyl)-3-methylbutoxy)-4-oxobutanoic acid (2.5 g, yield 92%) as a white foam. $^1$H NMR (300 MHz, $CDCl_3$): δ 7.40 (s, 1H), 7.32 (m, 2H), 7.21 (s, 1H), 4.00 (t, 2H, J=6 Hz), 2.34~2.27 (m, 4H), 1.97 (t, 2H, J=6 Hz), 1.54~1.38 (39H). HPLC: 91.6% at 242 nm, $t_R$=7.12 min.

Example 12: 3-(3-(tert-butyl)-5-((2-((3,5-di-tert-butyl-4-hydroxyphenyl)thio)propan-2-yl)thio)-2-hydroxyphenyl)-3-methylbutyl 5-(1,2-dithiolan-3-yl)pentanoate

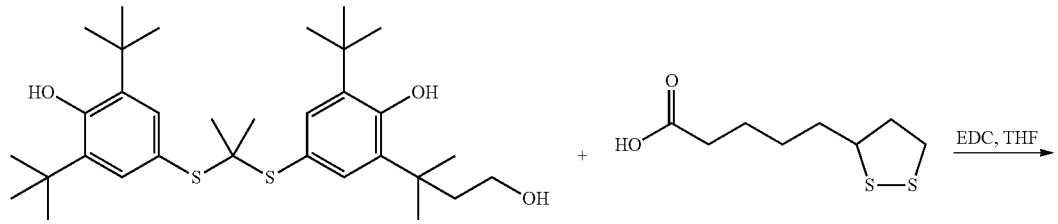

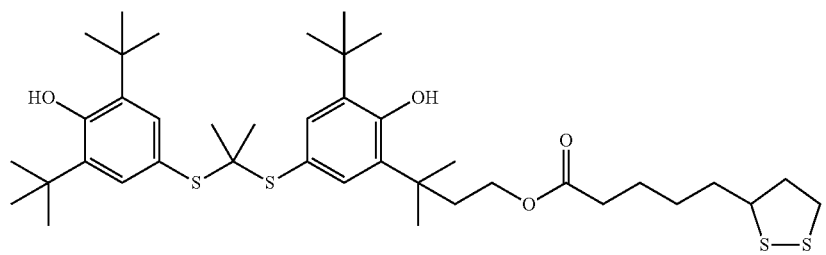

At room temperature, 2,6-di-tert-butyl-4-((2-((3-(tert-butyl)-4-hydroxy-5-(4-hydroxy-2-methylbutan-2-yl)phenyl)thio)propan-2-yl)thio)phenol (300 mg, 0.55 mmol), lipoic acid (113 mg, 0.55 mmol) and EDC hydrochloride (126 mg, 0.66 mmol) were added to THF (20 mL), and the reaction solution was stirred overnight at room temperature. The organic solvent was removed by concentration under reduced pressure. To the residue was added EtOAc (50 mL) and saturated salt water (10 mL), respectively. The organic phase was washed with saturated salt water and dried with anhydrous sodium sulfate. The crude product was passed through a chromatography column (silica gel, EtOAc:PE=1: 50 to 1:20) to obtain the product 3-(3-(tert-butyl)-5-((2-((3, 5-di-tert-butyl-4-hydroxyphenyl)thio)propan-2-yl)thio)-2-hydroxyphenyl)-3-methylbutyl 5-(1,2-dithiolan-3-yl) pentanoate (110 mg, yield 27%) as a white solid. $^1$H NMR (300 MHz, CDCl$_3$): δ 7.98 (s, 1H), 7.42 (s, 1H), 7.34 (m, 2H), 7.23 (s, 1H), 3.75 (t, 2H, J=6 Hz), 3.15~3.11 (m, 2H), 2.41~2.36 (m, 2H), 2.37~2.05 (m, 6H), 1.65~1.62 (m, 1H), 1.58~1.54 (m, 4H), 1.39~1.25 (m, 30H), 1.17 (s, 9H). HPLC: 90.5% at 242 nm, $t_R$=16.59 min.

Example 13: 3-(3-(tert-butyl)-5-((2-((3,5-di-tert-butyl-4-hydroxyphenyl)thio)propan-2-yl)thio)-2-hydroxyphenyl)-3-methylbutyl 2-acetoxybenzoate

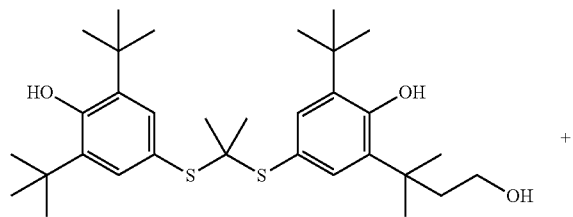

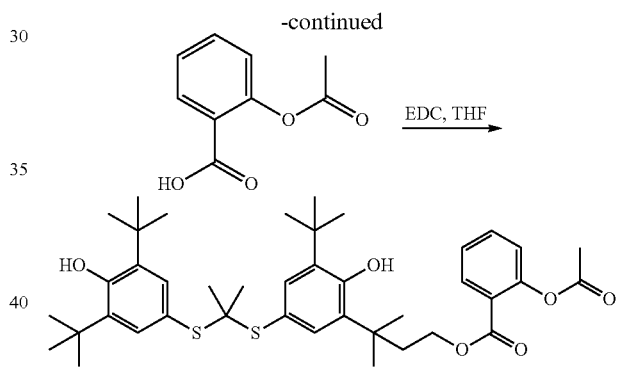

At room temperature, 2,6-di-tert-butyl-4-((2-((3-(tert-butyl)-4-hydroxy-5-(4-hydroxy-2-methylbutan-2-yl)phenyl)thio)propan-2-yl)thio)phenol (700 mg, 1.28 mmol), 2-acetoxybenzoic acid (460 mg, 2.56 mmol) and EDC hydrochloride (126 mg, 0.66 mmol) were added to THF (20 mL), and the reaction solution was stirred overnight at room temperature. The organic solvent was removed by concentration under reduced pressure. To the residue was added EtOAc (50 mL) and saturated salt water (25 mL), respectively. The organic phase was washed with saturated salt water and dried with anhydrous sodium sulfate. The crude product was passed through a chromatography column (silica gel, 200 to 300 mesh, EtOAc:PE=1:40 to 1:15) to obtain the product 3-(3-(tert-butyl)-5-((2-((3,5-di-tert-butyl-4-hydroxyphenyl)thio)propan-2-yl)thio)-2-hydroxyphenyl)-3-methylbutyl 2-acetoxybenzoate (520 mg, yield 57%) as a white solid. $^1$H NMR (300 MHz, CDCl$_3$): δ 8.05 (s, 1H), 7.65~7.61 (m, 2H), 7.42 (s, 1H), 7.38~7.26 (m, 3H), 7.18 (d, 1H, J=6 Hz), 3.98 (t, 2H, J=6 Hz), 2.29 (t, 2H, J=6 Hz), 1.41 (s, 6H), 1.36 (s, 18H), 1.17 (s, 9H). HPLC: 88.5% at 242 nm, $t_R$=10.45 min.

Example 14: 3-(3-(tert-butyl)-5-((2-((3,5-di-tert-butyl-4-hydroxyphenyl)thio)propan-2-yl)thio)-2-hydroxyphenyl)-3-methylbutyl acetate

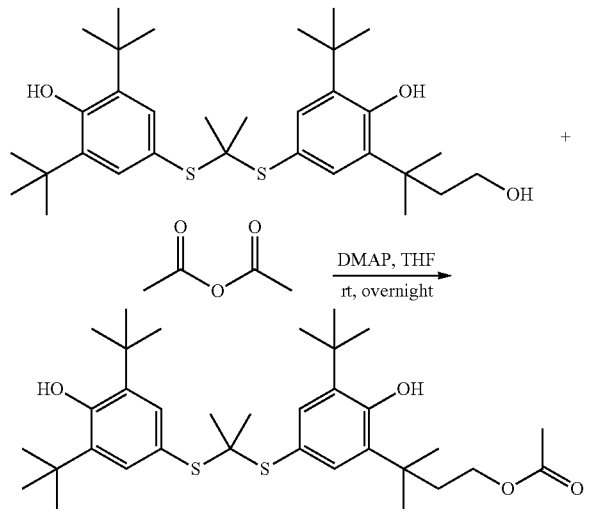

At room temperature, 2,6-di-tert-butyl-4-((2-((3-(tert-butyl)-4-hydroxy-5-(4-hydroxy-2-methylbutan-2-yl)phenyl)thio)propan-2-yl)thio)phenol (300 mg, 0.55 mmol), acetic anhydride (2 mL) and DMAP (50 mg, 0.41 mmol) were added to THF (20 mL), and the reaction solution was stirred overnight at room temperature. The organic solvent was removed by concentration under reduced pressure. To the residue was added EtOAc (100 mL) and saturated NaHCO$_3$ aqueous solution (25 mL), respectively. The organic phase was washed with saturated salt water and dried with anhydrous sodium sulfate. The crude product was passed through a chromatography column (silica gel, EtOAc:PE=1:15 to 1:5) to obtain the product 3-(3-(tert-butyl)-5-((2-((3,5-di-tert-butyl-4-hydroxyphenyl)thio)propan-2-yl)thio)-2-hydroxyphenyl)-3-methylbutyl acetate (240 mg, yield 74%) as a white solid. $^1$H NMR (300 MHz, CDCl$_3$): δ 8.13 (s, 1H), 8.45 (s, 1H), 7.38 (s, 1H), 7.32 (m, 2H), 3.91 (t, 2H, J=6 Hz), 2.99 (s, 3H), 2.27 (t, 2H, J=6 Hz), 1.38~1.24 (m, 33H), 1.20 (s, 9H). HPLC: 78.2% at 242 nm, t$_R$=21.95 min.

Example 15: (S)-3-(3-(tert-butyl)-5-((2-((3,5-di-tert-butyl-4-hydroxyphenyl)thio)propan-2-yl)thio)-2-hydroxyphenyl)-3-methylbutyl 2-(2-chlorophenyl)-2-(6,7-dihydrothieno[3,2-c]pyridin-5(4H)-yl)acetate

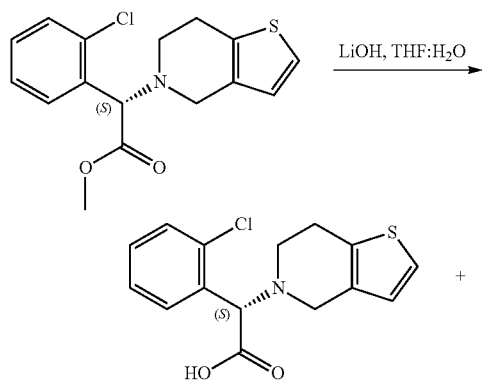

Step 1: (S)-(2-chlorophenyl)-2-(6,7-dihydrothiophene[3,2-c]pyridin-5(4H)-yl) acetic acid At room temperature, (S)-methyl 2-(2-chlorophenyl)-2-(6,7-dihydrothiophene[3,2-c]pyridin-5(4H)-yl)acetate (200 mg, 1.56 mmol) and lithium hydroxide hydrate (655 mg, 15.6 mmol) were added to the mixture of THF (20 mL) and water (5 mL), and the reaction solution was stirred overnight at room temperature. The organic solvent was removed by concentration under reduced pressure. To the residue was added EtOAc (50 mL), and then the pH was adjusted to 4 to 5 with 1N HCl. The organic phase was separated out, washed with saturated salt water (25 mL) and dried with anhydrous sodium sulfate. After removing the organic solvent, the crude product (S)-2-(2-chlorophenyl)-2-(6,7-dihydrothiophene[3,2-c]pyridin-5(4H)-yl) acetic acid (326 mg, yield 68%) was obtained as a light yellow solid.

Step 2: (S)-3-(3-(tert-butyl)-5-((2-((3,5-di-tert-butyl-4-hydroxyphenyl)thio)propan-2-yl)thio)-2-hydroxyphenyl)-3-methylbutyl 2-(2-chlorophenyl)-2-(6,7-dihydrothieno[3,2-c]pyridin-5(4H)-yl)acetate

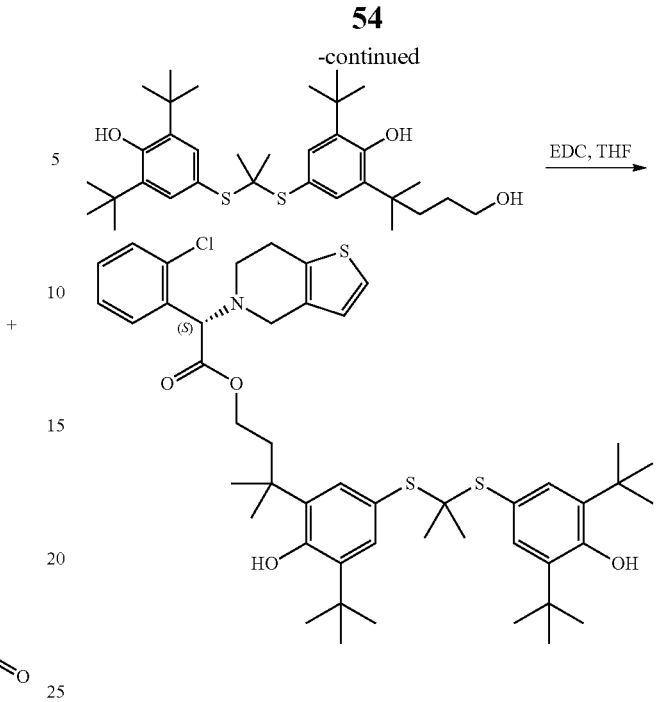

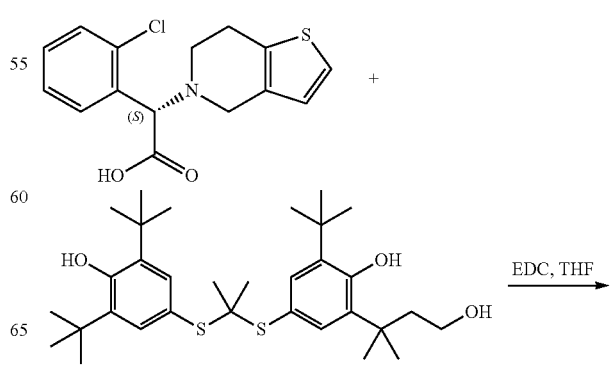

-continued

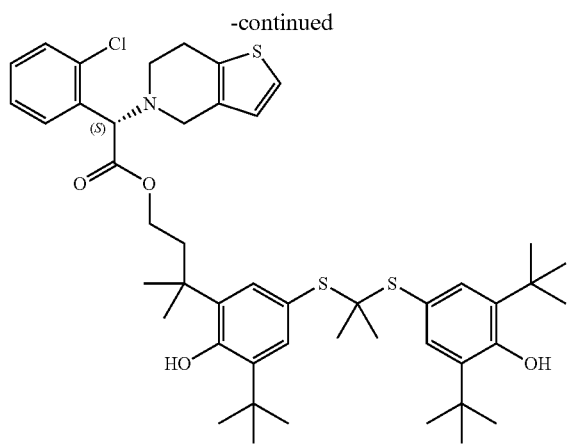

At room temperature, 2,6-di-tert-butyl-4-((2-((3-(tert-butyl)-4-hydroxy-5-(4-hydroxy-2-methylbutan-2-yl)phenyl)thio)propan-2-yl)thio)phenol (200 mg, 0.325 mmol), (S)-2-(2-chlorophenyl)-2-(6,7-dihydrothiophene[3,2-c]pyridin-5(4H)-yl)acetic acid (100 mg, 0.325 mmol) and EDC hydrochloride (75 mg, 0.39 mmol) were added to THF (20 mL). The reaction solution was stirred overnight at room temperature. The organic solvent was removed by concentration under reduced pressure. To the residue was added EtOAc (100 mL) and saturated salt water (25 mL), respectively. The organic phase was washed with saturated salt water and dried with anhydrous sodium sulfate. The crude product was passed through a chromatography column (silica gel, EtOAc:PE=1:40 to 1:25) to obtain the product (S)-3-(3-(tert-butyl)-5-((2-((3,5-di-tert-butyl-4-hydroxyphenyl)thio)propan-2-yl)thio)-2-hydroxyphenyl)-3-methylbutyl 2-(2-chlorophenyl)-2-(6,7-dihydrothieno[3,2-c]pyridin-5(4H)-yl)acetate (130 mg, yield 42%) as a white solid. $^1$H NMR (300 MHz, CDCl$_3$): δ 7.79 ((t, 2H, J=6 Hz), 7.62 (d, 2H, J=6 Hz), 7.61 (m, 2H), 7.49~7.43 (m, 3H), 7.18 (s, 1H), 5.46 (s, 2H), 5.27 (m, 2H), 4.41 (d, 2H, J=6 Hz), 4.25 (m, 2H), 3.98 (t, 2H, J=6 Hz), 3.85 (m, 2H), 2.26 (t, 2H, J=6 Hz), 1.49~1.42 (m, 30H), 0.88~0.82 (m, 2H), 1.29 (s, 9H). HPLC: 98.4% at 242 nm, $t_R$=21.91 min.

Example 16 2-(4-amino-2-methylbutan-2-yl)-6-(tert-butyl)-4-((2-((3,5-di-tert-butyl-4-hydroxyphenyl)thio)propan-2-yl)thio)phenol

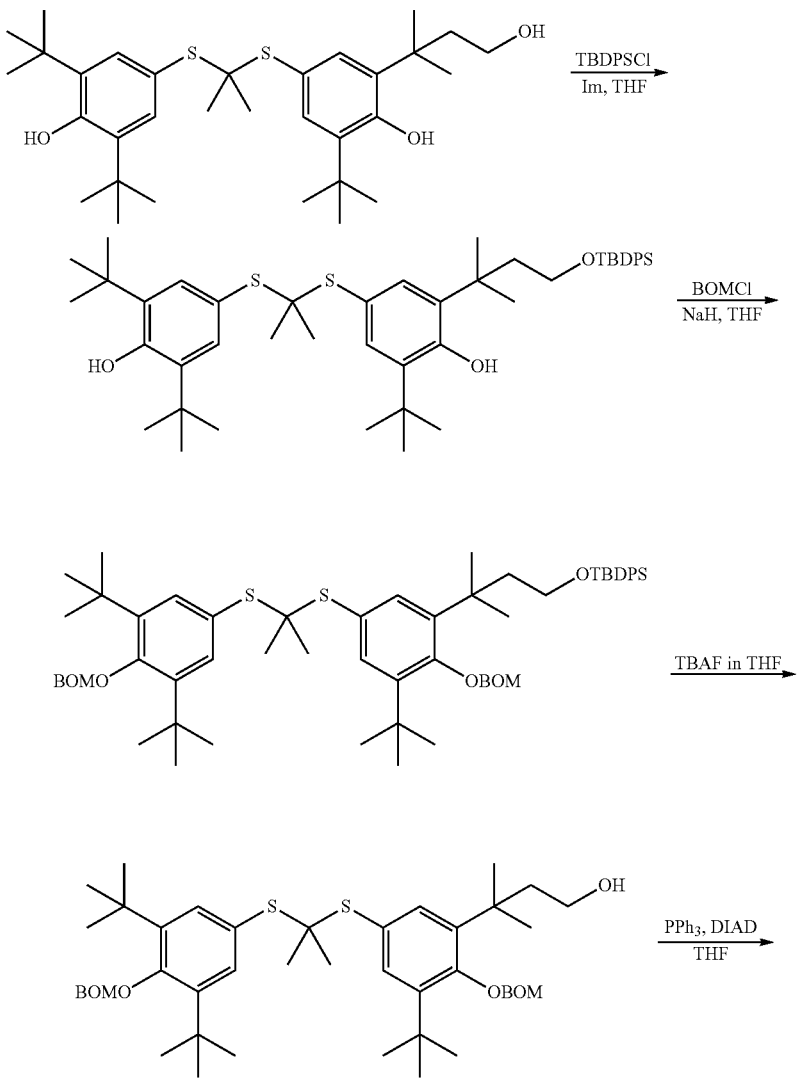

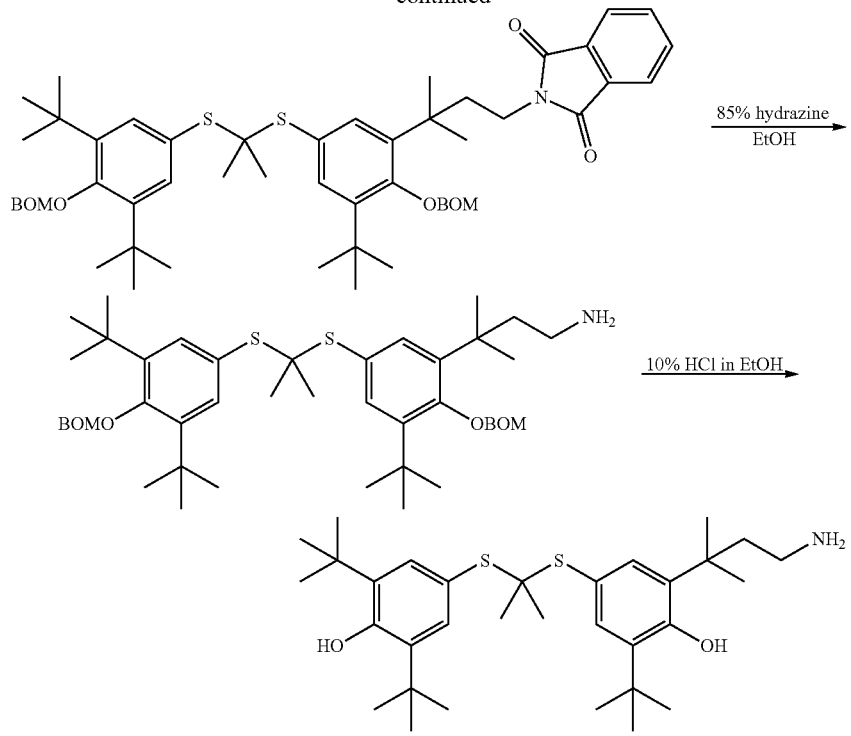

Step 1: 2,6-di-tert-butyl-4-((2-((3-(tert-butyl)-5-(4-((tert-butyldiphenylsilyl)oxo)-2-methylbutan-2-yl)-4-hydroxyphenyl)thio)propan-2-yl)thio)phenol Under the protection of $N_2$, 2,6-di-tert-butyl-4-((2-((3-(tert-butyl)-4-hydroxy-5-(4-hydroxy-2-methylbutan-2-yl)phenyl)thio)propan-2-yl)thio)phenol (6.7 g, 12.27 mmol) and Im (1.7 g, 24.5 mmol) were added to a three-necked flask containing dry THF (100 mL). The above mixture was cooled with an ice water bath, and the temperature was kept at 0 to 5° C. After stirring well, the solution of TBDPSCl (5.0 g, 18.40 mmol) in THF (10 mL) was slowly added dropwise to the above mixture, and the reaction was monitored by TLC. After the reaction was completed, the temperature was gradually raised to room temperature. The organic solvent was removed by concentration under reduced pressure. The residue was poured into $H_2O$ (50 mL), the pH was adjusted to about 4 with 2N HCl, and then EtOAc (100 mL) was added. The organic phase was separated out, and dried with anhydrous sodium sulfate. The crude product was purified by chromatography (silica gel, 200 to 300 mesh, PE:EtOAc=50:1 to 20:1) to obtain the product as a yellow oil (10.9 g, yield 113%). The crude product was used for the next step without further purification.

Step 2: (3-(2-((phenoxy)methoxy)-5-((2-((4-((phenoxy)methoxy)-3,5-di-tert-butylphenyl)thio)propan-2-yl)thio)-3-(tert-butyl)phenyl)-3-methylbutoxy)(tert-butyl)diphenylsilane

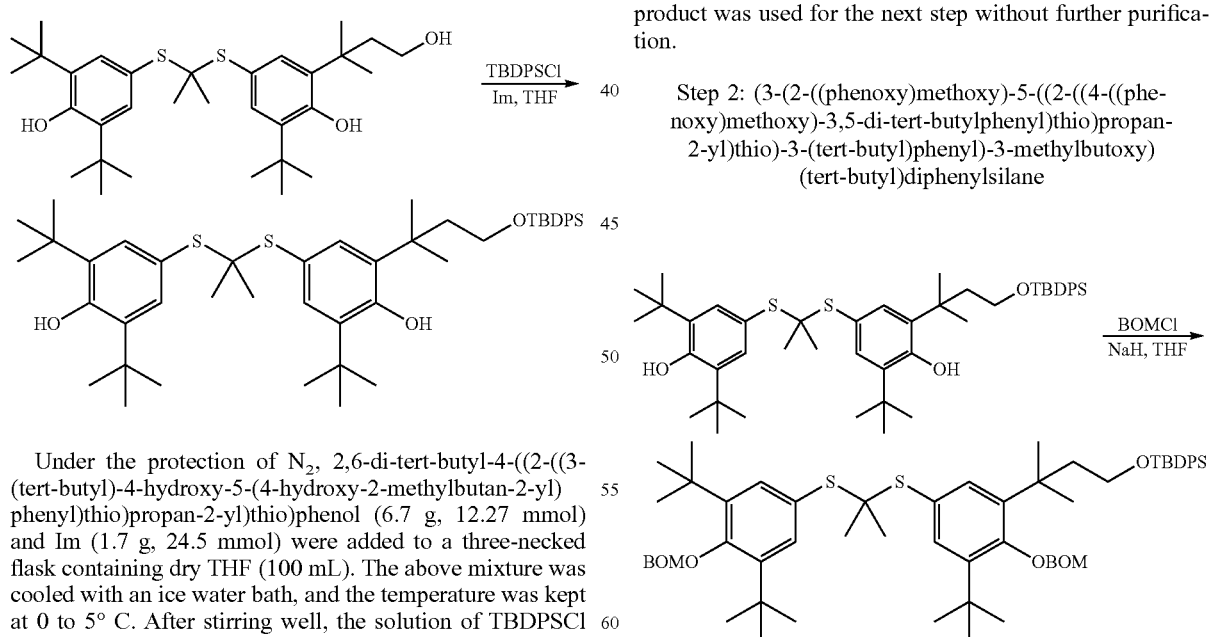

Under the protection of $N_2$, NaH (277.6 mmol, 11.1 g of solution in mineral oil, with a concentration of 60%) was added in batches into anhydrous THF (50 mL). The above mixture was cooled with an ice water bath under stirring to a temperature of 0 to 5° C. Then the solution of 2,6-di-tertbutyl-4-((2-((3-(tert-butyl)-5-(4-((tert-butyldiphenylsilyl) oxo)-2-methylbutan-2-yl)-4-hydroxyphenyl)thio)propan-2-yl)thio)phenol (10.9 g, 13.88 mmol) in dry THF (10 mL) was added dropwise to the above suspension, and the temperature was kept not to exceed 10° C. The resulting reaction solution was stirred at room temperature, and the reaction was monitored by TLC. The organic solvent was removed by concentration under reduced pressure. The residue was poured into $H_2O$ (50 mL), the pH was adjusted to about 6 with 2N HCl, and then EtOAc (100 mL) was added. The organic phase was separated out, and dried with anhydrous sodium sulfate. After concentration, a crude product was obtained as a yellow oil, which was used directly in the next step.

Step 3: 3-(2-((phenoxy)methoxy)-5-((2-((4-((phenoxy)methoxy)-3,5-di-tert-butylphenyl)thio)propan-2-yl)thio)-3-(tert-butyl)phenyl)-3-methylbutan-1-ol

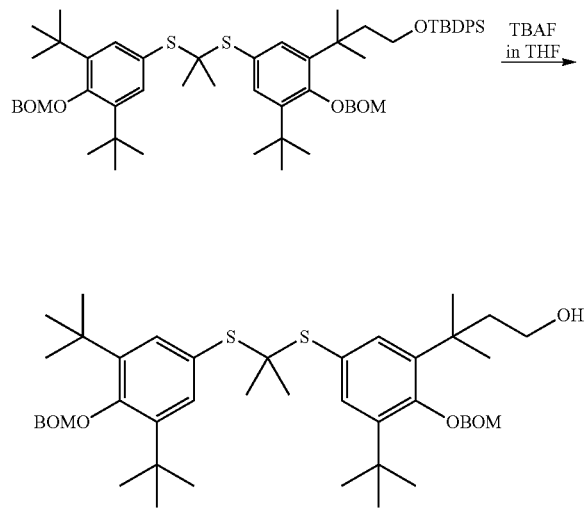

Under the protection of $N_2$, (3-(2-((phenoxy)methoxy)-5-((2-((4-((phenoxy)methoxy)-3,5-di-tert-butylphenyl)thio) propan-2-yl)thio)-3-(tert-butyl)phenyl)-3-methylbutoxy) (tert-butyl)diphenylsilane (12.0 g, crude) was added to a three-necked flask containing dry THF (100 mL). The above mixture was cooled below −10° C. with a dry ice-acetone bath, and then TBAF (50 mL, a solution of 1 M in THF) was added dropwise. After the dropwise addition, the mixture was stirred overnight at room temperature. The organic solvent was removed by concentration under reduced pressure, and the residue was poured into $H_2O$ (50 mL), and then EtOAc (100 mL) was added. The organic phase was separated out, and dried with anhydrous sodium sulfate. After concentration, a crude product was obtained as a yellow oil, which was used directly in the next step.

Step 4: 2-(3-(2-((phenoxy)methoxy)-5-((2-((4-((phenoxy)methoxy)-3,5-di-tert-butylphenyl)thio)propan-2-yl)thio)-3-(tert-butyl)phenyl)-3-methylbutyl)isoindoline-1,3-dione

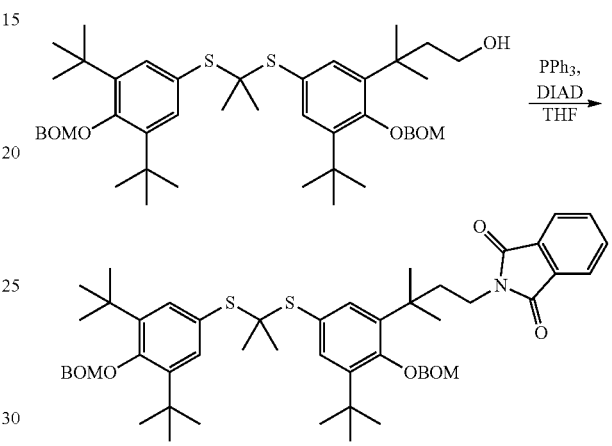

At 0° C., 3-(2-((phenoxy)methoxy)-5-((2-((4-((phenoxy)methoxy)-3,5-di-tert-butylphenyl)thio)propan-2-yl)thio)-3-(tert-butyl)phenyl)-3-methylbutan-1-ol (1.5 g, 1.91 mmol), $PPh_3$ (0.67 g, 2.55 mmol) and phthalamide (0.37 g, 2.55 mmol) were added to dry THF (10 mL), and then a solution of DIAD (0.44 g, 2.55 mmol) in THF (5 mL) was slowly added dropwise. The reaction was carried out at 0° C. for 2 hours. The organic solvent was removed by concentration under reduced pressure. To the residue was added EtOAc (20 mL), and the resultant was washed with saturated salt water, and dried with anhydrous sodium sulfate. Crude product 2-(3-(2-((phenoxy)methoxy)-5-((2-((4-((phenoxy)methoxy)-3,5-di-tert-butylphenyl)thio)propan-2-yl)thio)-3-(tert-butyl)phenyl)-3-methylbutyl)isoindoline-1,3-dione was used directly in the next step.

Step 5: 3-(2-((phenoxy)methoxy)-5-((2-((4-((phenoxy)methoxy)-3,5-di-tert-butylphenyl)thio)propan-2-yl)thio)-3-(tert-butyl)phenyl)-3-methylbutan-1-amine

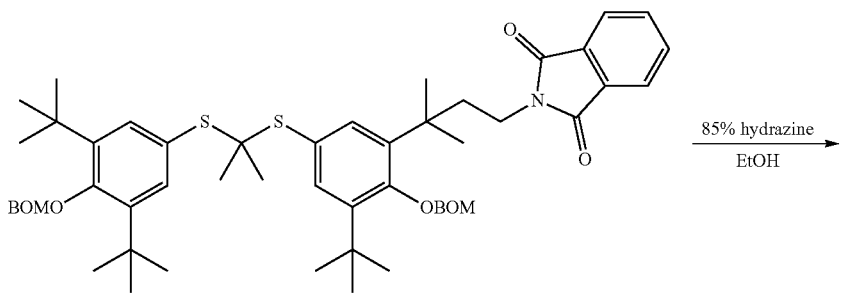

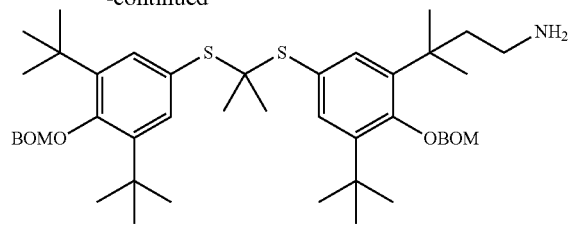

The crude product of the previous step 2-(3-(2-((phenoxy)methoxy)-5-((2-((4-((phenoxy)methoxy)-3,5-di-tert-butylphenyl)thio)propan-2-yl)thio)-3-(tert-butyl)phenyl)-3-methylbutyl)isoindoline-1,3-dione were dissolved in EtOH (100 mL), and then 85% hydrazine hydrate (75 mL) was added. The resulting solution was heated to 50° C. for reaction, and the reaction was monitored by TLC. After the reaction was completed, the temperature was gradually reduced to room temperature, and the organic solvent was removed by concentration under reduced pressure. The residue was poured into H$_2$O (50 mL), and then EtOAc (200 mL) was added. The organic phase was separated out, and dried with anhydrous sodium sulfate. The crude product was purified by chromatography (silica gel, 200 to 300 mesh, MeOH:DCM=1:100 to 1:10) to obtain the product 3-(2-((phenoxy)methoxy)-5-((2-((4-((phenoxy)methoxy)-3,5-di-tert-butylphenyl)thio)propan-2-yl)thio)-3-(tert-butyl)phenyl)-3-methylbutan-1-amine (3.5 g, yield 54% in three steps) as a yellow oil.

Step 6: 2-(4-amino-2-methylbutan-2-yl)-6-(tert-butyl)-4-((2-((3,5-di-tert-butyl-4-hydroxyphenyl)thio)propan-2-yl)thio)phenol

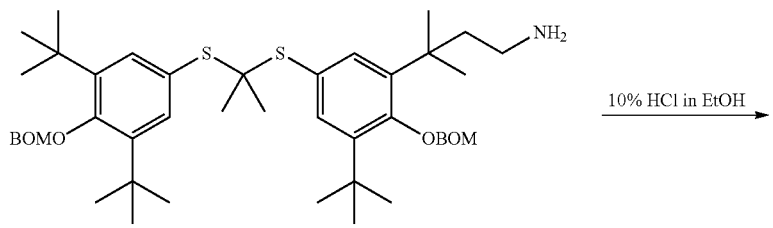

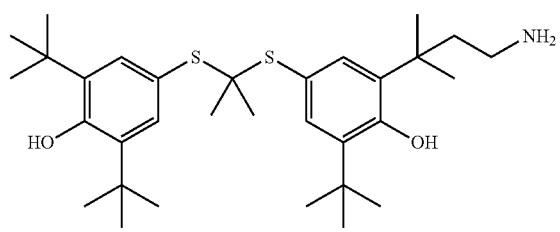 [SMILES: CC(C)(Sc1cc(C(C)(C)C)c(O)c(C(C)(C)C)c1)Sc1cc(C(C)(C)C)c(O)c(C(C)(C)CCN)c1]

3-(2-((phenoxy)methoxy)-5-((2-((4-((phenoxy)methoxy)-3,5-di-tert-butylphenyl)thio)propan-2-yl)thio)-3-(tert-butyl)phenyl)-3-methylbutan-1-amine (2.0 g, 2.54 mmol) was added to 10% HCl/EtOH (50 mL). The reaction solution was stirred overnight at 40° C. After the reaction was completed, the temperature was gradually reduced to room temperature. The organic solvent was removed by concentration under reduced pressure. The reaction solution was poured into H$_2$O (50 mL), the pH was adjusted to about 8 with NaHCO$_3$, and then EtOAc (100 mL) was added. The organic phase was separated out, and dried with anhydrous sodium sulfate. The crude product was obtained after concentration, and passed through a chromatography column (silica gel, 200 to 300 mesh, containing 0.1% ammonia water in MeOH:DCM=1:100 to 1:10 as eluent) to obtain product 2-(4-amino-2-methylbutan-2-yl)-6-(tert-butyl)-4-((2-((3,5-di-tert-butyl-4-hydroxyphenyl)thio)propan-2-yl)thio)phenol (150 mg, yield 11%) as a yellow oil. $^1$H NMR (300 MHz, CDCl$_3$): δ 7.48 (s, 1H), 7.37 (s, 2H), 7.26 (s, 2H), 2.32~2.21 (m, 2H), 2.15~2.10 (m, 2H), 1.41~38 (m, 30H), 1.28~1.26 (m, 9H). HPLC: 93.6% at 242 nm, t$_R$=6.82 min.

Example 17: 2,6-di-tert-butyl-4-((2-((3-(tert-butyl)-5-(4-(2-(diethylamino)ethoxy)-2-methylbutan-2-yl)-4-hydroxyphenyl)thio)propan-2-yl)thio)phenol

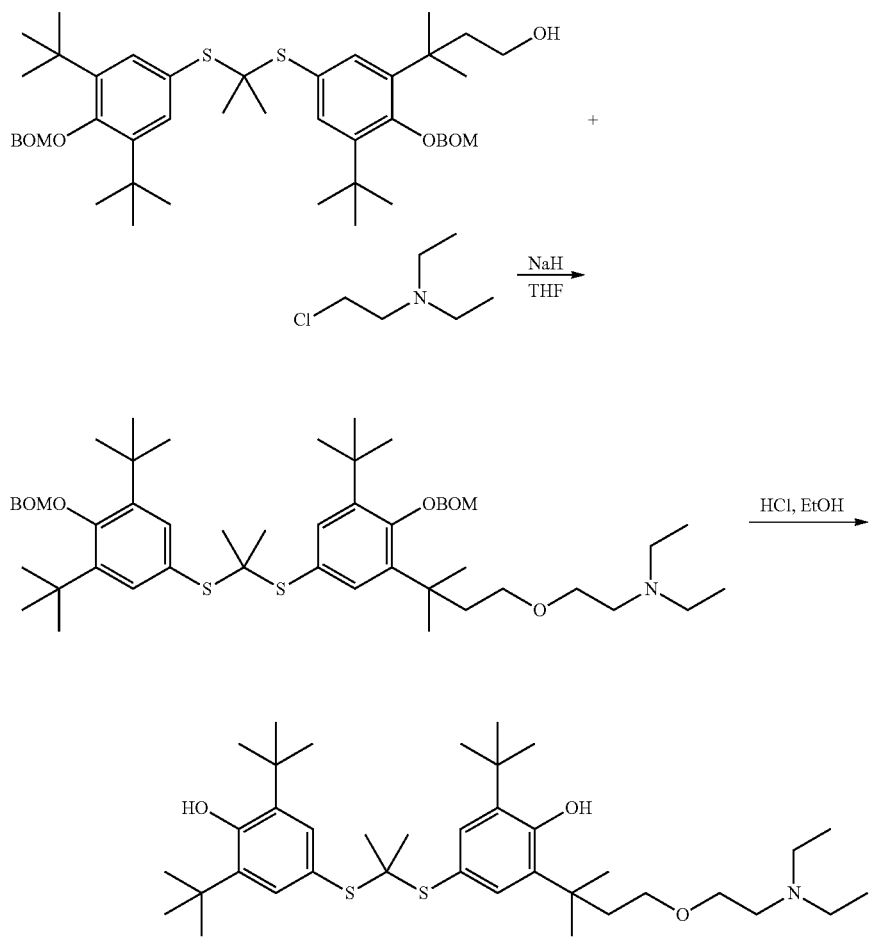

Step 1: 2,6-di-tert-butyl-4-((2-((3-(tert-butyl)-5-(4-((tert-butyldiphenylsilyl)oxo)-2-methylbutan-2-yl)-4-hydroxyphenyl)thio)propane-2-yl)thio)phenol

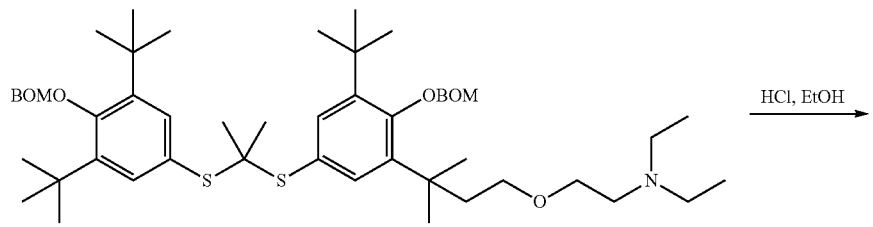

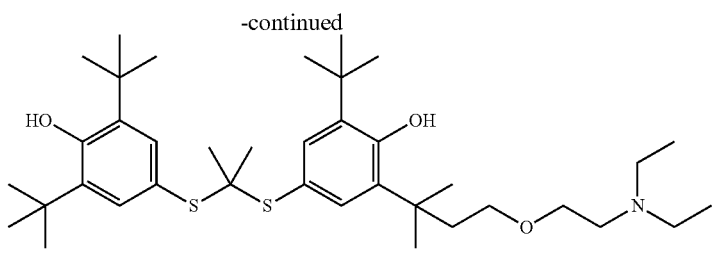

Under the protection of $N_2$, NaH (0.95 mmol, 32 mg of a solution in mineral oil which was used for protection, with a concentration of 70%) was added to dry THF (8 mL) in batches at 0° C., and then 2,6-di-tert-butyl-4-((2-((3-(tert-butyl)-4-hydroxy-5-(4-hydroxy-2-methylbutan-2-yl)phenyl)thio)propan-2-yl)thio)phenol (147 mg, 0.19 mmol) and 2-chloro-N,N-diethyl-1-amine (50 mg, 0.29 mmol) were added, respectively. The resulting mixture was stirred overnight at 70° C. The reaction was monitored by TLC. After the reaction was completed, the temperature was gradually reduced to room temperature. The organic solvent was removed by concentration under reduced pressure. The residue was poured into $H_2O$ (50 mL), and EtOAc (100 mL) was added. The organic phase was separated out, and dried with anhydrous sodium sulfate. The crude product was purified by chromatography (silica gel, 200 to 300 mesh, DCM:MeOH=10:1) to obtain the product as a yellow oil (80 mg, yield 48%).

Step 2: 2,6-di-tert-butyl-4-((2-((3-(tert-butyl)-5-(4-(2-(diethylamino)ethoxy)-2-methylbutan-2-yl)-4-hydroxyphenyl)thio)propan-2-yl)thio)phenol 2,6-di-tert-butyl-4-((2-((3-(tert-butyl)-5-(4-((tert-butyldiphenylsilyl)oxo)-2-methylbutan-2-yl)-4-hydroxyphenyl)thio)propane-2-yl)thio)phenol (80 mg, 0.09 mmol) was added to 10% HCl/EtOH (50 mL) and stirred overnight at 40° C. After the reaction was completed, the temperature was gradually reduced to room temperature. The organic solvent was removed by concentration under reduced pressure. The residue was poured into $H_2O$ (50 mL), the pH was adjusted to about 8 with $NaHCO_3$, and then EtOAc (100 mL) was added. The organic phase was separated out, and dried with anhydrous sodium sulfate. The crude product was obtained after concentration, and passed through a chromatography column (silica gel, 200 to 300 mesh, MeOH containing 0.1% ammonia water:DCM=1:100 to 1:10 as eluent) to obtain the product 2,6-di-tert-butyl-4-((2-((3-(tert-butyl)-5-(4-(2-(diethylamino)ethoxy)-2-methylbutan-2-yl)-4-hydroxyphenyl)thio)propan-2-yl)thio)phenol (35 mg, yield 60%) as a yellow oil. $^1$H NMR (300 MHz, DMSO-d6): δ 8.02 (s, 1H), 7.42~7.37 (s, 2H), 7.33~7.23 (s, 2H), 7.10 (s, 1H), 3.51 (m, 1H), 3.19~3.06 (m, 8H), 2.18~2.13 (m, 2H),

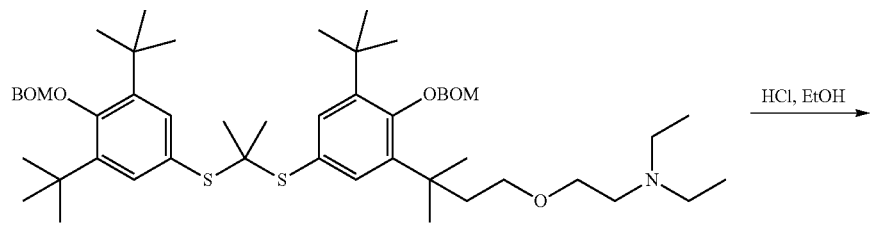

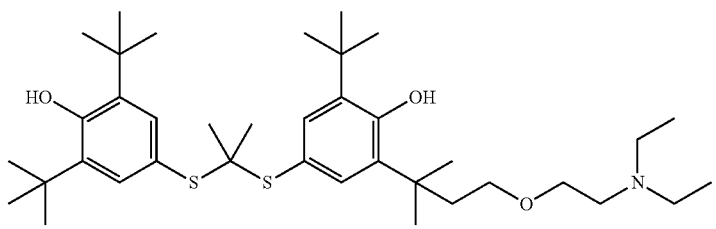 [SMILES: CCN(CC)CCOCCC(C)(C)c1cc(SC(C)(C)Sc2cc(C(C)(C)C)c(O)c(C(C)(C)C)c2)cc(C(C)(C)C)c1O]

1.42~1.36 (m, 30H), 1.26 (s, 9H), 1.15 (t, 6H, J=6 Hz). LC-MS: 646.4 [M+H]⁺. HPLC: 93.5% at 242 nm, t_R=18.61 min.

Example 18: 2,6-di-tert-butyl-4-((2-((3-(tert-butyl)-4-hydroxy-5-(2-methyl-4-(2-morpholinoethoxy)butan-2-yl)phenyl)thio)propan-2-yl)thio)phenol

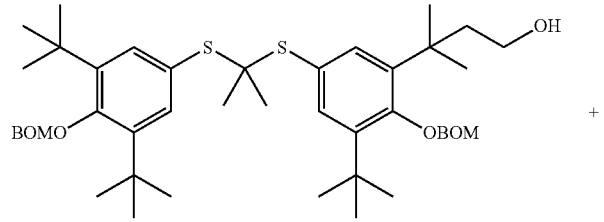

Step 1: 4-(2-(3-(2-((phenoxy)methoxy)-5-((2-((4-((phenoxy)methoxy)-3,5-di-tert-butylphenyl)thio)propan-2-yl)thio)-3-(tert-butyl)phenyl)-3-methylbutoxy)ethyl)morpholine

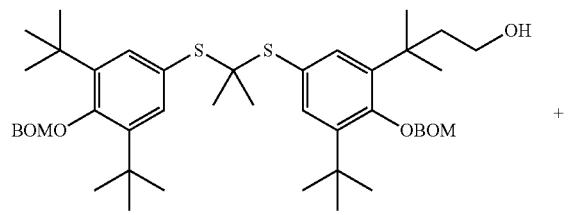

+

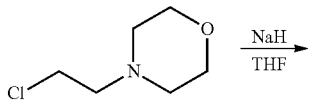 NaH/THF →

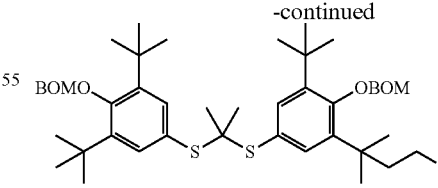

Under the protection of N₂, NaH (1.0 mmol, 34 mg of a solution in mineral oil which was used for protection, with a concentration of 70%) was added to dry THF (15 mL) in batches at 0° C., and then 4-(2-chloroethyl) morpholine (450 mg, 3 mmol) and 2,6-di-tert-butyl-4-((2-((3-(tert-butyl)-4-hydroxy-5-(4-hydroxy-2-methylbutan-2-yl)phenyl)thio)propan-2-yl)thio)phenol (240 mg, 0.3 mmol) were added,

+

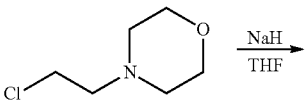 NaH/THF →

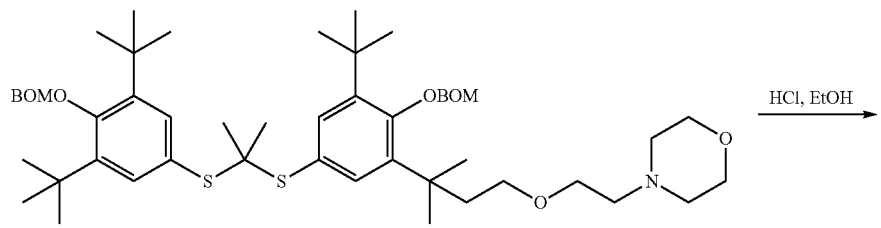 HCl, EtOH →

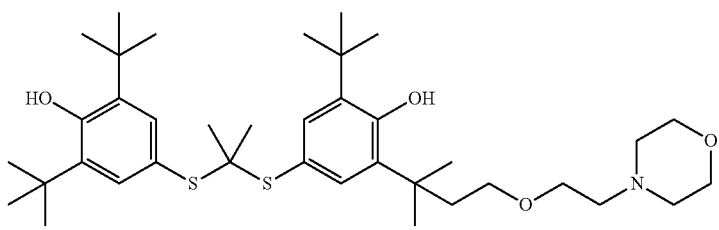 [SMILES: CC(C)(Sc1cc(C(C)(C)C)c(O)c(C(C)(C)C)c1)Sc1cc(C(C)(C)C)c(O)c(C(C)(C)CCOCCN2CCOCC2)c1]

respectively. The resulting mixture was stirred overnight at 70° C. The reaction was monitored by TLC. After the reaction was completed, the temperature was gradually reduced to room temperature. The organic solvent was removed by concentration under reduced pressure. The residue was poured into H$_2$O (50 mL), and EtOAc (100 mL) was added. The organic phase was separated out, and dried with anhydrous sodium sulfate. The crude product was purified by chromatography (silica gel, 200 to 300 mesh), DCM:MeOH=10:1) to obtain the product as a yellow oil (190 mg, yield 69%).

Step 2: 2,6-di-tert-butyl-4-((2-((3-(tert-butyl)-4-hydroxy-5-(2-methyl-4-(2-morpholinoethoxy)butan-2-yl)phenyl)thio)propan-2-yl)thio)phenol

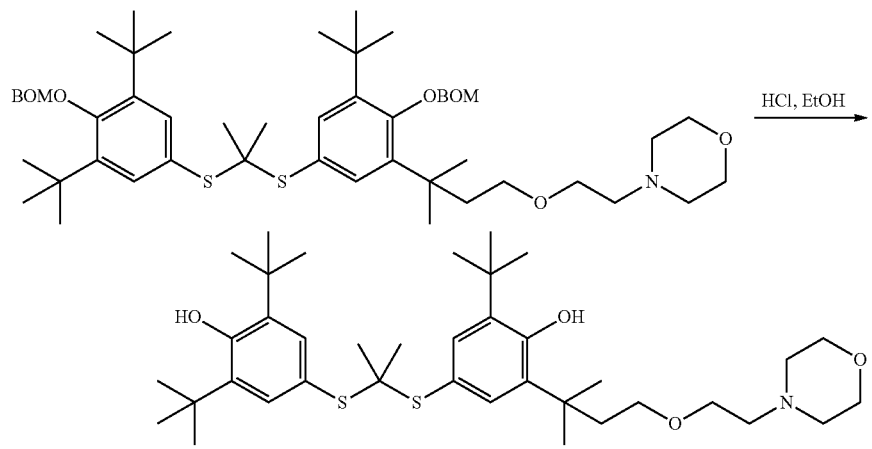

4-(2-(3-(2-((phenoxy)methoxy)-5-((2-((4-((phenoxy)methoxy)-3,5-di-tert-butylphenyl)thio)propan-2-yl)thio)-3-(tert-butyl)phenyl)-3-methylbutoxy)ethyl)morpholine (120 mg, 0.13 mmol) was added to 10% HCl/EtOH (20 mL), and stirred overnight at 40° C. After the reaction was completed, the temperature was gradually reduced to room temperature. The organic solvent was removed by concentration under reduced pressure. The residue was poured into H$_2$O (10 mL), the pH was adjusted to about 8 with NaHCO$_3$, and then EtOAc (20 mL) was added. The organic phase was separated out, and dried with anhydrous sodium sulfate. The crude product was obtained after concentration, and passed through a chromatography column (silica gel, 200 to 300 mesh, MeOH containing 0.1% ammonia water:DCM=1:100 to 1:10 as eluent) to obtain the product 2,6-di-tert-butyl-4-((2-((3-(tert-butyl)-4-hydroxy-5-(2-methyl-4-(2-morpholinoethoxy)butan-2-yl)phenyl)thio)propan-2-yl)thio)phenol (65 mg, yield 74%) as a yellow oil. $^1$H NMR (300 MHz, DMSO-d6): δ 7.95 (s, 1H), 7.41 (s, 1H), 7.40 (s, 1H), 7.37~7.32 (m, 2H), 7.21 (s, 1H), 3.49~3.46 (m, 4H), 3.24 (t, 2H, J=6 Hz), 3.07 (t, 2H, J=6 Hz), 2.53~2.49 (m, 6H), 2.25 (t, 2H, J=6 Hz), 1.38~1.34 (m, 30H), 1.22 (s, 9H). LC-MS: 660.4 [M+H]$^+$. HPLC: 94.4% at 242 nm, $t_R$=14.19 min.

Example 19: 3-(3-(tert-butyl)-5-((2-((3,5-di-tert-butyl-4-hydroxyphenyl)thio)propan-2-yl)thio)-2-hydroxyphenyl)-3-methylbutyl glycinate

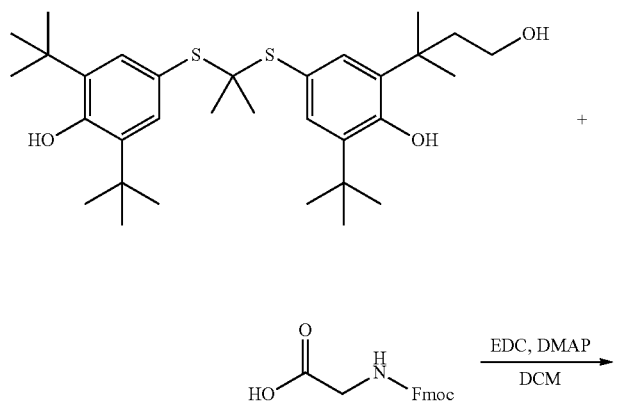

Step 1: 3-(3-(tert-butyl)-5-((2-((3,5-di-tert-butyl-4-hydroxyphenyl)thio)propan-2-yl)thio)-2-hydroxyphenyl)-3-methylbutyl (((9H-fluoren-9-yl)methoxy)carbonyl)glycinate

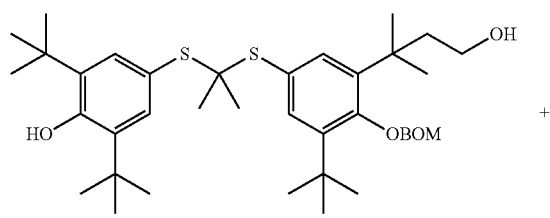

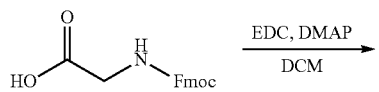

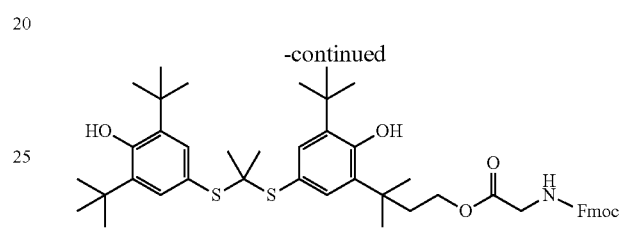

At room temperature, 2,6-di-tert-butyl-4-((2-((3-(tert-butyl)-4-hydroxy-5-(4-hydroxy-2-methylbutan-2-yl)phenyl)thio)propan-2-yl)thio)phenol (500 mg, 0.92 mmol), (((9H-fluoren-9-yl)methoxy)carbonyl) glycinate (328 mg, 1.1 mmol), DMAP (112 mg, 0.92 mmol) and EDC hydrochloride (264 mg, 1.38 mmol) were added to DCM (50 mL), respectively. The resulting reaction solution was stirred at room temperature, and the reaction was monitored by TLC. After the reaction was completed, the mixture was washed with saturated salt water and dried with anhydrous sodium sulfate. The crude product was purified by chromatography (silica gel, 200 to 300 mesh, EtOAc:PE=1:30 to 1:10) to obtain the product (525 mg, yield 69%) as a white foam. LC-MS: 826.2 [M+H]$^+$.

Step 2: 3-(3-(tert-butyl)-5-((2-((3,5-di-tert-butyl-4-hydroxyphenyl)thio)propan-2-yl)thio)-2-hydroxyphenyl)-3-methylbutyl glycinate

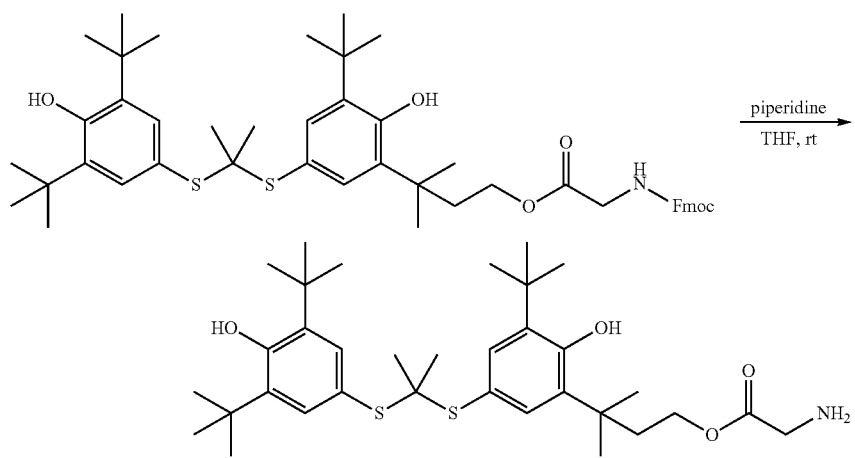

Step 1: 3-(3-(tert-butyl)-5-((2-((3,5-di-tert-butyl-4-hydroxyphenyl)thio)propan-2-yl)thio)-2-hydroxyphenyl)-3-methylbutyl (((9H-fluoren-9-yl)methoxy)carbonyl)alaninate

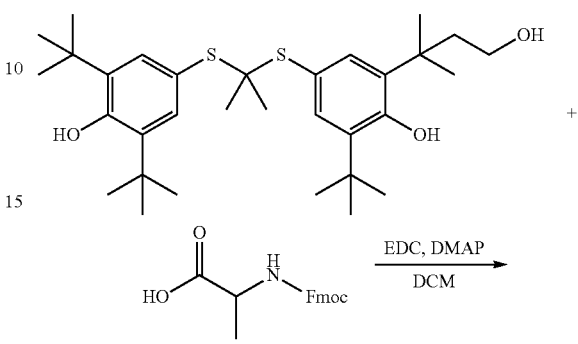

At room temperature, 3-(3-(tert-butyl)-5-((2-((3,5-di-tert-butyl-4-hydroxyphenyl)thio)propan-2-yl)thio)-2-hydroxyphenyl)-3-methylbutyl (((9H-fluoren-9-yl)methoxy)carbonyl)glycinate (526 mg, 0.64 mmol) was added to THF (10 mL), and then piperidine (10 mL) was slowly added dropwise to the above mixture. The resulting reaction solution was stirred at room temperature, and the reaction was monitored by TLC. After the reaction was completed, THF was removed by concentration under reduced pressure. The residue was freeze-dried to remove water, and extracted with EtOAc (50 mL). The crude product was purified by chromatography (silica gel, 200 to 300 mesh, EtOAc:PE=1:10 to 1:1) to obtain the product (320 mg, yield 83%) as a white foam. $^1$H NMR (300 MHz, CDCl$_3$): δ 7.46 (s, 1H), 7.35 (m, 2H), 7.28 (s, 1H), 4.06 (t, 2H, J=6 Hz), 3.95 (m, 1H), 2.03 (t, 2H, J=6 Hz), 1.54~1.38 (39H).

Example 20: 3-(3-(tert-butyl)-5-((2-((3,5-di-tert-butyl-4-hydroxyphenyl)thio)propan-2-yl)thio)-2-hydroxyphenyl)-3-methylbutyl alaninate

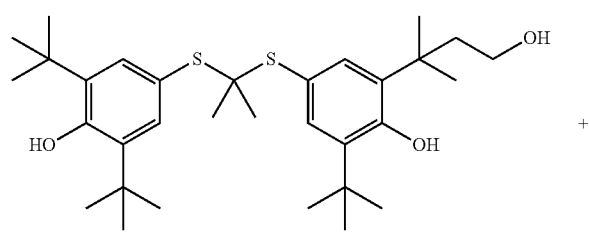

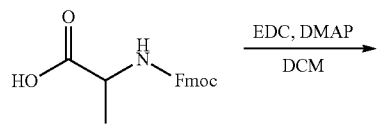

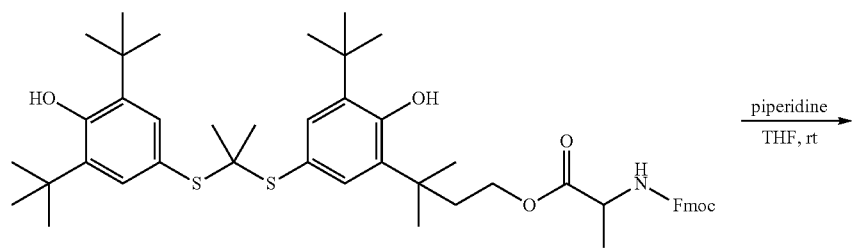

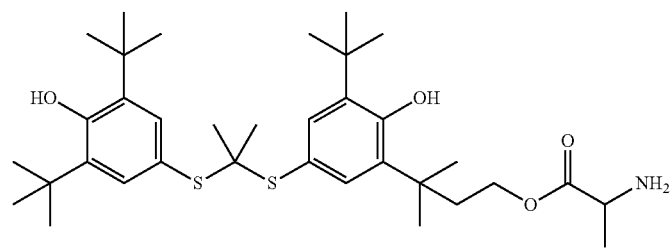

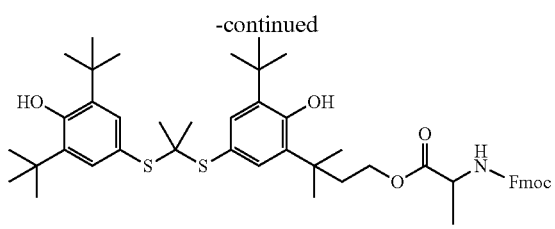

At room temperature, 2,6-di-tert-butyl-4-((2-((3-(tert-butyl)-4-hydroxy-5-(4-hydroxy-2-methylbutan-2-yl)phenyl)thio)propan-2-yl)thio)phenol (500 mg, 0.92 mmol), (((9H-fluoren-9-yl)methoxy)carbonyl) alaninate (342 mg, 1.1 mmol), DMAP (112 mg, 0.92 mmol) and EDC hydrochloride (264 mg, 1.38 mmol) were added to DCM (50 mL), respectively. The resulting reaction solution was stirred at room temperature, and the reaction was monitored by TLC. After the reaction was completed, the mixture was washed with saturated salt water and dried with anhydrous sodium sulfate. The crude product was purified by chromatography (silica gel, 200 to 300 mesh, EtOAc:PE=1:30 to 1:10) to obtain the product (540 mg, produced 70%) as a white foam. LC-MS: 840.0 [M+H]$^+$.

Step 2: 3-(3-(tert-butyl)-5-((2-((3,5-di-tert-butyl-4-hydroxyphenyl)thio)propan-2-yl)thio)-2-hydroxyphenyl)-3-methylbutyl alaninate

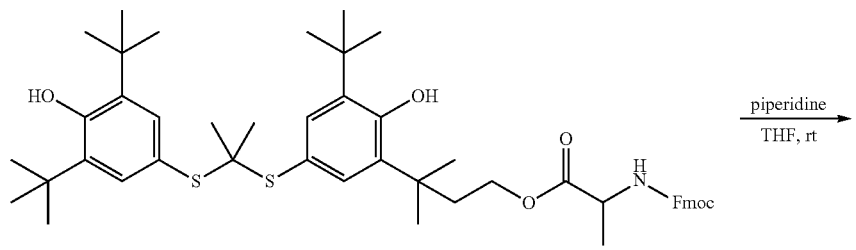

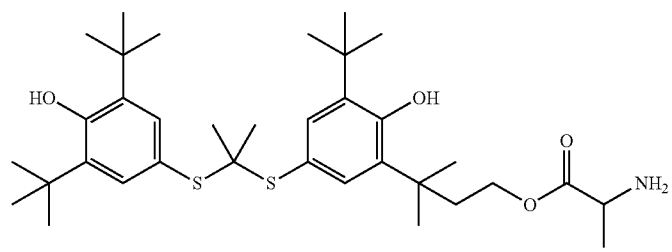

At room temperature, 3-(3-(tert-butyl)-5-((2-((3,5-di-tert-butyl-4-hydroxyphenyl)thio)propan-2-yl)thio)-2-hydroxyphenyl)-3-methylbutyl (((9H-fluoren-9-yl)methoxy)carbonyl)alaninate (540 mg, 0.64 mmol) was added to THF (10 mL), and then piperidine (10 mL) was slowly added dropwise to the above mixture. The resulting reaction solution was stirred at room temperature, and the reaction was monitored by TLC. After the reaction was completed, THF was removed by concentration under reduced pressure. The residue was freeze-dried to remove water, and extracted with EtOAc (50 mL). The crude product was purified by chromatography (silica gel, 200 to 300 mesh, EtOAc:PE=1:10 to 1:1) to obtain the product (340 mg, yield 86%) as a white foam. $^1$H NMR (300 MHz, CDCl$_3$): δ 7.38 (s, 1H), 7.30 (m, 2H), 7.25 (s, 1H), 4.10 (t, 2H, J=6 Hz), 3.68 (m, 1H), 2.10 (t, 2H, J=6 Hz), 1.54~1.38 (39H), 1.35 (d, 3H, J=6 Hz).

Example 21: methyl 2-((3-(3-(tert-butyl)-5-((2-((3, 5-di-tert-butyl-4-hydroxyphenyl)thio)propan-2-yl) thio)-2-hydroxyphenyl)-3-methylbutyl)aminoacetate 2-(4-amino-2-methylbutan-2-yl)-6-(tert-butyl)-4-((2-((3, 5-di-tert-butyl-4-hydroxyphenyl)thio)propan-2-yl)thio)phenol (2.0 g, 1.52 mmol), cesium carbonate (1.78 g, 5.50 mmol) and potassium iodide (0.913 g, 5.50 mmol) were added to anhydrous THF (50 mL), respectively, and then a solution of methyl bromoacetate (0.253 g, 1.52 mmol) in THF (10 mL) was slowly added dropwise to the above mixture under stirring. After dropwise addition was finished, the mixture was stirred overnight at room temperature. After the reaction was completed, the organic solvent was removed by concentration under reduced pressure, and the residue was poured into H$_2$O (50 mL), and then EtOAc (100 mL) was added. The organic phase was separated out, and dried with anhydrous sodium sulfate. The crude product was obtained after concentration, and passed through a chromatography column (silica gel, 200 to 300 mesh, EtOAc:PE=1: 100 to 1:50) to obtain the product methyl 2-((3-(3-(tert-butyl)-5-((2-((3,5-di-tert-butyl-4-hydroxyphenyl)thio) propan-2-yl)thio)-2-hydroxyphenyl)-3-methylbutyl) aminoacetate (780 mg, yield 34%) as an oily substance. $^1$H NMR (300 MHz, DMSO-d6): δ 7.41 (s, 1H), 7.35 (s, 2H), 7.22 (s, 1H), 3.54 (s, 3H), 3.17 (s, 2H), 2.21 (d, 2H, J=6 Hz), 1.94 (t, 2H, J=6 Hz), 1.42~1.33 (m, 30H), 1.26 (s, 9H). HPLC: 91.2% at 242 nm, $t_R$=9.52 min.

Example 22: dimethyl 2,2'-((3-(3-(tert-butyl)-5-((2-((3,5-di-tert-butyl-4-hydroxyphenyl)thio)propan-2-yl)thio)-2-hydroxyphenyl)-3-methylbutyl)azanediyl) diacetate

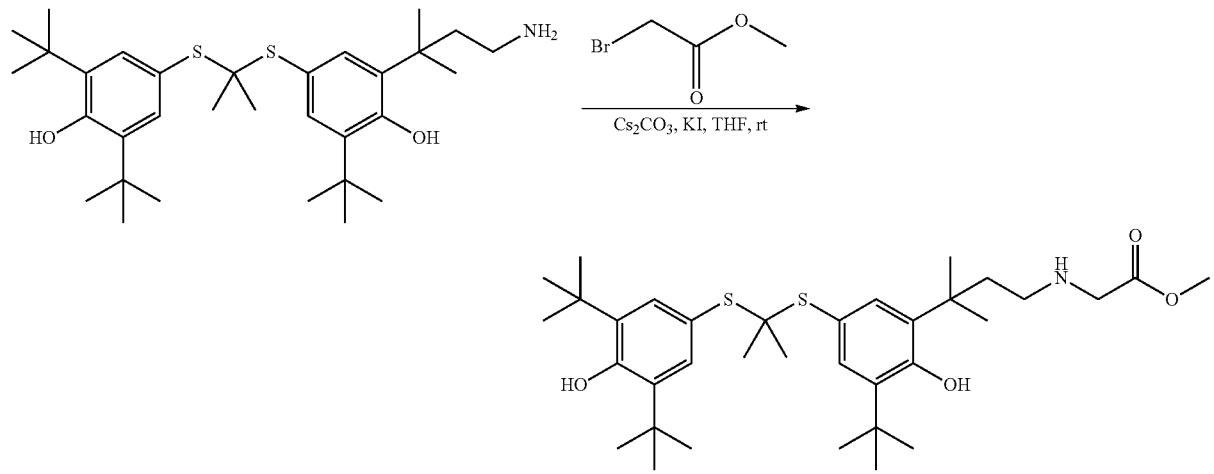

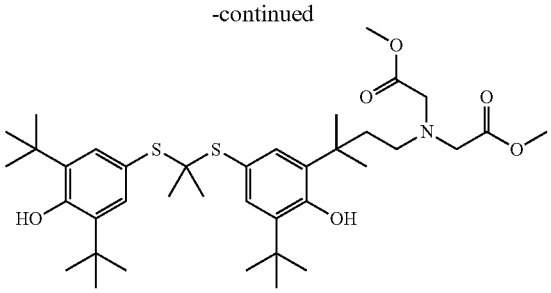

-continued 2-(4-amino-2-methylbutan-2-yl)-6-(tert-butyl)-4-((2-((3, 5-di-tert-butyl-4-hydroxyphenyl)thio)propan-2-yl)thio)phenol (2.0 g, 1.52 mmol), cesium carbonate (1.78 g, 5.50 mmol) and potassium iodide (0.913 g, 5.50 mmol) were added to anhydrous THF (50 mL), respectively, and then the solution of methyl bromoacetate (0.518 g, 3.1 mmol) in THF (10 mL) was slowly added dropwise to the above mixture under stirring. After dropwise addition, the mixture was stirred overnight at room temperature. After the reaction was completed, the organic solvent was removed by concentration under reduced pressure, and the reaction solution was poured into H$_2$O (50 mL), and then EtOAc (100 mL) was added. The organic phase was separated out, and dried with anhydrous sodium sulfate. The crude product was obtained after concentration, and purified by chromatography (silica gel, 200 to 300 mesh, EtOAc:PE=1:100 to 1:5) to obtain the product dimethyl 2,2'-((3-(3-(tert-butyl)-5-((2-((3,5-di-tert-butyl-4-hydroxyphenyl)thio)propan-2-yl)thio)-2-hydroxyphenyl)-3-methylbutyl)azanediyl)diacetate (420 mg, yield 17%) as an oil substance. $^1$H NMR (300 MHz, DMSO-d6): δ 7.94 (s, 1H), 7.42 (s, 1H), 7.38 (s, 1H), 7.35 (s, 2H), 7.20 (s, 1H), 3.52 (s, 6H), 3.35 (t, 2H, J=6 Hz), 2.51 (t, 2H, J=6 Hz), 2.36~2.26 (m, 2H), 1.98~1.94 (m, 2H), 1.39 (s, 18H), 1.37 (s, 6H), 1.32 (s, 6H), 1.26 (s, 9H). HPLC: 94.5% at 242 nm, $t_R$=8.56 min.

Example 23: N-(3-(3-(tert-butyl)-5-((2-((3,5-di-tert-butyl-4-hydroxyphenyl)thio)propan-2-yl)thio)-2-hydroxyphenyl)-3-methylbutyl)-5-(1,2-dithiolan-3-yl)pentanamide

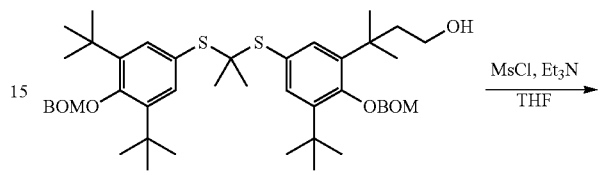

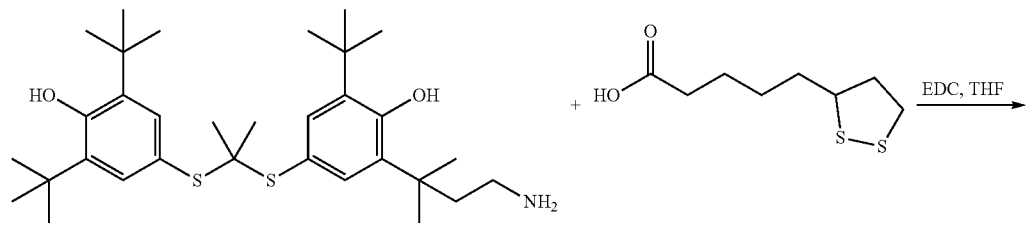

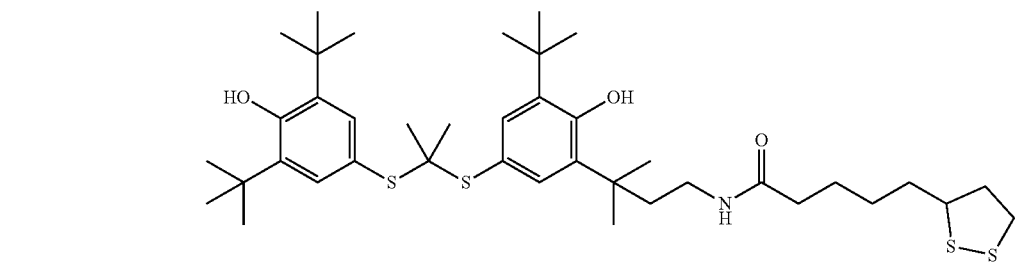 [SMILES: CC(C)(Sc1cc(C(C)(C)C)c(O)c(C(C)(C)C)c1)Sc1cc(C(C)(C)C)c(O)c(C(C)(C)CCNC(=O)CCCCC2CCSS2)c1]

At room temperature, 2-(4-amino-2-methylbutan-2-yl)-6-(tert-butyl)-4-((2-((3,5-di-tert-butyl-4-hydroxyphenyl)thio)propan-2-yl)thio)phenol (300 mg, 0.55 mmol), lipoic acid (113 mg, 0.55 mmol) and EDC hydrochloride (126 mg, 0.66 mmol) were added to THF (20 mL), respectively, and the reaction solution was stirred overnight at room temperature. The organic solvent was removed by concentration under reduced pressure. To the residue was added EtOAc (50 mL) and saturated salt water (10 mL), respectively. The organic phase was washed with saturated salt water and dried with anhydrous sodium sulfate. The crude product was passed through a chromatography column (silica gel, EtOAc:PE=1:50 to 1:20) to obtain the product N-(3-(3-(tert-butyl)-5-((2-((3,5-di-tert-butyl-4-hydroxyphenyl)thio)propan-2-yl)thio)-2-hydroxyphenyl)-3-methylbutyl)-5-(1,2-dithiolan-3-yl)pentanamide (110 mg, yield 27%) as a white solid. $^1$H NMR (300 MHz, DMSO-d6): δ 7.96 (s, 1H), 7.51 (s, 1H), 7.43 (m, 1H), 7.38~7.35 (m, 2H), 7.26 (s, 1H), 5.63 (s, 1H), 3.64 (t, 2H, J=6 Hz), 3.16~3.10 (m, 4H), 2.57~2.52 (m, 2H), 2.48~2.51 (m, 4H), 2.00~1.98 (m, 2H), 1.39~1.27 (m, 30H), 1.24 (s, 9H). HPLC: 90.7% at 242 nm, $t_R$=10.22 min.

Example 24: 2,6-di-tert-butyl-4-((2-((3-(tert-butyl)-4-hydroxy-5-(2-methyl-4-(1H-1,2,4-triazol-1-yl)butan-2-yl)phenyl)thio)propan-2-yl)thio)phenol

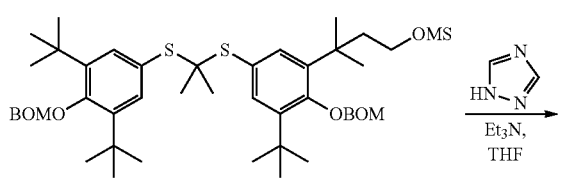

-continued

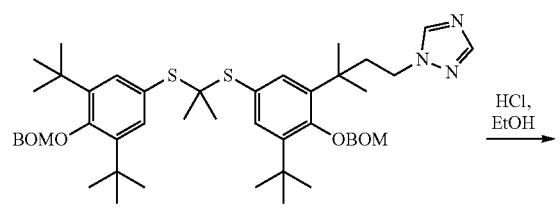

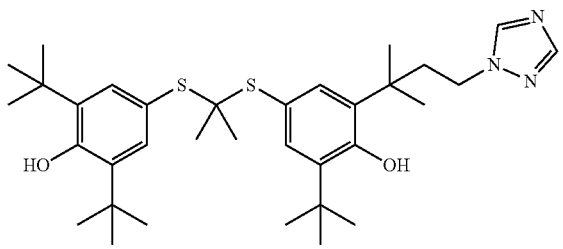

Step 1: 3-(2-((phenoxy)methoxy)-5-((2-((4-((phenoxy)methoxy)-3,5-di-tert-butylphenyl)thio)propan-2-yl)thio)-3-(tert-butyl)phenyl)-3-methylbutyl methanesulfonate

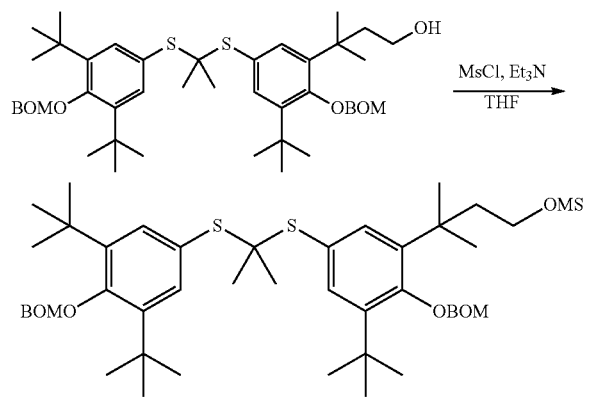

At room temperature, 3-(2-((phenoxy)methoxy)-5-((2-((4-((phenoxy)methoxy)-3,5-di-tert-butylphenyl)thio)propan-2-yl)thio)-3-(tert-butyl)phenyl)-3-methylbutan-1-ol (800 mg, 1.0 mmol) and Et$_3$N (1 mL) were added to THF (20 mL), respectively, and then MsCl (2 mL) was added dropwise to the above mixture. The resulting reaction solution was stirred at room temperature, and the reaction was monitored by TLC. After the raw materials were completely consumed, THF was removed by concentration under reduced pressure. To the residue was added saturated salt water (20 mL), extracted with EtOAc (50 mL), and dried with anhydrous sodium sulfate. The resulting mixture was used in the next step without further purification.

Step 2: 1-(3-(2-((phenoxy)methoxy)-5-((2-((4-((phenoxy)methoxy)-3,5-di-tert-butylphenyl)thio)propan-2-yl)thio)-3-(tert-butyl)phenyl)-3-methylbutyl)-1H-1,2,4-triazole

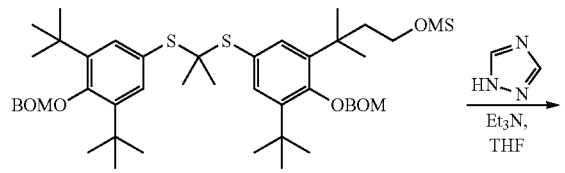

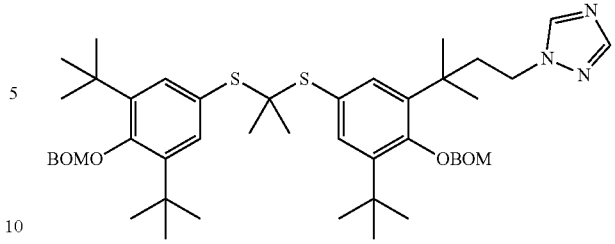

At room temperature, 3-(2-((phenoxy)methoxy)-5-((2-((4-((phenoxy)methoxy)-3,5-di-tert-butylphenyl)thio)propan-2-yl)thio)-3-(tert-butyl)phenyl)-3-methylbutyl methanesulfonate (crude from the previous step) and Et$_3$N (1 mL) were added to THF (20 mL), respectively, and then 1H-1,2,4-triazole (1 g) was added. The resulting reaction solution was stirred at room temperature, and the reaction was monitored by TLC. After the raw materials were completely consumed, THF was removed by concentration under reduced pressure. To the residue was added saturated salt water (20 mL), extracted with EtOAc (50 mL), and dried with anhydrous sodium sulfate. The resulting mixture was used in the next step without further purification.

Step 3: 2,6-di-tert-butyl-4-((2-((3-(tert-butyl)-4-hydroxy-5-(2-methyl-4-(1H-1,2,4-triazol-1-yl)butan-2-yl)phenyl)thio)propan-2-yl)thio)phenol

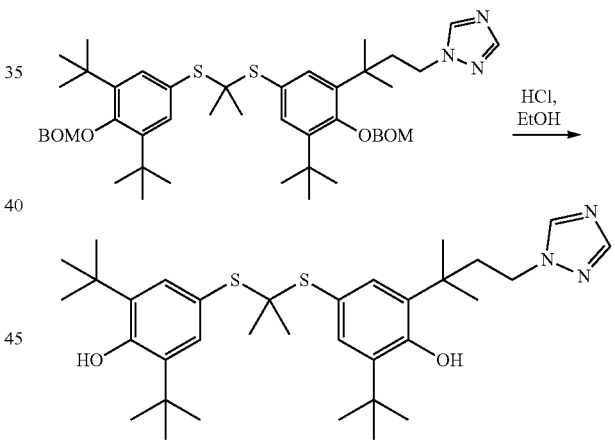

1-(3-(2-((phenoxy)methoxy)-5-((2-((4-((phenoxy)methoxy)-3,5-di-tert-butylphenyl)thio)propan-2-yl)thio)-3-(tert-butyl)phenyl)-3-methylbutyl)-1H-1,2,4-triazole (crude from the previous step) was added to 10% HCl/EtOH (10 mL) and stirred overnight at 40° C. After the reaction was completed, the temperature was gradually reduced to room temperature. The organic solvent was removed by concentration under reduced pressure. The reaction solution was poured into H$_2$O (10 mL), the pH was adjusted to about 8 with NaHCO$_3$, and then EtOAc (20 mL) was added. The organic phase was separated out, and dried with anhydrous sodium sulfate. The crude product was obtained after concentration, and passed through a chromatography column (silica gel, 200 to 300 mesh, EtOAc:PE=1:50 to 1:20 as eluent) to obtain the product 2,6-di-tert-butyl-4-((2-((3-(tert-butyl)-4-hydroxy-5-(2-methyl-4-(1H-1,2,4-triazol-1-yl)butan-2-yl)phenyl)thio)propan-2-yl)thio)phenol (50 mg, yield 8% in three steps) as a light yellow foam. $^1$H NMR (300 MHz, CDCl$_3$): δ 8.65 (s, 1H), 8.01 (s, 1H), 7.36 (s, 1H), 7.31 (s, 2H), 7.24 (s, 2H), 3.82~3.71 (m, 2H), 2.15~2.10 (m, 2H), 1.41~38 (m, 30H), 1.28~1.26 (m, 9H). HPLC: 93.6% at 242 nm, $t_R$=14.2 min.

Example 25: N-(3-(3-(tert-butyl)-5-((2-((3,5-di-tert-butyl-4-hydroxyphenyl)thio)propan-2-yl)thio)-2-hydroxyphenyl)-3-methylbutyl)cyclopropanesulfonamide

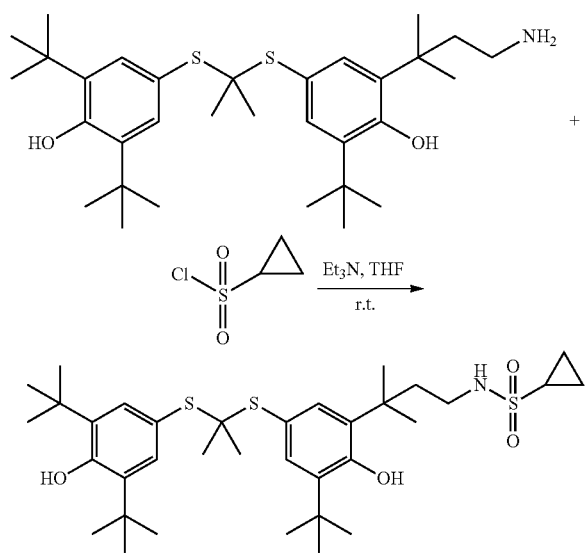

At room temperature, 2-(4-amino-2-methylbutan-2-yl)-6-(tert-butyl)-4-((2-((3,5-di-tert-butyl-4-hydroxyphenyl)thio)propan-2-yl)thio)phenol (300 mg, 0.55 mmol), cyclopropanesulfonyl chloride (84 mg, 0.60 mmol) and Et$_3$N (111 mg, 1.1 mmol) were added to THF (20 mL), respectively, and the reaction solution was stirred overnight at room temperature. The organic solvent was removed by concentration under reduced pressure. To the residue was added EtOAc (50 mL) and saturated salt water (10 mL), respectively. The organic phase was washed with saturated salt water and dried with anhydrous sodium sulfate. The crude product was passed through a chromatography column (silica gel, EtOAc:PE=1:50 to 1:30) to obtain the product N-(3-(3-(tert-butyl)-5-((2-((3,5-di-tert-butyl-4-hydroxyphenyl)thio)propan-2-yl)thio)-2-hydroxyphenyl)-3-methylbutyl)cyclopropanesulfonamide (180 mg, yield 50%) as a white solid. $^1$H NMR (300 MHz, CD$_3$Cl): δ 7.36 (s, 1H), 7.38~7.30 (m, 2H), 7.26 (s, 1H), 3.58 (t, 2H, J=6 Hz), 3.16~3.08 (m, 1H), 2.00~1.98 (m, 2H), 1.39~1.27 (m, 30H), 1.24 (s, 9H). HPLC: 90.7% at 242 nm, $t_R$=16.89 min.

Example 26: 2-(4-(2,6-di-tert-butyl-4-((2-((3,5-di-tert-butyl-4-hydroxyphenyl)thio)propan-2-yl)thio)phenoxy)-4-oxobutanamido)ethane-1-sulfonic acid

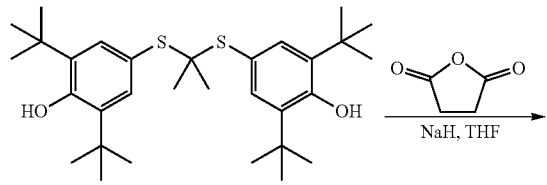

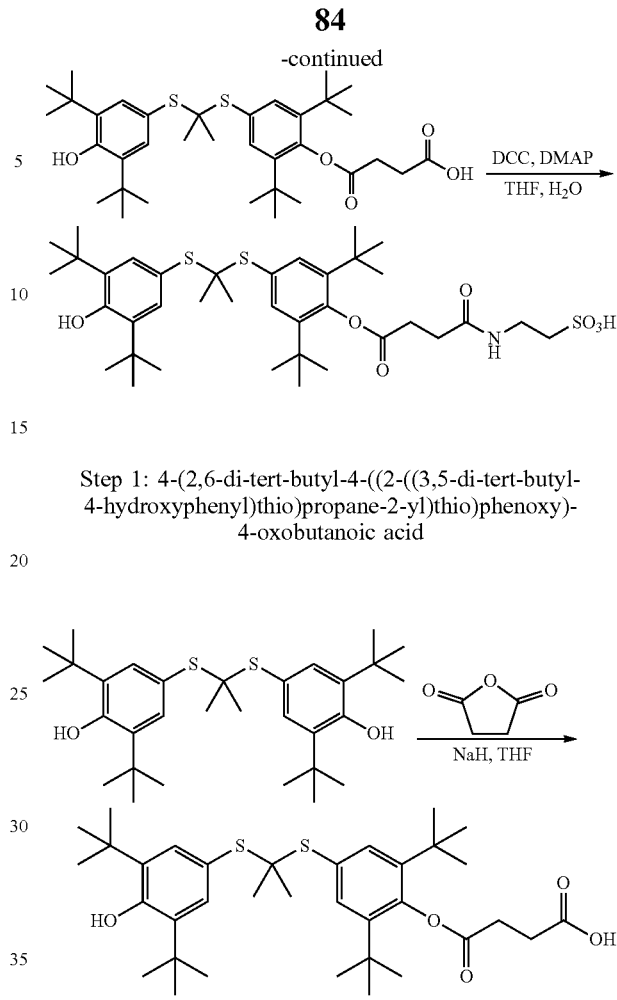

Step 1: 4-(2,6-di-tert-butyl-4-((2-((3,5-di-tert-butyl-4-hydroxyphenyl)thio)propane-2-yl)thio)phenoxy)-4-oxobutanoic acid Under the protection of N$_2$, NaH (58.3 mmol, 2.0 g of a solution in mineral oil which was used for protection, with a concentration of 70%) was added to dry THF (30 mL) in batches at 0° C., and then probucol (3.0 g, 5.8 mmol) and succinic anhydride (0.64 g, 6.4 mmol) were added. respectively. The resulting mixture was stirred at room temperature, and the reaction was monitored by TLC. After the reaction was completed, the organic solvent was removed by concentration under reduced pressure. The residue was poured into H$_2$O (50 mL), and then EtOAc (100 mL) was added. The organic phase was separated out, and dried with anhydrous sodium sulfate. The crude product was purified by chromatography (silica gel, 200 to 300 mesh, EtOAc:PE=10:1) to obtain the product as a white solid (1.2 g, yield 50%).

Step 2: 2-(4-(2,6-di-tert-butyl-4-((2-((3,5-di-tert-butyl-4-hydroxyphenyl)thio)propan-2-yl)thio)phenoxy)-4-oxobutanamido)ethane-1-sulfonic acid

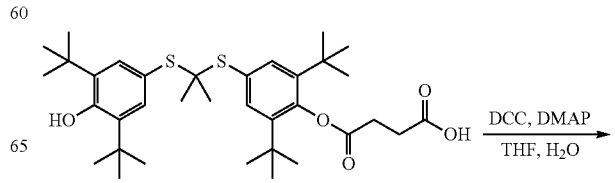

85

-continued

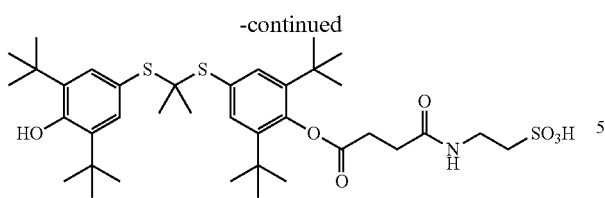

At room temperature, 4-(2,6-di-tert-butyl-4-((2-((3,5-di-tert-butyl-4-hydroxyphenyl)thio)propan-2-yl)thio)phenoxy)-4-oxobutanoic acid (1.37 g, 2.21 mmol), sulfuric acid (1.37 g, 11.055 mmol), DCC (0.68 g, 3.31 mmol) and DMAP (0.40 g, 3.31 mmol) were added to a mixed solution of THF (40 mL) and H$_2$O (20 mL), respectively. The resulting reaction solution was stirred at room temperature, and the reaction was monitored by TLC. The organic solvent was removed by concentration under reduced pressure. To the residue was added EtOAc (50 mL) and saturated salt water (10 mL) respectively. The organic phase was washed with saturated salt water and dried with anhydrous sodium sulfate. The crude product was passed through a chromatography column (silica gel, EtOAc:PE=1:50 to 1:20) to obtain the product 2-(4-(2,6-di-tert-butyl-4-((2-((3,5-di-tert-butyl-4-hydroxyphenyl)thio)propan-2-yl)thio)phenoxy)-4-oxobutanamido)ethane-1-sulfonic acid (650 mg, yield 40%) as a white foamy solid. $^1$H NMR (300 MHz, CDCl$_3$): δ 7.66 (s, 2H), 7.47 (s, 2H), 6.80 (br, 1H), 5.40 (s, 1H), 4.07 (t, 2H, J=6 Hz), 3.67 (t, 2H, J=6 Hz), 3.16 (t, 2H, J=6 Hz), 2.74 (t, 2H, J=6 Hz), 1.50 (s, 6H), 1.46 (s, 18H), 1.35 (s, 18H). HPLC: 99.7% at 242 nm, $t_R$=15.59 min.

Example 27: 2-(4-(3-(3-(tert-butyl)-5-((2-((3,5-di-tert-butyl-4-hydroxyphenyl)thio)propan-2-yl)thio)-2-hydroxyphenyl)-3-methylbutoxy)-4-oxobutanamido)ethane-1-sulfonic acid

86

Step 1: 4-oxo-4-((2-sulfoethyl)amino)butanoic acid

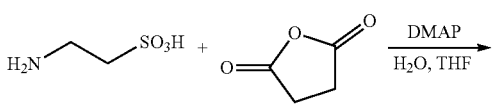

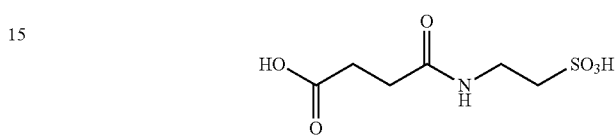

At room temperature, taurine (625 mg, 5.0 mmol), succinic anhydride (500 mg, 5.0 mmol) and DMAP (1.22 g, 10.0 mmol) were added to a mixed solution of THF (20 mL) and H$_2$O (30 mL), respectively. The resulting reaction solution was stirred at room temperature, and the reaction was monitored by LC-MS. After the taurine was completely consumed, THF was removed by concentration under reduced pressure, and the residue was freeze-dried to remove water. The resulting mixture was used in the next step without further purification. LC-MS: 224.0 [M−H]$^-$.

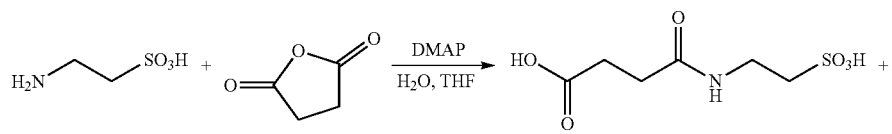

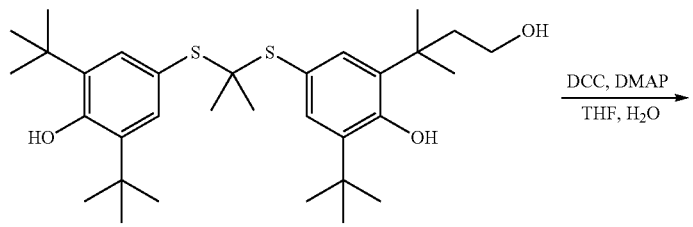

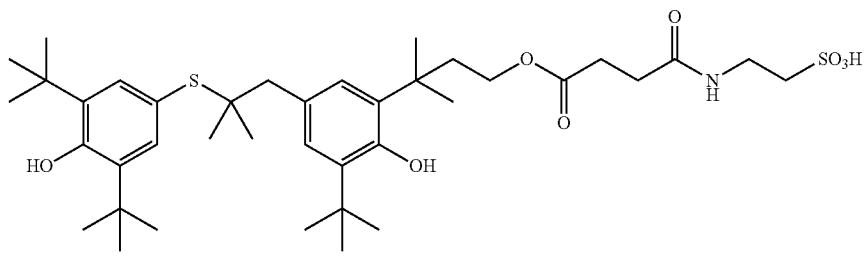

Step 2: 2-(4-(3-(3-(tert-butyl)-5-((2-((3,5-di-tert-butyl-4-hydroxyphenyl)thio)propan-2-yl)thio)-2-hydroxyphenyl)-3-methylbutoxy)-4-oxobutanamido)ethane-1-sulfonic acid

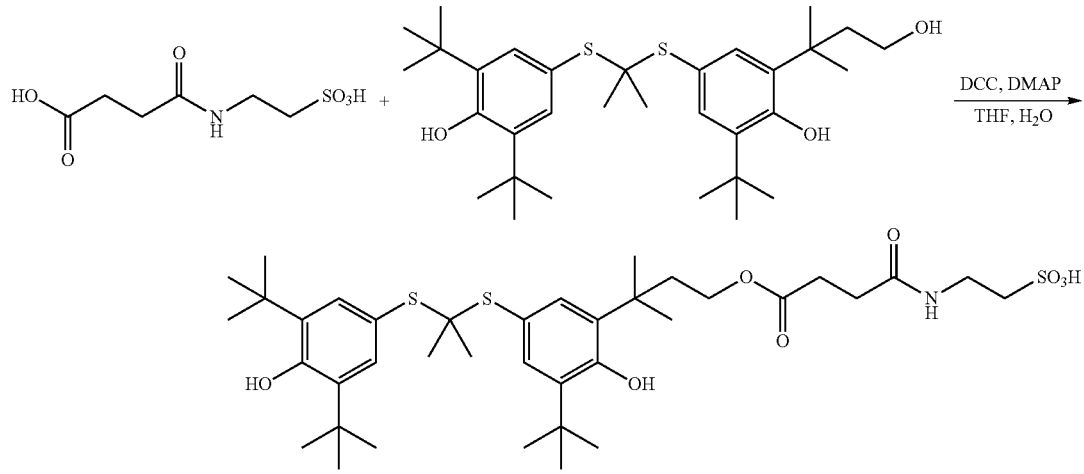

At room temperature, 4-oxo-4-((2-sulfoethyl)amino)butanoic acid (1.12 g, theoretical 5.0 mmol), 2,6-di-tert-butyl-4-((2-((3-(tert-butyl)-4-hydroxy-5-(4-hydroxy-2-methylbutan-2-yl)phenyl)thio)propan-2-yl)thio)phenol (525 mg, 0.96 mmol) and DCC (1.03 g, 5.0 mmol) were added to DMF (20 mL), respectively. The resulting reaction solution was stirred at room temperature, and the reaction was monitored by TLC. The reaction solution was poured into water, the resultant was extracted with EtOAc (100 mL), and dried with anhydrous sodium sulfate. The crude product was passed through a chromatography column (silica gel, EtOAc:PE=1:50 to 1:20) to obtain the product 2-(4-(3-(3-(tert-butyl)-5-((2-((3,5-di-tert-butyl-4-hydroxyphenyl)thio)propan-2-yl)thio)-2-hydroxyphenyl)-3-methylbutoxy)-4-oxobutanamido)ethane-1-sulfonic acid (650 mg, yield 40%) as a white foamy solid. $^1$H NMR (300 MHz, CDCl$_3$): δ 7.45 (s, 1H), 7.33 (m, 2H), 7.28 (s, 1H), 4.09 (t, 2H, J=6 Hz), 3.58 (t, 2H, J=6 Hz), 3.23 (t, 2H, J=6 Hz), 2.35 (t, 2H, J=6 Hz), 1.54~1.38 (m, 39H). HPLC: 91.6% at 242 nm, $t_R$=8.12 min.

Example 28: 2,4,9,11-tetra-tert-butyl-14,14-dimethyl-13,15-dithiodispiro[5.0.5$^7$.3$^6$]pentadeca-1,4,8,11-tetraene-3,10-dione

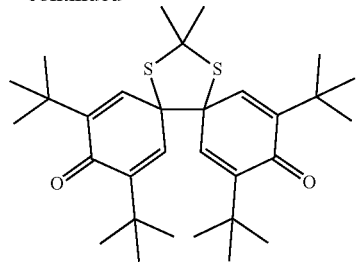

At room temperature, MnO$_2$ (1.0 g, 11.63 mmol) was added to n-heptane (10 mL), and then probucol (2.0 g, 3.88 mmol) was added in batches under stirring. The resulting reaction solution was stirred at room temperature, and the reaction was monitored by TLC. The reaction solution was filtered to remove solids. The filtrate was added with EtOAc (100 mL), washed with saturated salt water, and dried with anhydrous sodium sulfate. The obtained solid was washed with a small amount of MeOH to obtain the product 2,4,9,11-tetra-tert-butyl-14,14-dimethyl-13,15-dithiodispiro [5.0.5$^7$.3$^6$]pentadeca-1,4,8,11-tetraene-3,10-dione (1.23 g, yield 62%). $^1$H NMR (300 MHz, CDCl$_3$): δ 6.90 (s, 4H), 2.03 (s, 6H), 1.22 (s, 36H). HPLC: 92.6% at 242 nm, $t_R$=18.0 min.

Example 29: 3,3',5,5'-tetra-tert-butyl-[1,1'-bi(cyclohexylidene)]-2,2',5,5'-tetraene-4,4'-dione

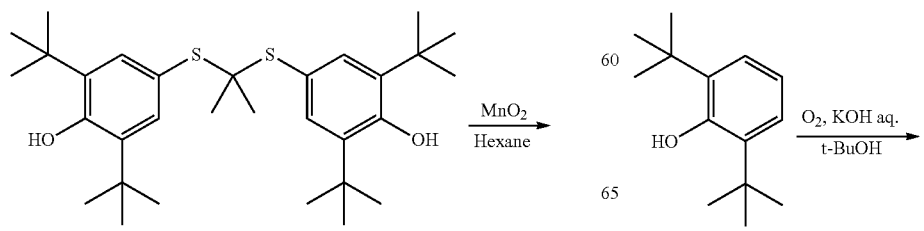

-continued

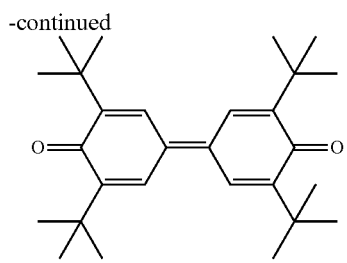

Under the atmosphere of $O_2$, KOH (2.8 g, 50.0 mmol) was first added to the mixture of tert-butanol (50 mL) and $H_2O$ (1 mL). After stirring for 10 min, 2,6-di-tert-butylphenol (2.06 g, 10.0 mmol) was added in batches. The resulting reaction solution was stirred at room temperature, and the reaction was monitored by TLC. The reaction solution was added to $H_2O$ (100 mL), stirred for 30 min, and filtered. The obtained solid was washed with a small amount of MeOH and filtered to obtain the product 3,3',5,5'-tetra-tert-butyl-[1,1'-bi(cyclohexylidene)]-2,2',5,5'-tetraene-4,4'-dione (0.66 g, yield 32%). $^1$H NMR (300 MHz, $CDCl_3$): δ 7.73 (s, 4H), 1.39 (s, 36H). HPLC: 90.0% at 242 nm, $t_R$=18.9 min.

Test Example 1 Biological Activity Test:
1. In Vitro Free Radical Inhibition Test (DPPH Method)

Principle:
The single electron of DPPH radical has a strong absorption at 517 nmL, and its alcohol solution is purple. In the presence of a free radical scavenger, the absorption of DPPH radical is weakened or disappeared for the reason that the free radical scavenger is paired with the single electron of DPPH radical, and the degree of discoloration is quantitatively related to the number of electrons DPPH radical receives. Therefore, a spectrophotometer can be used to quickly and quantitatively analyze the free radical scavenging rate of the compound.

Experimental Subjects:
Compounds 1 to 27 and four controls, i.e., compounds 28 to 31 (probucol and its two metabolites 28 and 29, and AGI-1067) in Table 1.

Experimental Procedures:
1) 1 mL solution of DPPH in absolute ethanol (concentration: 0.059 mg/mL) was taken; 2) 8 μL of the compound to be tested (20 mmol/L) were added; 3) after mixing well, the resultant was kept in dark at room temperature for 60 minutes, 4) the absorbance of the sample at 517 nm was measured. The results obtained are compared with the standard product (AGI1067), the inhibition rate of AGI1067 on DPPH was defined as 100, and the relative free radical inhibition ability of each compound in vitro was obtained. The inhibition rate of compounds on free radicals was calculated as follows:

Inhibition rate %=100*(OD value$_{DPPH\ control}$−OD value$_{sample}$)/OD value$_{DPPH}$ Experimental Results: See Table 2.

TABLE 2 scavenging rate to DPPH free radical of compounds in vitro

| Compound No. | Relative inhibition ability on free radicals | Inhibition rate % |
| --- | --- | --- |
| 1 | 85.3 | 37.2 |
| 2 | 62.1 | 27.1 |
| 3 | 100.2 | 43.7 |
| 4 | 55.2 | 24.1 |

TABLE 2-continued scavenging rate to DPPH free radical of compounds in vitro

| Compound No. | Relative inhibition ability on free radicals | Inhibition rate % |
| --- | --- | --- |
| 5 | 110.2 | 48.1 |
| 6 | 95.2 | 53.2 |
| 7 | 169.4 | 73.9 |
| 8 | 86.5 | 37.7 |
| 9 | 126.3 | 55.1 |
| 10 | 94.1 | 41.1 |
| 11 | 45.5 | 19.9 |
| 12 | 83.6 | 36.5 |
| 13 | 78.2 | 34.1 |
| 14 | 85.5 | 37.3 |
| 15 | 43.8 | 19.1 |
| 16 | 210.4 | 91.8 |
| 17 | 63.7 | 27.8 |
| 18 | 53.8 | 23.5 |
| 19 | 42.6 | 32.1 |
| 20 | 38.9 | 26.3 |
| 21 | 51.2 | 22.3 |
| 22 | 97.6 | 42.6 |
| 23 | 27.7 | 12.1 |
| 24 | 34.8 | 19.2 |
| 25 | 29.3 | 28.6 |
| 26 | 37.4 | 16.3 |
| 27 | 41.5 | 18.1 |
| 28 | 49.8 | 21.7 |
| 29 | 20.1 | 8.8 |
| 30 | 22.5 | 9.8 |
| 31 | 100.0 | 43.6 |

Test Example 2 Establishment of Golden Hamster Disease Model and Measurement of Body Weight, Blood Glucose, Blood Lipid, Cholesterol and Triglyceride 2.1 Establishment of Disease Models:
Animals and feed: 1) 8-week-old male golden hamsters with a body weight range of 100±5 g were selected; 2) 60% high-fat food; 3) 30% high-fat food; 4) general feed: NRC standard feed, containing 5% fat, total calories 4200 kcal/kg.

Animal model control group (chow): under standard environment, fed with general food and pure water.

Animal model induction group (16-week-old group): 1) fed with 60% high-fat food for 2 weeks under standard environment; 2) STZ intraperitoneal injection twice every two days, 50 mg/kg each time; 3) After STZ induction, the golden hamsters were continuous fed for 1 week; 4) Blood was taken from the ocular venous plexus, and the initial body weight, blood glucose, total cholesterol, LDL-c, HDL-c and triglyceride were measured, and the golden hamsters were grouped in parallel according to animal biochemical indicators, 8 in each group; 5) Gavage of compounds: 0.1 mL of solution of compound (concentration: 6.8 mg/mL, DMSO solution) and 0.25 mL of whole milk were mixed evenly and administered by gavage once a day for 2 weeks; 6) Blank control: 0.1 mL of DMSO and 0.25 mL of whole milk were mixed evenly and administrated by gavage once a day for 2 weeks; 7) Observation time: 14 days later, blood was taken from the ocular venous plexus, and the body weight, blood glucose, total cholesterol, LDL-c, HDL-c and triglyceride were measured.

Animal model induction group (24-week-old group): After STZ induction, the golden hamsters were continuous fed with 30% high-fat food for 8 weeks, blood was taken from the ocular venous plexus, and the initial body weight, blood glucose concentration, total cholesterol, LDL-c, HDL-c and triglyceride were measured, and the golden hamsters were grouped in parallel according to animal biochemical indicators, 8 in each group; 5) Gavage of compounds: 0.1 mL of solution of compound (concentration: 6.8 mg/mL, DMSO solution) and 0.25 mL of whole milk were mixed evenly and administered by gavage once a day for 2 weeks; 6) Blank control: 0.1 mL of DMSO and 0.25 mL of whole milk were mixed and administrated by gavage, once a day for 2 weeks; 6) Blank control: 0.1 mL of DMSO were mixed with 0.25 mL of whole milk, and administrated by gavage, once a day for 2 weeks; 7) 14 days later, blood was taken from the ocular venous plexus, and the body weight, blood glucose, total cholesterol, LDL-c, HDL-c and triglyceride were measured.

2.2 Determination of Body Weight, Blood Sugar, Blood Lipid, Cholesterol and Triglyceride Instruments: Shimadzu UV-1750 spectrophotometer, clinical determination kit (Changchun Huili Biotechnology Co., Ltd.)

Determination of blood glucose: glucose oxidase method, kit

Determination of total cholesterol (COD-PAP method), kit

Determination of low density lipoprotein cholesterol (direct method), kit

Determination of triglyceride (GP-PAP method)

Determination of high density lipoprotein (direct method), kit 2.3 Test Results: See Tables 3 to 6.

TABLE 3

Blood biochemical indexes for the animal model induction group (16-week-old group)

| Compound No. | change rate of blood glucose % | LDL % | total cholesterol % | triglyceride % | HDL % |
|---|---|---|---|---|---|
| 5 | 19.7 | −24.9 | −12.2 | −28.5 | 38.8 |
| 8 | 48.6 | 11.1 | −7.6 | 59.1 | 60.2 |
| 11 | 35.3 | −8.1 | −0.4 | 8.7 | 49.7 |
| 12 | −17.0 | −35.8 | −30.7 | −43.0 | −3.4 |
| 13 | −3.9 | −6.7 | −9.0 | −10.0 | 57.9 |
| 21 | −35.5 | 14.2 | −0.6 | −6.5 | 56.3 |
| 23 | 19.5 | −11.2 | −6.4 | 21.9 | 102.1 |
| 26 | −16.8 | −6.2 | −9.0 | 3.0 | 108.8 |
| 30 (probucol as control) | −1.5 | −12.2 | 8.7 | −6.5 | 63.3 |
| DMSO blank control | −19.8 | 0.6 | 119.0 | 39.8 | 179.1 |
| chow (general food as control) | 1.6 | −29.8 | −12.6 | −12.9 | 5.1 |

TABLE 4

Blood biochemical indexes for the animal model induction group (24-week-old group)

| New compound No. | change rate of blood glucode % | LDL % | total cholesterol % | triglyceride % | HDL % |
|---|---|---|---|---|---|
| 5 | 11.5 | −33.9 | 6.6 | −65.8 | −69.2 |
| 12 | −29.0 | −32.7 | −0.3 | −51.7 | −72.1 |
| 21 | −12.4 | −21.8 | 23.5 | −65.1 | −70.1 |
| 26 | −14.2 | −23.0 | 30.5 | −5.1 | −67.5 |
| DMSO blank control | −4.2 | −9.4 | 16.6 | 10.0 | −62.7 |

TABLE 5

Changes in body weight in the animal model induction group (16-week-old group)

| New compound No. | average body weight at 16 weeks/g | average body weight after administration/g | change of body weight/g | change rate of body weight % | change rate of body weight after deduction of DMSO blank % |
|---|---|---|---|---|---|
| 5 | 134.6 | 145.2 | 10.6 | 7.9 | −1.9 |
| 8 | 143.7 | 149.0 | 5.3 | 3.7 | −6.1 |
| 11 | 135.1 | 140.9 | 5.8 | 4.3 | −5.5 |
| 12 | 137.7 | 135.4 | −2.3 | −1.6 | −1.6 |
| 13 | 133.9 | 136.6 | 2.6 | 2.0 | −7.8 |

TABLE 5-continued

Changes in body weight in the animal model induction group (16-week-old group)

| New compound No. | average body weight at 16 weeks/g | average body weight after administration/g | change of body weight/g | change rate of body weight % | change rate of body weight after deduction of DMSO blank % |
|---|---|---|---|---|---|
| 21 | 131.8 | 142.5 | 10.7 | 8.1 | −1.6 |
| 23 | 138.9 | 147.2 | 8.3 | 6.0 | −3.8 |
| 26 | 135.8 | 145.2 | 9.4 | 6.9 | −2.9 |
| 30 (probucol as control) | 133.7 | 141.3 | 7.6 | 5.7 | −4.1 |
| DMSO-blank control | 143.1 | 157.0 | 9.8 | 9.8 | 0.0 |

TABLE 6

Changes in body weight in the animal model induction group (24-week-old group)

| New compound No. | average body weight at 24 weeks/g | change of body weight/g | change rate of body weight % | change rate of body weight after deduction of DMSO blank % |
|---|---|---|---|---|
| 5 | 118.1 | −25.0 | −21.1 | −13.6 |
| 12 | 122.4 | −17.3 | −14.2 | −6.6 |
| 21 | 120.0 | −16.4 | −13.6 | −6.1 |
| 26 | 130.1 | −18.1 | −13.9 | −6.4 |
| DMSO-blank control | 124.3 | −9.4 | −7.5 | 0.0 |
| general food-blank control | 132.8 | −5.5 | −4.1 | — |

Test Example 3 In Vivo Anti-Lipid Oxidation Experiment

Experimental principle: Malondialdehyde (MDA) in liposome degradation products could condense with thiobarbituric acid (TBA) to form a red product which has a maximum absorption peak at 532 nm. The spectrophotometer was used to measure the relative absorption value to calculate the antioxidant value.

Materials and instruments: visible spectrophotometer, 95° C. constant temperature water-bath box, and centrifuge.

Solutions and Reagent Preparations:

Reagents: Malondialdehyde (MDA) test kit (article number: A003-1, TBAF method, Nanjing Jiancheng), glacial acetic acid of analytically pure grade.

Reagent preparations: 1) Reagent I: Reagent 1 in the kit was taken out from the refrigerator and subjected to natural warming until a transparent liquid is obtained; 2) Reagent II: 170 mL of double-distilled water was added to each bottle and mixed; 3) Reagent III: A dry powder in the kit was dissolved in 60 mL of double-distilled water at 90 to 100° C. After the dry powder was dissolved totally, 30 mL of glacial acetic acid was added and kept in dark place; 4) Standard: 10 nmol/mL tetraethoxypropane.

Experimental procedures: 1) Blank tube: To 2 mL centrifuge tube were added anhydrous ethanol (70 µl), Reagent I (70 µl), Reagent II (0.8 mL) and Reagent III (0.8 mL) in sequence; 2) Standard tube: To 2 mL centrifuge tube were added standard (70 µl), Reagent I (70 µl), Reagent 11 (0.8 mL) and Reagent III (0.8 mL) in sequence; 3) Measuring tube: To 2 mL centrifuge tube were added the serum to be tested and physiological saline (the total volume of serum and physiological saline is 70 µl), Reagent I (70 µl), Reagent II (0.8 mL) and Reagent III (0.8 mL) in sequence; 4) Control tubes: all samples are set up with corresponding control tubes. To a 2 mL centrifuge tube were added the serum to be tested and physiological saline (the total volume of serum and physiological saline is 70 µl), Reagent I (70 µl), Reagent II (0.8 mL) and 50% glacial acetic acid (0.8 mL) in sequence.

After the above reagents were added, the mixture was mixed homogenously. Then the mixture was left in the water bath at 95° C. for 60 minutes. The sample was centrifuged at 4000 rpm for 10 minutes. The supernatant was taken for the measurement of the OD value.

Experimental data processing: the MDA content in serum was calculated as follows:

$$MDA = (OD\ value_{measured} - OD\ value_{control})/OD\ value_{standard} * concentration\ of\ the\ standard$$

$$Inhibition\ rate\ \% = 100 - (OD_{sample-average\ value} - average\ value\ of\ Chow)/(average\ value\ of\ the\ solvent\ DMSO - average\ value\ of\ Chow) * 100$$

Experimental Results: See Table 7.

TABLE 7

MAD lipid peroxidation in vivo

| New compound No | avarage value of OD | standard deviation | inhibition rate % |
|---|---|---|---|
| 1 | 7.20 | 2.34 | 54.1 |
| 2 | 6.45 | 1.98 | 73.5 |
| 3 | 7.94 | 1.56 | 34.9 |
| 4 | 6.03 | 1.67 | 84.4 |
| 5 | 6.21 | 2.86 | 79.6 |
| 6 | 6.54 | 2.12 | 71.2 |
| 7 | 7.45 | 1.98 | 47.6 |

TABLE 7-continued

MAD lipid peroxidation in vivo

| New compound No | avarage value of OD | standard deviation | inhibition rate % |
|---|---|---|---|
| 8 | 6.98 | 1.87 | 59.8 |
| 9 | 6.86 | 1.90 | 62.9 |
| 10 | 7.45 | 2.12 | 47.6 |
| 11 | 7.56 | 2.31 | 44.7 |
| 12 | 6.82 | 1.48 | 64.0 |
| 13 | 7.21 | 2.12 | 53.8 |
| 14 | 7.13 | 2.01 | 55.9 |
| 15 | 7.34 | 2.21 | 50.5 |
| 16 | 8.32 | 1.80 | 25.0 |
| 17 | 6.43 | 2.45 | 74.0 |
| 18 | 7.21 | 2.78 | 53.8 |
| 19 | 8.21 | 2.10 | 27.9 |
| 20 | 8.10 | 1.97 | 30.7 |
| 21 | 7.23 | 1.56 | 53.3 |
| 22 | 7.89 | 2.42 | 36.2 |
| 23 | 6.10 | 1.87 | 82.6 |
| 24 | 7.23 | 2.12 | 53.3 |
| 25 | 7.43 | 2.56 | 48.1 |
| 26 | 5.10 | 1.64 | 108.7 |
| 27 | 8.12 | 2.34 | 30.2 |
| 28 | 9.12 | 2.12 | 4.3 |
| 29 | 8.98 | 2.89 | 7.9 |
| 30 | 7.23 | 2.12 | 53.3 |
| 31 | 7.39 | 1.97 | 49.1 |
| DMSO | 9.29 | 2.63 | — |
| Chow | 5.43 | 1.14 | — |

Although the present invention has been described in detail above with general description and specific examples, on the basis of the present invention, some modifications or improvements can be made, which is obvious to a person skilled in the art. Therefore, these modifications or improvements made without departing from the spirit of the present invention belong to the protection scope of the present invention.

INDUSTRIAL APPLICABILITY

The present invention provides a probucol derivative having the structure represented by general formula I.

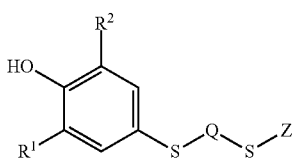

The invention also provides a preparation method and use of the probucol derivative. The probucol derivative provided by the present invention can be used for the prevention and treatment of vascular diseases including diabetes, cardio-cerebrovascular diseases, or complications thereof, and can be effectively used for reducing blood glucose, reducing blood lipid, reducing cholesterol, reducing body weight, reducing triglyceride, anti-inflammatory and anti-oxidation and the like, and have good economic value and broad prospective applications.

What is claimed is:

1. A probucol derivative having a structure represented by general formula I:

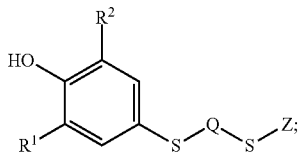

herein $R^1$ and $R^2$ are selected from the group consisting of hydrogen, an alkyl group and an alkoxy group, where the alkyl or the alkoxy group is optionally substituted with a hydroxyl group, a cycloalkyl group, an alkenyl group, an ester group, a carboxylic group, a cyano group, an amino group, a nitro group, an amide group, a sulfonyl group, —$ONO_2$, an ether group, an aryl group, a heteroaryl group or halogen; and the amino group is optionally substituted with an alkyl group or a cycloalkyl group;

Q is —$CR^5R^6$, where $R^5$ and $R^6$ are selected from the group consisting of an alkyl group, an alkenyl group, and an aryl group; the alkyl group, alkenyl group, or aryl group is optionally substituted with a hydroxyl group, an alkyl group, an alkenyl group, an amide group, an ester group, a carbonyl group, a cyano group, an amino group, a nitro group or halogen; and the amino group is optionally substituted with a branched or linear alkyl group containing $C_1$-$C_6$ or a 3- to 5-membered cycloalkyl group; and Z is an aryl group or an alkyl group, where the aryl group is substituted with halogen, an alkyl group, a cycloalkyl group, an alkenyl group, a cyano group, an amino group, a heteroaryl group, —$NR^{12}R^{13}$, —$COOR^{12}$, —$CONR^{12}R^{13}$, —$NR^{12}COR^{13}$, —$SO_2R^{12}$, —$ONO_2$, —$SO_3H$, —$CO_2H$ or —$NR^{12}SO_2R^{13}$; and the alkyl group is optionally substituted with halogen, a hydroxyl group, a cycloalkyl group, a cyano group, an amino group, an aryl group, a heteroaryl group, —$NR^{12}R^{13}$, —$OR^{12}$, —$COOR^{12}$, —$CONR^{12}R^{13}$, —$NR^{12}COR^{13}$, —$SO_2R^{12}$, —$ONO_2$, —$SO_3H$, —$CO_2H$ or —$NR^{12}SO_2R^{13}$; wherein $R^{12}$ and $R^{13}$ are selected from the group consisting of a hydroxyl group, a cycloalkyl group, an alkenyl group, an amide group, an ester group, a cyano group, an amino group, a nitro group, halogen, a saturated heterocyclic group, an aryl group and a heteroaryl group.

2. A probucol derivative having a structure represented by general formula III:

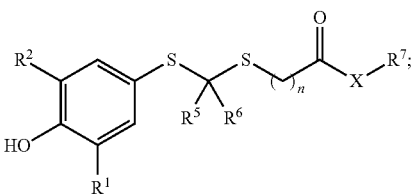

herein $R^1$ and $R^2$ are selected from the group consisting of hydrogen, an alkyl group and an alkoxy group, where the alkyl or alkoxy group is optionally substituted with a hydroxyl group, a cycloalkyl group, an alkenyl group, an ester group, a carboxylic group, a cyano group, an amino group, a nitro group, an amide group, a sulfonyl group, —$ONO_2$, an ether group, an aryl group, a heteroaryl group or halogen; and the amino group is optionally substituted with an alkyl group or a cycloalkyl group;

$R^5$ and $R^6$ are selected from the group consisting of an alkyl group, an alkenyl group, and an aryl group, where the alkyl group, alkenyl group, or aryl group is optionally substituted with a hydroxyl group, an alkyl group, an alkenyl group, an acyl group, an ester group, a carboxylic group, a cyano group, an amino group, a nitro group or halogen;

n is an integer of 1 to 4;

X is O; and $R^7$ is selected from the group consisting of a hydroxyl group, a cycloalkyl group, an alkenyl group, an amide group, an ester group, a cyano group, an amino group, a nitro group, halogen, a saturated heterocyclic group, an aryl group and a heteroaryl group.

3. A probucol derivative having a structure represented by general formula IV:

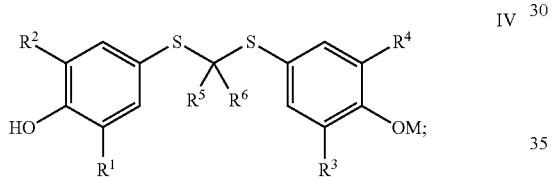

herein $R^1$, $R^2$, $R^3$ and $R^4$ are selected from the group consisting of hydrogen, an alkyl group and an alkoxy group, where the alkyl or the alkoxy group is optionally substituted with a hydroxyl group, a cycloalkyl group, an alkenyl group, an ester group, a carboxylic group, a cyano group, an amino group, a nitro group, an amide group, a sulfonyl group, —$ONO_2$, an ether group, an aryl group, a heteroaryl group or halogen; and the amino group is optionally substituted with an alkyl group or a cycloalkyl group;

M is —$CO(CH_2)_mCONHR^{14}$, where m is an integer of 2 to 4; $R^{14}$ is an alkyl group, an aryl group or a heteroaryl group; the alkyl group is optionally substituted with a carboxylic group, a sulfonic acid group, —$ONO_2$, an amide group or a cyano group; and $R^5$ and $R^6$ are selected from the group consisting of an alkyl group, an alkenyl group and an aryl group, where the alkyl group, alkenyl group or aryl group is optionally substituted with a hydroxyl group, an alkyl group, an alkenyl group, an amide group, an ester group, a carbonyl group, a cyano group, an amino group, a nitro group or halogen; and the amino group is optionally substituted with branched or linear alkyl group containing $C_1$-$C_6$ or a 3- to 5-membered cycloalkyl group.

4. A probucol derivative having a structure represented by general formula V:

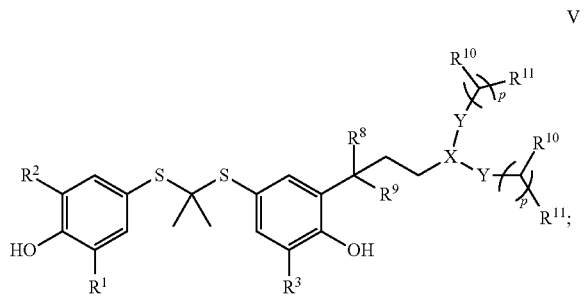

herein $R^1$, $R^2$ and $R^3$ are selected from the group consisting of hydrogen, an alkyl group and an alkoxy group, where the alkyl or the alkoxy group is optionally substituted with a hydroxyl group, a cycloalkyl group, an alkenyl group, an ester group, a carboxylic group, a cyano group, an amino group, a nitro group, an amide group, a sulfonyl group, —$ONO_2$, an ether group, an aryl group, a heteroaryl group or halogen; and the amino group is optionally substituted with an alkyl group or a cycloalkyl group;

$R^8$ and $R^9$ are selected from the group consisting of a $C_1$-$C_6$ linear or branched alkyl group, a cycloalkyl group, an aryl group and a heteroaryl group;

X is NH, N, O or S;

Y is a heteroaryl group, —$CH_2$— or —C(O);

when X is NH, O or S, one instance of —$Y(CHR^{10})_pR^{11}$ is absent;

p is an integer from 0 to 6; and $R^{10}$ and $R^{11}$ are selected from the group consisting of hydrogen, an amino group, an aryl group, a heteroaryl group and an alkyl group, where the amino group, aryl group, heteroaryl group or alkyl group is optionally substituted with halogen, a hydroxyl group, a saturated heterocyclic hydrocarbyl group, an alkenyl group, a cyano group, an aryl group, a heteroaryl group, —$NR^{15}R^{16}$, —$OR^{15}$, —$COOR^{15}$, —$CONR^{15}R^{16}$, —$NR^{15}COR^{16}$, —$SO_2R^{15}$, —$ONO_2$, —$SO_3H$, —$CO_2H$ or —$NR^{15}SO_2R^{16}$; the saturated heterocyclic hydrocarbyl group is selected from a 4- to 12-membered saturated monocyclic, bicyclic or tricyclic group having at least one carbon atom and at least one heteroatom; the at least one heteroatom is selected from N, O or S; the number of the at least one heteroatom is 1 to 4; $R^{15}$ and $R^{16}$ are selected from the group consisting of a hydroxyl group, an alkyl group, a cycloalkyl group, an alkenyl group, an amide group, an ester group, a carboxylic group, a sulfonic acid group, a cyano group, an amino group, a nitro group, halogen, an aryl group and an heteroaryl group.

5. A method for preparing the probucol derivative of claim 4, the method comprising:

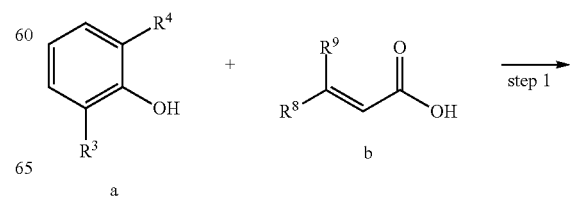

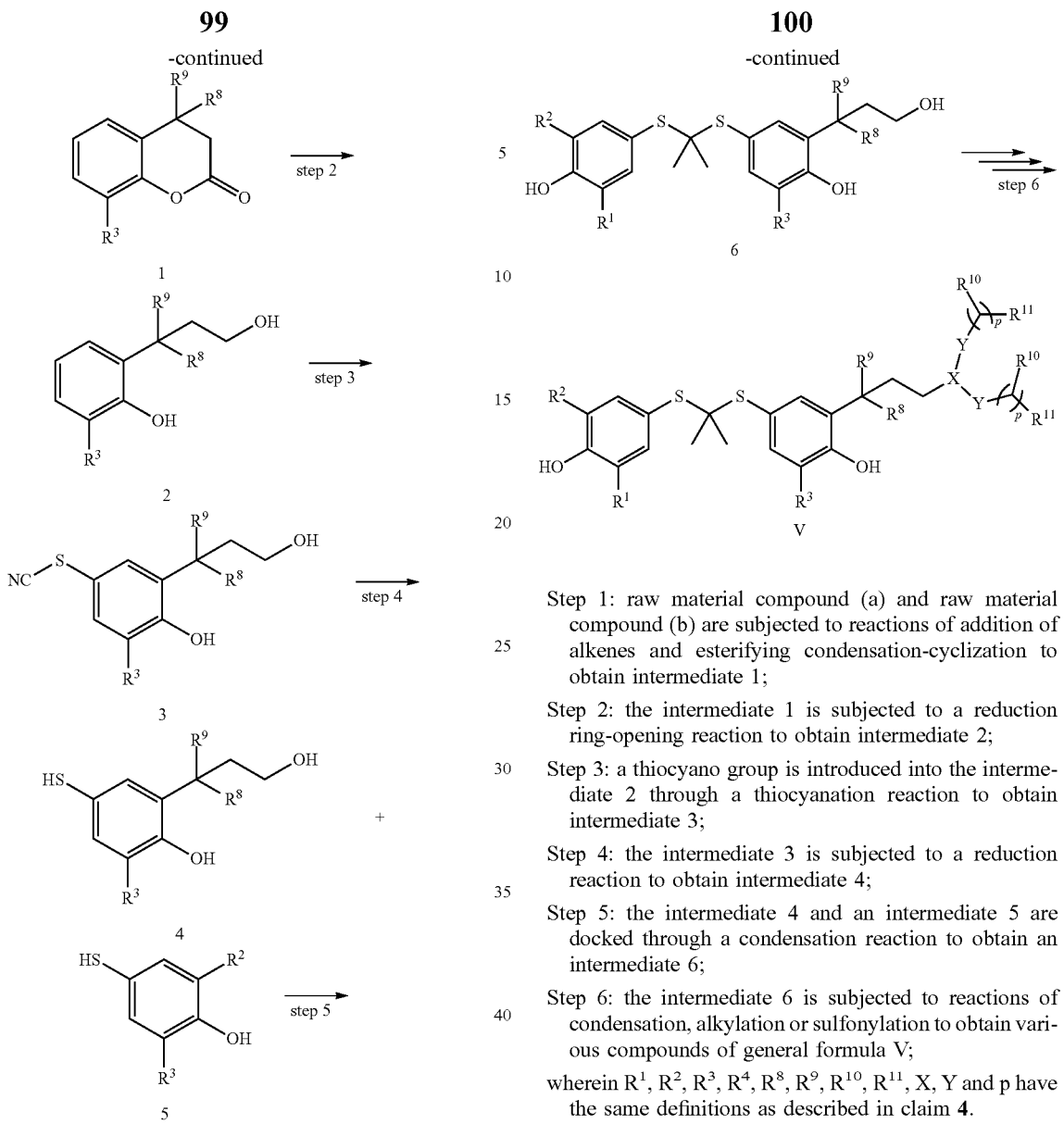

Step 1: raw material compound (a) and raw material compound (b) are subjected to reactions of addition of alkenes and esterifying condensation-cyclization to obtain intermediate 1;

Step 2: the intermediate 1 is subjected to a reduction ring-opening reaction to obtain intermediate 2;

Step 3: a thiocyano group is introduced into the intermediate 2 through a thiocyanation reaction to obtain intermediate 3;

Step 4: the intermediate 3 is subjected to a reduction reaction to obtain intermediate 4;

Step 5: the intermediate 4 and an intermediate 5 are docked through a condensation reaction to obtain an intermediate 6;

Step 6: the intermediate 6 is subjected to reactions of condensation, alkylation or sulfonylation to obtain various compounds of general formula V;

wherein $R^1$, $R^2$, $R^3$, $R^4$, $R^8$, $R^9$, $R^{10}$, $R^{11}$, X, Y and p have the same definitions as described in claim 4.

* * * * *